US008068990B2

(12) United States Patent
Rosenfeld et al.

(10) Patent No.: US 8,068,990 B2
(45) Date of Patent: Nov. 29, 2011

(54) DIAGNOSIS OF INTRA-UTERINE INFECTION BY PROTEOMIC ANALYSIS OF CERVICAL-VAGINAL FLUIDS

(75) Inventors: Ron Rosenfeld, Los Altos, CA (US); Srinivasa Nagalla, Hillsboro, OR (US); Mike Gravett, Portland, OR (US)

(73) Assignee: Hologic, Inc., Marlborough, MA (US)

(*) Notice: Subject to any disclaimer, the term of this patent is extended or adjusted under 35 U.S.C. 154(b) by 1314 days.

(21) Appl. No.: 11/595,221

(22) Filed: Nov. 9, 2006

(65) Prior Publication Data

US 2007/0161125 A1    Jul. 12, 2007

Related U.S. Application Data

(63) Continuation-in-part of application No. 11/473,797, filed on Jun. 22, 2006, now abandoned, and a continuation-in-part of application No. 10/400,005, filed on Mar. 25, 2003, now Pat. No. 7,191,068.

(51) Int. Cl.
C12Q 1/68 (2006.01)
G01N 33/48 (2006.01)
G06G 7/58 (2006.01)

(52) U.S. Cl. .................. 702/19; 435/4; 435/7; 702/20; 703/11

(58) Field of Classification Search .................. None
See application file for complete search history.

(56) References Cited

U.S. PATENT DOCUMENTS

| | | | |
|---|---|---|---|
| 5,484,705 A | 1/1996 | White |
| 5,516,702 A | 5/1996 | Senyei et al. |
| 5,804,367 A | 9/1998 | White |
| 5,871,937 A | 2/1999 | Ulevitch |
| 5,891,618 A | 4/1999 | White |
| 5,928,624 A | 7/1999 | Wright |
| 6,036,955 A | 3/2000 | Thorpe |
| 6,406,921 B1 | 6/2002 | Wagner et al. |
| 6,703,202 B2 | 3/2004 | McGrath |
| 6,974,704 B2 | 12/2005 | Nelson |
| 7,081,334 B2 | 7/2006 | White |
| 7,191,068 B2 | 3/2007 | Rosenfeld |
| 7,323,346 B2 | 1/2008 | Thadhani |
| 7,396,687 B2 | 7/2008 | Nelson |
| 2001/0012537 A1 | 8/2001 | Anderson et al. |
| 2003/0054422 A1 | 3/2003 | Badley |
| 2004/0126781 A1 | 7/2004 | Ling |
| 2004/0241775 A1 | 12/2004 | Romero et al. |
| 2005/0148023 A1 | 7/2005 | Thadhani |
| 2006/0063162 A1 | 3/2006 | Deng |
| 2006/0121531 A1 | 6/2006 | Wei et al. |
| 2006/0240495 A1 | 10/2006 | Buhimschi |
| 2006/0246495 A1 | 11/2006 | Garrett |
| 2007/0037224 A1 | 2/2007 | Hamer |
| 2007/0092911 A1 | 4/2007 | Buechler |
| 2007/0178605 A1 | 8/2007 | Mor |
| 2007/0280941 A1 | 12/2007 | Chung |
| 2008/0031874 A1 | 2/2008 | Sanders |
| 2008/0114576 A1 | 5/2008 | Jackson |
| 2008/0199426 A1 | 8/2008 | Sukhatme |
| 2008/0213794 A1 | 9/2008 | Thadhani |
| 2008/0318836 A1 | 12/2008 | Woolfson |
| 2009/0075387 A1 | 3/2009 | Kalns |
| 2009/0171590 A1 | 7/2009 | Puskas |

FOREIGN PATENT DOCUMENTS

| | | |
|---|---|---|
| EP | A 1 143 246 | 10/2001 |
| WO | WO 9520163 | 7/1995 |
| WO | WO 9531902 | 11/1995 |
| WO | WO 9641172 | 12/1996 |
| WO | WO 00/52471 | 9/2000 |
| WO | WO 0233408 | 4/2002 |
| WO | WO 03097872 | 11/2003 |
| WO | WO2004/043238 | 5/2004 |
| WO | WO2004/045379 | 6/2004 |
| WO | WO 2004/072638 A1 | 8/2004 |
| WO | WO 2007002264 | 1/2007 |
| WO | WO 2007002527 | 1/2007 |
| WO | WO 2007002535 | 1/2007 |
| WO | WO 2007013919 | 2/2007 |
| WO | WO 2007092353 | 8/2007 |
| WO | WO 2007112514 | 10/2007 |
| WO | WO 2008124096 | 10/2008 |
| WO | WO 2008157383 | 12/2008 |
| WO | WO 2009013538 | 1/2009 |

OTHER PUBLICATIONS

Agerberth, B., et al., "FALL-39, a putative human peptide antibiotic, is cysteine-free and expressed in bone marrow and testis", *Proc. Natl. Acad. Sci.*, USA 3;92(1):195-199, 1995.

Arai, M., et al., "Differential Developmentally Regulated Expression of Gelsolin Family Members in the Mouse", *Dev. Dyn.*, 215, 297-307, 1999.

Ball, et al., "An integrated approach utilizing artifical neural networks and SELDI mass spectrometry for the classification of human tumors and rapid identification of potential biomarkers", *Bioinformatics* 18(3):395-404, 2002.

Bejar, R., et al., "Antenatal origin of neurologic damage in newborn infants, I. Preterm Infants", *Am. J. Obstet. Gynecol.* 159(2):357-363, Aug. 1988.

Courchesna and Patterson, "Identification of Proteins by Matrix-Assisted Laser Desorption/Ionization Mass Spectrometry Using Peptide and Fragment Ion Masses", *Methods Mol. Biol.* 112(2-D):487-511, 1999.

(Continued)

*Primary Examiner* — Shubo Zhou
(74) *Attorney, Agent, or Firm* — James A. Fox; Ginger R. Dreger; Arnold & Porter LLP

(57) ABSTRACT

The invention concerns the identification of proteomes of biological fluids and their use in determining the state of maternal/fetal conditions, including maternal conditions of fetal origin, chromosomal aneuploidies, and fetal diseases associated with fetal growth and maturation. In particular, the invention concerns a comprehensive proteomic analysis of human amniotic fluid (AF) and cervical vaginal fluid (CVF), and the correlation of characteristic changes in the normal proteome with various pathologic maternal/fetal conditions, such as intra-amniotic infection, pre-term labor, and/or chromosomal defects. The invention further concerns the identification of biomarkers and groups of biomarkers that can be used for non-invasive diagnosis of various pregnancy-related disorders, and diagnostic assays using such biomarkers.

9 Claims, 28 Drawing Sheets

OTHER PUBLICATIONS

Creasy, R.K., et al., "Preterm Labor and Delivery", in *Maternal-Fetal Medicine*, Creasy, R.K., Resnik, R., (eds.), W. B. Saunders Company, Philadelphia, PA, 4th edition, Chapter 32, pp. 498-531, 1999.

Cuckle, H., "Biochemical screening for Down syndrome", *Eur. J. Obstet Gynecol Reprod. Biol.*, 92(1):97-101, 2000.

Dabiri, G.S., "Molecular Cloning of Human Macrophage Capping Protein cDNA. A Unique Member of the Gelsolin/Villin Family Expressed Primarily in Macrophages", *J. Biol. Chem.*, 267(23):16545-16552, 1992.

Ducsay, C.A., et al., "Simplified Vest and Tether System for Maintenance of Chronically Catheterized Pregnant Rhesus Monkeys", *Lab. Anim. Sci.*, 38(3):343-344, Jun. 1988.

Duff, P., et al., "The course of labor in term patients with chorioamnionitis", *American Journal of Obstetrics and Gynecology*, 147(4):391-395, Oct. 1983.

Gibbs, R.S., et al., "Management of acute chorioamnionitis", *American Journal of Obstetrics and Gynecology*, 136(6):709-713, Mar. 1980.

Gilstrap III, L.C., et al., "Intrapartum treatment of acute chorioamnionitis: Impact on neonatal sepsis", *Am. J. Obstet. Gynecol.* 159(3):579-583, Sep. 1988.

Goetz, D.H., et al., "The Neutrophil Lipocalin NGAL is a Bacteriostatic Agent that Interferes with Siderophore-Mediated Iron Acquisition", *Mol. Cell*, 10(5):1033-1043, 2002.

Gravett, et al., "An experimental model for intraamniotic infection and preterm labor in rhesus monkeys", *Am. J. Obstet. Gynecol.*, 171(6):1660-7, Dec. 1994.

Gravett, Michael, et al., "Diagnosis of Intra-amniotic Infection by Proteomic Profiling and Identification of Novel Biomarkers", Journal of American Medical Association, vol. 292, No. 4, pp. 462-469, Jul. 28, 2004.

Greene, Nicholas, et al., "Differential Protein Expression at the Stage of Neural Tube Closure in the Mouse Embryo", The Journal of Biological Chemistry, vol. 277, No. 44, Issue of Nov. 1, pp. 41645-41651, 2002.

Grether, J.K., et al., "Maternal Infection and Cerebral Palsy in Infants of Normal Birth Weight", *JAMA* 278(3):207-211, Jul. 1997.

Gulesserian, Talin. et al., Aberrant Expression of Centractin and Capping Proteins, Integral Constituents of the Dynactin Complex, in Fetal Down Syndrome Brain, Biochemical and Biophysical Research Communication, vol. 291, No. 1, pp. 62-67, Feb. 15, 2002.

Gursoy, T., et al., "Preeclampsia Disrupts the Normal Physiology of Leptin", *Am. J. Perinatol*, 19(6):303-310, 2002.

Haluska, G.J., et al., "Temporal changes in uterine activity and prostaglandin response to RU486 in rhesus macaques in late gestation", *Am. J. Obstet. Gynecol*, 157:1487-1495, 1987.

Hitti, J., et al., "Amniotic fluid tumor necrosis factor-α and the risk of respiratory distress syndrome among preterm infants", *Am. J. Obstet. Gynecol.* 177:50-56, 1997.

Hook, E. B., et al., "The Frequency of Chromosome Abnormalities Detected in Consecutive Newborn Studies—Differences Between Studies—Results by Sex and by Severity of Phenotypic Involvement", in Hook, E.B., Porter, I.H. (eds.), *Population Cytogenetics*, pp. 63-79, New York, Academic Press, 1978.

Issaq, J.H., et al., "The SELDI-TOF MS Approach to Proteomins: Protein Profiling and Biomarker Identification", *Biochem. Biophys. Res. Commun.*, 5;292(3):587-92, 2000.

Jensen, O.N., et al., "Direct observation of UV-crosslinked Protein-Nucleic Acid Complexes by Matrix-assisted Laser Desorption Oonization Mass Spectrometry", *Rapid Commun. Mass. Spectrom.*, 7:496-501, 1993.

Li, et al., "Proteomics and Bioinformatics Approaches for Identification of Serum Biomarkers to Detect Breast Cancer", *Clinical Chemistry Journal*, 48(8):1296-1304, 2002.

Liberatori, Sabrina, et al., "A two-dimensional protein map of human amniotic fluid at 17 weeks' gestation", Electrophoresis, vol. 18, p. 2816-2822, Dec. 1997.

Lomas, D.A., et al., "Serpinopathies and the Conformational Dementias", *Nat. Rev. Genet* 3:759-768, 2002.

Lopez-Zeno, J.A., et al., "A Controlled Trial of a Program for the Active Management of Labor", *N. Engl. J. Med.* 326(7):450-454, Feb. 1992.

Marvin, L., et al., "Identification of proteins from one-dimensional sodium dodecyl sulfate-polyacrylamide gel electrophoresis using electrospray quadrupole-time-of-flight tandem mass spectrometry", *Rapid Commun. Mass. Spectrom.* 14:1287-1292, 2000.

Mels, P.J., et al., "Factors associated with preterm birth in Cardiff, Wales: II. Indicated and spontaneous preterm birth", *Am. J. Obstet. Gynecol.*, 173(2):597-602, Aug. 1995.

Morales, W.J., "The Effect of Chorioamnionitis on the Developmental Outcome of Preterm Infants at One year", *Obstetrics and Gynecology*, 70(2):183-186, Aug. 1987.

Newton, E.R., "Chorioamnionitis and Intraamniotic Infection", *Clin. Obstet. Gynecol.*, 36(4):795-808, Dec. 1993.

Newton, E.R., et al., "Logistic Regression Analysis of Risk Factors for Intra-Amniotic Infection", *Obstet. Gynecol.*, 73(4):571-575, Apr. 1989.

OhIsson, A., et al., "An analysis of antenatal tests to detect infection at preterm premature rupture of the membranes", *American Journal of Obstetrics and Gynecology*, 162(3):809-818, Mar. 1990.

Pellieux, Corinne, et al., "Cap G, a Gelsolin Family Protein Modulating Protective Effects of Unidirectional Shear Stress", The Journal of Biological Chemistry, vol. 278, No. 31, Issue of Aug. 1, pp. 29136-29144, 2003.

Pereira, H.A., "CAP37, a neutrophil-derived multifunctional inflammatory mediator", *J. Leukoc Biol.* 57:805-812, 1995.

Petricoin, III, E.F., et al., "Use of poteomic patterns in serum to identify ovarian cancer", *The Lancet* 359:572-77, Feb. 2002.

Romero, R., et al., "The Role of Systemic and Intrauterine Infection in Preterm Parturition", *Annuals of the New York Academy of Sciences* 622:355-375, May 1991.

Romero, Roberto, et al., "Proteomic profiling of premature labor: A method to identify clinical biomarkers and mechanisms of disease", American Journal of Obstetrics and Gynecology, vol. 189, No. 6, Supplement, Sep. 2003.

Schweitzer, B., et al., "Measuring proteins on microarrays", *Curr. Opin. Biotechnol.*, 13:14-9, 2002.

Soper, D.E., et al., "Risk factors for intraamniotic infection: A prospective epidemicologic study", *American Journal of Obstetrics and Gynecology* 161(3):562-568, Sep. 1989.

Speck, O., et al., "Moesin functions antagonistically to the Rho pathway to maintain epithelial integrity", *Nature* 421(2):83-87, 2003.

Tabb, Di., et al., "DTASelect and Contrast: Tools for Assembling and Comparing Protein Identifications from Shotgun Proteomics", *J. Proteome Res.* 1:21-26, 2002.

Tang, B.L., "Inhibitors of neuronal regeneration: mediators and signaling mechanisms", *Neurochem. Int.*, 42(3):189-203, 2003.

Tashima, Lily, et al., "Genes Unregulated in Human Fetal Membranes by Infection or Labor", *Obstetrics and Gynecology*, vol. 94. No. 3, Sep. 1999.

Taylor, J.A., et al., "Implementation and Uses of Automated de Novo Peptide Sequencing by Tandem Mass Spectrometry", *Anal. Chem.* 73(11):2594-604, 2001.

Thorey, I.S., et al., "The $Ca^{2+}$-binding Proteins S100A8 and S100A9 Are Encoded by Novel Injury-regulated Genes", *J. Biol. Chem.* 276(38):35818-35825, 2001.

Vadillo-Ortega et al., Am. J. Obstet. Gynecol., vol. 186, pp. 128-138, Jan. 2002.

Vray, B., et al., "Immunomodulatory properties of cystatins", *Cell Mol. Life Sci.*, 59:1503-1512, 2002.

Watts, D.H., et al., "The Association of Occult Amniotic Fluid Infection with Gestational Age and Neonatal Outcome Among Women in Preterm Labor", *Obstet. Gynecol.* 79(3):351-357, Mar. 1992.

Weitzdoerfer, R., et al., "Reduction of actin-related protein complex 2/3 in fetal Down syndrome brain", *Biochem. Biophys. Res. Commun.* 293:836-841, 2002.

Wilson and Nock, "Recent Developments in Protein Microarray Technology", *Angew Chem. Int. Ed. Engl.* 42(5):494-500, 2003.

Winkler, U., et al., "Urinary Protein Patterns for Early Detection of Preeclampsia", Contributions to Nephrology, vol. 68, pp. 227-229, Karger, Basel 1988.

Wu, C., et al., "Role of 14-3-3 proteins in early Xenopus development", *Mech. Dev.*, 119,45-54, 2002.

Yates, et al., Automated Protein Identification Using Microcolumn Liquid Chromatography-Tandem Mass Spectrometry, *Methods Mol. Biol.* 112(2-D):553-569, 1999.

Zhou, H., et al., "Solution and chip arrays in protein profiling", *Trends Biotechnol.*19(10):S34-S39, 2001.

Zhu, et al., "Protein arrays and microarrays", *Current Opin. Chem. Biol.*, 5:40-45, 2001.

Genbank, Accession No. AL121901, Direct Submission, Submitted: Jan. 16, 2007, Wellcome Trust Sanger Institute, Hinxton, Cambridge, CB10 1SA, UK.

Miyano, A, et al., "Differences Among Acute, Subacute, and Chronic Chorioamnionitis Based on Levels of Inflammation-Associated Proteins in Cord Blood," Pediatric and Developmental Pathology, 1(6): 513-521, 1998.

Liebmann, Michael N., "Biomedical Informatics: The Future for Drug Development," Drug Discovery Today, 7(20): S197-S203, 2002.

Lembet, et al., "New rapid bed-side test to predict preterm delivery: phosphorylated insulin-like growth factor binding protein-1 in cervical secretions", Acta Obstet Gynecol Scand, 81: 706-712, (2002).

Cairoli, ct al., "Scrum protein pattern during cow pregnancy: Acute-phase proteins increase in the peripartum period", Electrophoresis, vol. 27, pp. 1617-1625, (2006).

Chu, et al., "Plasma alpha-acid glycoprotein levels in pregnancy", Clinica Chimica, vol. 112, pp. 235-240, (1981).

Gravett M., et al., "Proeomic analysis of cervical-vaginal fluid: identification of novel biomarkers for detection in intra-amniotic infection", Journal of Proteome Research, vol. 6, pp. 89-96, (2007).

Kekki, M., et al., "Insulin-like growth factor binding protein-1 in cervix as a marker of infectious complications in pregnant women with bacterial vaginosis", The Lancet, vol. 353, p. 1494, (1999).

Pereira, L., et al., "Identification of novel protein biomarkers of preterm birth in human cervical-vaginal fluid", Journal of Proteome Research, vol. 6, No. 4, pp. 1269-1276, (2007).

Williams, E., et al., "Clinical evaluation of postpartum vaginal mucus reflects uterine bacterial infection and the immune response in cattle", Theriogenology, vol. 63, pp. 102-117, (2005).

Powers, et al., "Homocysteine and cellular fibronectin are increased in preeclampsia, not transient hypertension of pregnancy", Hypertension in pregnancy, 20(1): 69-77, (2001).

Strevens, "Serum cystatin C is a better marker for preeclampsia than serum creatinine or serum urate", Scand. J. Clin. Invest., 61: 575-580, (2001).

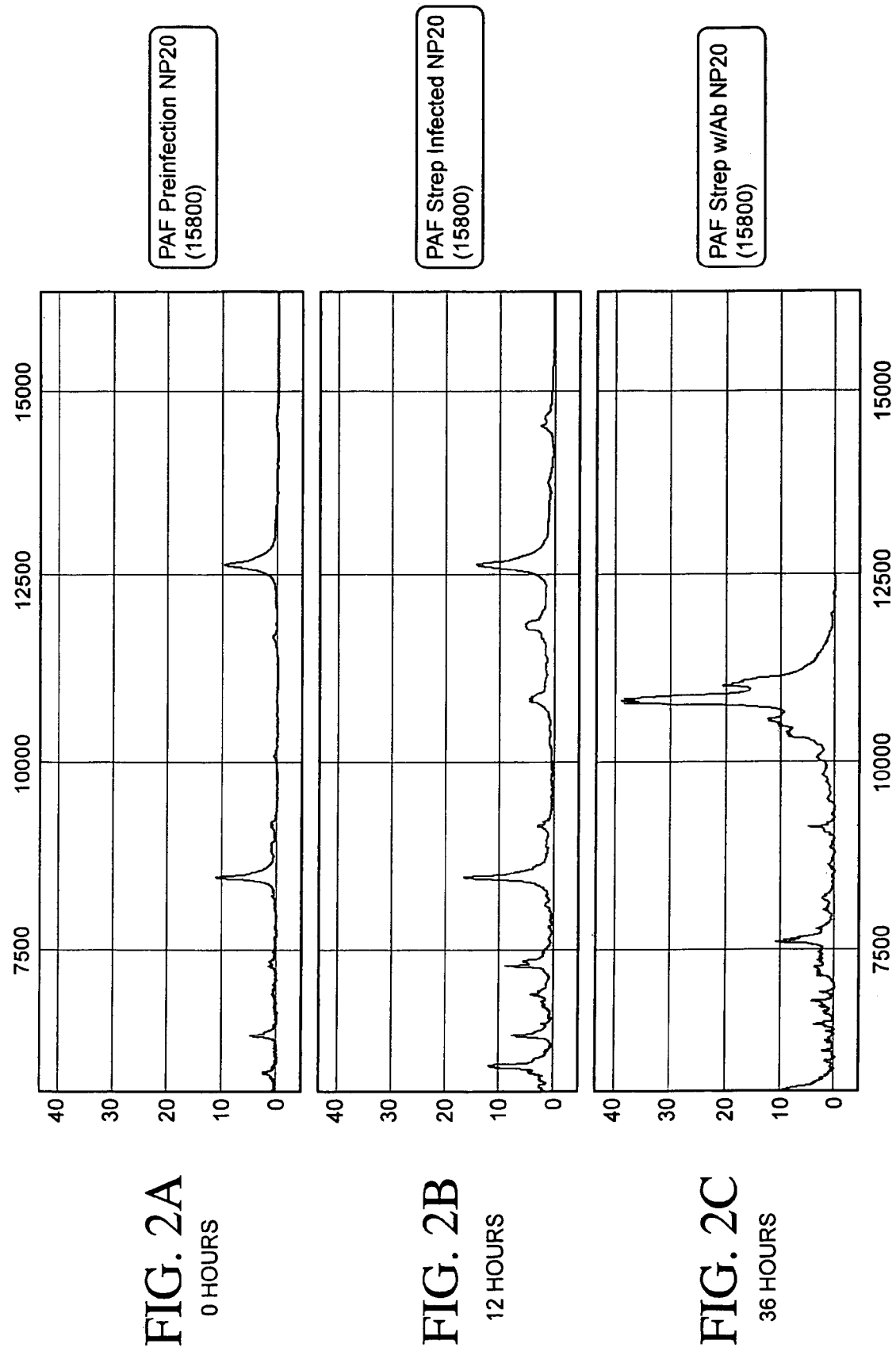

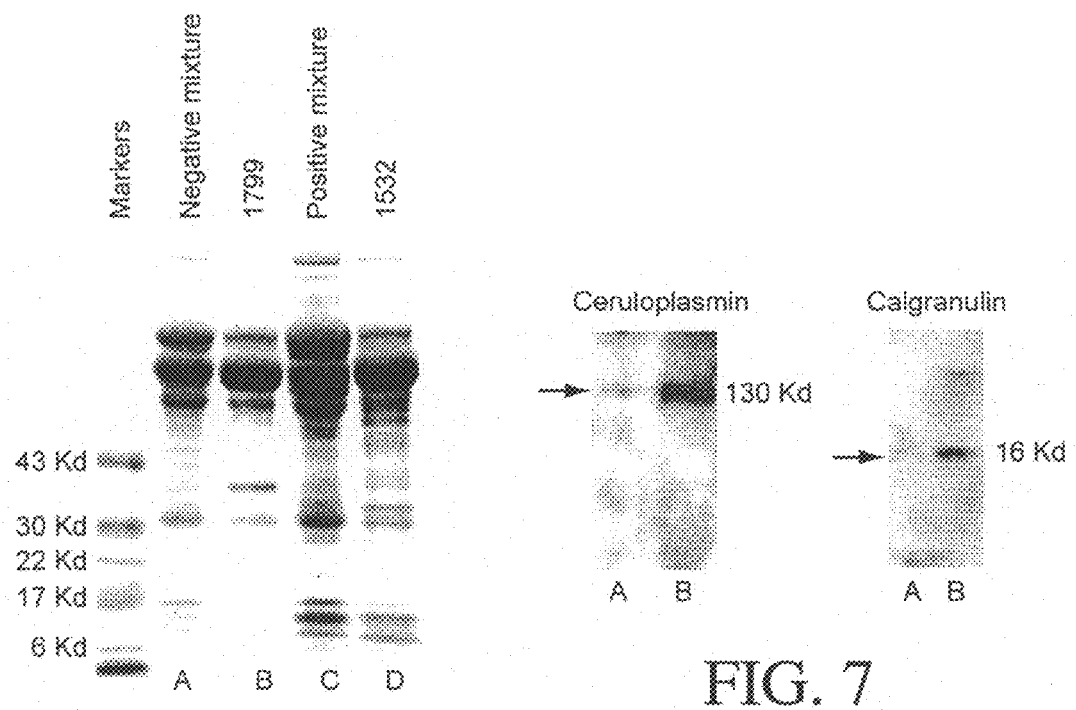
FIG. 5
FIG. 7
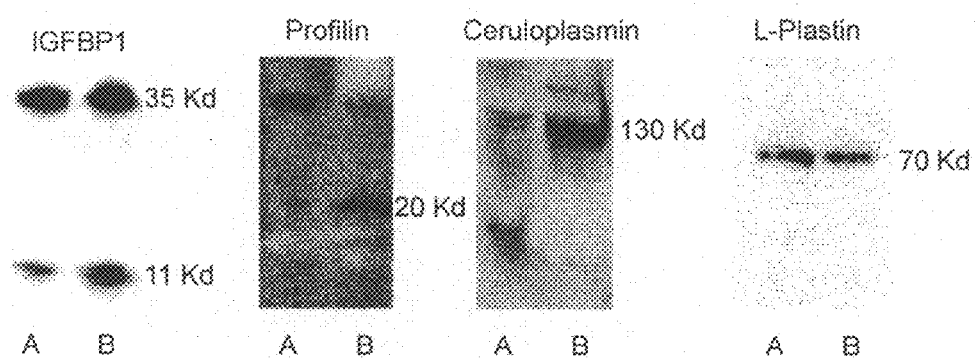
FIG. 6

PRO1_HUMAN (P07737) Profilin I

AGWNAYIDNL MADGTCQDAA IVGYK<u>DSPSV WAAVPGKTFV</u>
<u>NITPAEVGVL VGK</u>DRSSFYV NGLTLGGQKC SVIRDSLLQD
GEFSMDLRTK <u>STGGAPTFNV TVTK</u>TDKTLV LLMGKEGVHG
GLINKKCYEM ASHLRRSQY                                    (SEQ ID NO: 5)

| | | | | | |
|---|---|---|---|---|---|
| (1) PSVWAAA[GP]R | m/z=607.2974 | z=2 | S=8.4 | N=1 | (SEQ ID NO: 6) |
| (2) STGGAPTFNVTVTK | m/z=691.36 | z=2 | S=9.9 | N=1 | (SEQ ID NO: 7) |
| (3) TFVNITPAEVGVLVGK | m/z=823.46 | z=2 | S=9.8 | N=1 | (SEQ ID NO: 8) |
| (4) DSPSVWAAVPGK | m/z=608.31 | z=2 | S=10.0 | N=1 | (SEQ ID NO: 9) |
| (5) DSPSVWAAVPGK | m/z=608.31 | z=2 | S=10.0 | N=1 | (SEQ ID NO: 10) |
| (6) TFVNITPAEVGVLVGK | m/z=823.46 | z=2 | S=9.8 | N=1 | (SEQ ID NO: 11) |

FIG. 11

MSEVPVARVWLVLLLLTVQVGVTAGAPWQCAPCSAEKLA
LCPPVSASCSEVTRSAGCGCCPMCALPLGAACGVATARC
ARGLSCR*alpgeqqplhaltr*GQGACVQESDASAPHAAEAGSP
ESPESTEITEEELLDNFHLMAPSEEDHSILWDAISTYDGSK
<u>ALHVTNIKKWKEPCRIELYRVVESLAKAQETSGEEISKFY</u>
<u>LPNCNKNGFYHSRQCETSMDGEAGLCWCVYPWNGK</u>*rip*
*gspeir*GDPNCQIYFNVQN                                    (SEQ ID NO: 1)

*alpgeqqplhaltr*                                         (SEQ ID NO: 2)

*ripgspeir*                                              (SEQ ID NO: 3)

ALHVTNIKKWKEPCRIELYRVVESLAKAQETSGEEISKFYL
PNCNKNGFYHSRQCETSMDGEAGLCWCVYPWNGK*ripgsp*
*eir*GDPNCQIYFN                                          (SEQ ID NO: 4)

FIG. 12

16b-I (A) Functional classification and (B) subcellular localization of proteins identified in the CVF proteome MALDI-TOF-MS analysis of CVF and AF from control and *Ureaplasma parvum*-infected non-human primates.

Immunodetection of biomarkers for IAI in non-human primate CVF.

FIG. 26
A. Control vs PTB
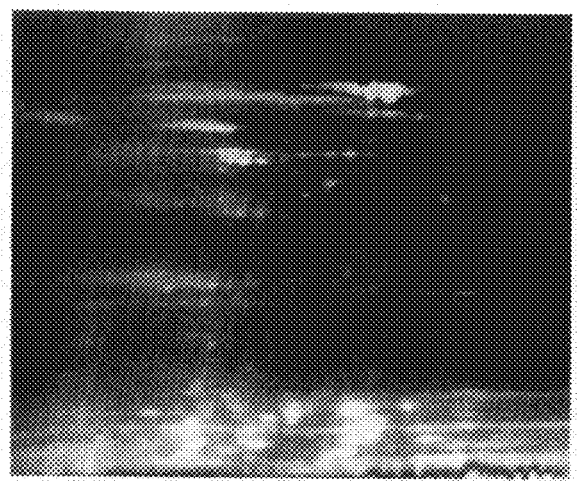
B. Control vs PTL
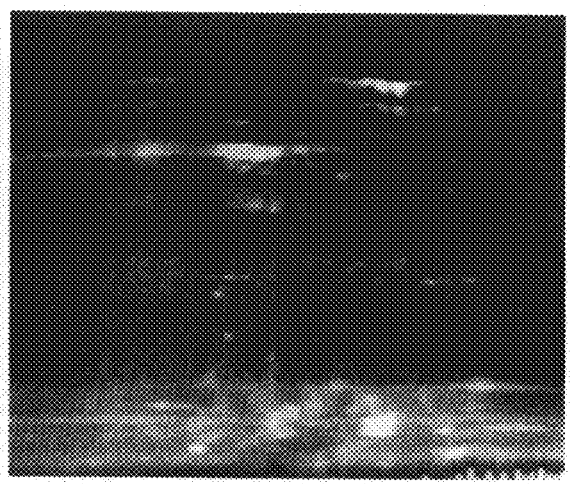
C. PTB vs PTL
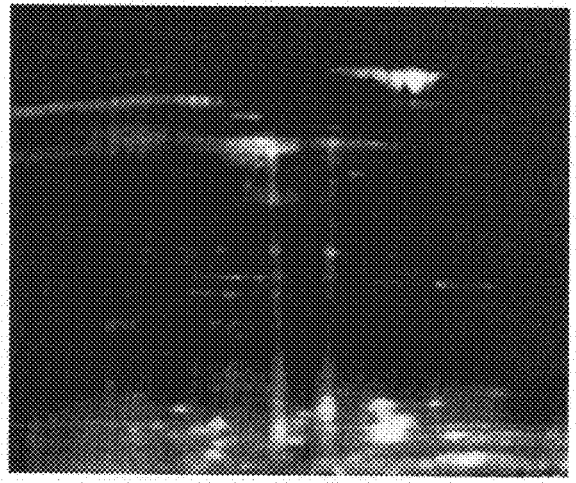
D. PTB vs PTL
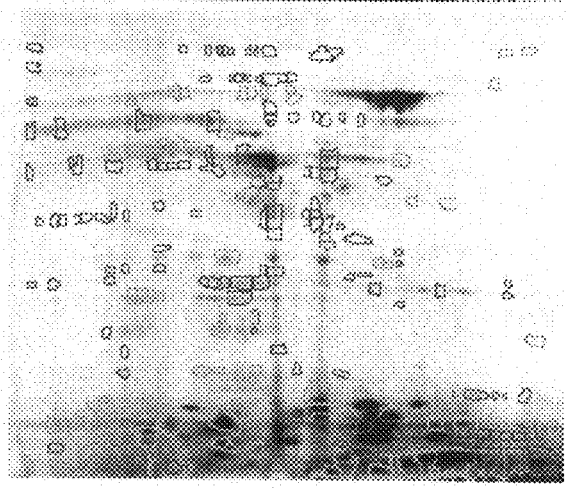

DIAGNOSIS OF INTRA-UTERINE INFECTION BY PROTEOMIC ANALYSIS OF CERVICAL-VAGINAL FLUIDS

CROSS-REFERENCE TO RELATED APPLICATIONS

This application is a continuation-in-part of U.S. patent application Ser. No. 11/473,797 filed Jun. 22, 2006, now abandoned, and U.S. patent application Ser. No. 10/400,005 filed Mar. 25, 2003, now U.S. Pat. No. 7,191,068, which applications are fully incorporated herein by reference.

BACKGROUND OF THE INVENTION

1. Field of the Invention

The invention concerns the identification of proteomes of biological fluids and their use in determining the state of maternal/fetal conditions, including maternal conditions of fetal origin, chromosomal aneuploidies, and fetal diseases associated with fetal growth and maturation. In particular, the invention concerns a comprehensive proteomic analysis of human amniotic fluid (AF) and cervical vaginal fluid (CVF), and the correlation of characteristic changes in the normal proteome with various pathologic maternal/fetal conditions, such as intra-amniotic infection, pre-term labor, and/or chromosomal defects. The invention further concerns the identification of biomarkers and groups of biomarkers that can be used for non-invasive diagnosis of various pregnancy-related disorders, and diagnostic assays using such biomarkers.

2. Description of the Related Art

Proteomics

The large-scale analysis of protein expression patterns is emerging as an important and necessary complement to current DNA cloning and gene profiling approaches (Pandey and Mann, Nature 405:837-46 (2000)). DNA sequence information is helpful in deducing some structural and potential protein modifications based on homology methods, but it does not provide information on regulation of protein function through post-translational modifications, proteolysis or compartmentalization.

Traditional gel-based methods, such as one- and two-dimensional gel electrophoresis are useful for small-scale protein detection (<1,000 proteins), but these require large sample quantity (Lilley K S, Razzaq A, Dupree P: Two-dimensional gel electrophoresis: recent advances in sample preparation, detection and quantitation. Curr Opin Chem Biol. 6(1):46-50, 2002). Approaches to overcome this limitation include matrix-assisted or surface-enhanced laser desorption/ionization (MALDI or SELDI) time-of-flight mass spectrometers that accurately generate profiles showing the masses of proteins in a sample. These patterns or profiles can be used to identify and monitor various diseases. The second level of identification comes from coupling peptide mapping to tandem mass spectrometry to generate amino acid sequence information from peptide fragments. This can, for example, be achieved by coupling the MALDI/SELDI or ESI to quadrupole time-of-flight. MS (Qq-TOF MS). The latter method can also be used for quantification of specific peptides (ICAT technology).

Diagnosis of Pathologic Maternal/Fetal Conditions

There are numerous pathologic maternal and fetal conditions, such as intra-amniotic infection (IAI), preeclampsia, preterm delivery and labor, and chromosomal aneuploidies, that may develop during pregnancy and compromise the well-being or, in some instances, threaten the life of the mother and/or the fetus or newborn. Early diagnosis of such conditions is critical to allow timely treatment and intervention. Unfortunately, early diagnosis for most of these conditions is difficult because the clinical signs and symptoms occur late, and are often non-specific and inconsistent. For example, the clinical symptoms of IAI typically include maternal fever and leukocytosis, but these symptoms often occur later and are neither sensitive nor specific. Thus, Gravett et al., Am. J. Obstet. Gynecol. 171:1660-7 (1994), utilizing a non-human primate model, demonstrated that following experimental intra-amniotic infection with Group B streptococcus, fever and leukocytosis are present only 50% of the time at the onset of infection-induced preterm labor, which occurs 28 to 40 hours after experimental infection. Therefore, to avoid a delay in diagnosis, a high index of suspicion and the appropriate use of adjunctive laboratory tests, are warranted. The clinical criteria commonly used to diagnose IAI include maternal fever. ($\geq 37.8°$ C.), along with two or more of the following: maternal leukocytosis ($\geq 15,000/mm^3$), maternal or fetal tachycardia, uterine tenderness, or foul-smelling amniotic fluid.

Because of the inconsistency of clinical features, other adjunctive laboratory tests have been utilized to aid in the diagnosis of IAI. These include: measurement of maternal C-reactive protein, direct examination of amniotic fluid for leukocytes or bacteria on Gram stain, amniotic fluid culture, measurement of amniotic fluid glucose concentrations, detection of amniotic fluid leukocyte esterase, detection of bacterial organic acids by gas-liquid chromatography, measurements of various amniotic fluid or vaginal cytokines (e.g., interleukins 2, 4, 6, granulocyte colony-stimulating factor, and tumor necrosis factor-$\alpha$), matrix metalloproteinase-9, lactoferrin, and assessment of fetal activity (biophysical profile) by ultrasonography. Measurement of cytokines or other biochemical factors is expensive, generally not clinically available, and is primarily a research tool. Further, the testing efficiency of these tests has not been consistently better than more readily available traditional tests such as amniotic fluid Gram stain and culture, amniotic fluid glucose concentrations, and detection of amniotic fluid leukocyte esterase. The efficiency of these tests has been previously extensively reviewed. (Ohlsson, A. and Wang, E.: An analysis of antenatal tests to detect infection at preterm rupture of the membranes. American Journal of Obstetrics and Gynecology 162:809, 1990). Although all have reasonable sensitivity, specificity, and predictive value none are sufficiently sensitive or specific to be utilized independently of clinical features in the diagnosis of IAI.

Accordingly, there is a great need for new approaches that allow early and accurate diagnosis of IAI and other pathologic maternal/fetal conditions, especially pre-term labor and delivery.

It is particularly desirable to develop new, efficient and reliable non-invasive methods for the diagnosis of chromosomal aneuploidies. At present the definitive diagnosis of chromosomal aneuploidies following maternal serum screening and ultrasound requires a mid-trimester genetic amniocentesis. This is an invasive procedure associated with a 0.5% risk of loss of the pregnancy. Further, chromosomal analysis of amniotic fluid cells is a labor-intensive and time-consuming procedure, taking up to 2 weeks. Reliable tests are therefore necessary to improve the detection of chromosomal aneuploidies from maternal serum, or other biological fluids, reduce the unacceptably high false positive rate of maternal screening, and increase the speed and efficiency of diagnosis from amniotic fluid following amniocentesis. Other pathologic aneuploidic conditions, such as Klinefelter syndrome and Turner syndrome, may be entirely missed by screening with ultrasonography or conventional maternal serum screening.

SUMMARY OF THE INVENTION

The present invention provides non-invasive and sensitive methods for the early diagnosis, prognosis, and monitoring of pathologic fetal/maternal conditions, by proteomic analysis of biological fluids.

The present invention further provides proteomic profiles of biological fluids, such as amniotic fluid and maternal serum, which enable the diagnosis, prognosis, and monitoring of various pathologic fetal/maternal conditions, including, without limitation, intra-amniotic infection (IAI), chromosomal aneuploidies, and fetal diseases associated with fetal growth and maturation. In particular, the present invention provides normal and pathologic proteomic profiles for IAI and chromosomal aneuploidies. The determination of the normal proteomic profile is of great importance, since it enables the elimination of the fetal/maternal condition in question (negative diagnosis), which eliminates the need to subject the patient to unnecessary and potentially dangerous treatment or intervention.

The present invention further provides specific biomarkers, for the presence and state of IAI and chromosomal aneuploidies, which are differentially expressed in biological fluids, such as amniotic fluid or maternal serum, when such pathologic conditions are present.

In one aspect, the invention concerns a method for determining the state of a maternal or fetal condition, comprising comparing the proteomic profile of a test sample of a biological fluid obtained from a mammalian subject with the proteomic profile of a normal sample, or a reference proteomic profile comprising at least one unique expression signature characteristic of such condition.

In an embodiment of this method, the mammalian subject is a pregnant female, preferably primate or human.

In another embodiment, the maternal condition is selected from the group consisting of intrauterine infection, preeclampsia, and preterm labor.

In a further embodiment, the fetal condition is selected from the group consisting of chromosomal aneuploidies, congenital malformation, gestational age and fetal maturity, where the chromosomal aneuploidy can, for example, be Down syndrome, trisomy-13, trisomy-18, Turner syndrome, or Klinefelter syndrome.

Any biological fluid can be used in performing the method of the invention, including, without limitation, amniotic fluid, serum, plasma, urine, cerebrospinal fluid, breast milk, mucus, and saliva, preferably, amniotic fluid or maternal serum.

In a further embodiment, the proteomic profile of the test sample comprises information of at least 2 proteins, or at least 5 proteins, or at least 10 proteins, or at least 20 proteins, or at least 50 proteins.

In a specific embodiment, the proteomic profile is a mass spectrum.

In another embodiment, the mass spectrum comprises at least one unique expression signature in the 3 to 5 kDa range of the mass spectrum.

In yet another embodiment, the mass spectrum comprises at least one unique expression signature in the 10 to 12 kDa range of the mass spectrum.

In a further embodiment, the maternal condition is intra-amniotic infection, and the unique expression signature is an extra peak in the 10 to 11 kDa molecular weight range in the test sample, which is indicative of intra-amniotic infection.

In a different embodiment, the proteomic profile is produced by Western blot analysis.

In another embodiment, the biological fluid is that of a human, and the proteomic profile includes information of the expression of one or more of the proteins selected from the group consisting of: macrophage capping protein, neutrophil gelatinase-associated lipocalin, myeloperoxidase; L-plastin; azurocidin; antibacterial protein FALL-39; Gp340 variant protein; Ebner salivary gland protein homologoue (GenBank™ Accession No. 355392); leukocyte elastase inhibitor; calgranulin A; calgranulin B; cofilin; moesin; profilin I, cronin-like protein p57; annexin II, fibronectin; glia-derived nexin; antithrombin-III; squamous cell carcinoma antigen 1, squamous cell carcinoma antigen 2; serpin 12; cystatin A; cystatin B; cystatin C; IGFBP-1; Vitamin D-binding protein; apolipoprotein A-I; 14-3-3 protein sigma; 14-3-3 protein zeta/delta; gelsolin; lactotransferrin; phosphoglycerate kinase 1; phosphoglycerate mutase 1; and transketolase; or a fragment, precursor, or naturally occurring variant thereof.

In a further embodiment, the proteomic profile includes information of the expression of one or more of the proteins selected from the group consisting of macrophage capping protein; neutrophil gelatinase-associated lipocalin; myeloperoxidase; L-plastin; azurocidin; antibacterial protein FALL-39; leukocyte elastase inhibitor; calgranulin A; calgranulin B; profilin I, glia-derived nexin; serpin 12; cystatin A; and IGFBP-1; or a fragment, precursor, or naturally occurring variant thereof.

The foregoing method is suitable for the diagnosis of various fetal and maternal conditions, including, without limitation, intra-amniotic infection, developmental defects, including defects of an organ system, musculoskeletal deformities, and conditions resulting from chromosomal aneuploidies, such as Down syndrome, trisomy-13, trisomy-18, Turner syndrome, or Klinefelter syndrome.

If the proteomic profile of the test sample is essentially the same as the proteomic profile of the normal sample, the subject is determined to be free of the maternal or fetal condition.

If the proteomic profile contains essentially the same unique expression signature as a diseased sample, the patient is diagnosed with the corresponding material or fetal condition.

In another aspect, the invention concerns a method for the diagnosis of intra-amniotic infection, comprising (a) comparing the proteomic profile of a test sample of a biological fluid obtained from a pregnant female mammal with the proteomic profile of a normal sample, or a reference proteomic profile, wherein the proteomic profiles provide information of the mass of the proteins present in the samples, or the proteolytic fragments thereof; and (b) diagnosing the mammal with intra-amniotic infection if the proteomic profile of the test sample shows a unique expression signature in the 3-5 and/or 10-12 KDa molecular weight range.

In a further aspect, the invention concerns a method for the diagnosis of intra-amniotic infection, comprising:

(a) comparing the proteomic profile of a test sample of a biological fluid obtained from a pregnant female mammal with the proteomic profile of a normal sample; and (b) diagnosing the mammal with intra-amniotic infection if at least one protein selected from the group consisting of IGFB-1, profilin, ceruloplasmin, L-plastin, and calgraulin, or a fragment, precursor or naturally occurring variant thereof, is differentially expressed in the test sample relative to the normal sample.

In a particular embodiment, at least one of IGFBP-1, profilin, ceruloplasmin, and calgranulin, or a fragment, precursor, or naturally-occurring variant thereof, is overexpressed in the test sample relative to the normal sample.

In another embodiment, L-plastin is underexpressed in the test sample relative to the normal sample.

In yet another embodiment, the presence of IGFBP-1 is detected by identifying the proteolytic fragment shown in FIG. 12, or a fragment thereof.

In another aspect, the invention concerns a method for the diagnosis of a chromosomal aneuploidy, comprising:

(a) comparing the proteomic profile of a test sample of a biological fluid obtained from a pregnant female mammal with the proteomic profile of a normal sample, or a reference proteomic profile, wherein the proteomic profiles provide information of the mass of the proteins present in the samples, or the proteolytic fragments thereof; and (b) diagnosing the mammal with the chromosomal aneuploidy if the proteomic profile of the test sample shows a unique expression signature in the 4 to 15 KDa molecular weight range.

In a different aspect, the invention concerns a method for the diagnosis of a developmental defect of a fetus, comprising:

(a) comparing the proteomic profile of a test sample of a biological fluid obtained from a pregnant female mammal with the proteomic profile of a normal sample, or a reference proteomic profile; and (b) confirming the presence of the developmental defect if at least one actin-modulating protein, or a fragment, precursor, or naturally occurring variant thereof, is differentially expressed in the test sample relative to the normal sample.

In a particular embodiment of this method, the actin-modulating protein is selected from the group consisting of moesin, p57, gelsolin, and a 14-3-3 protein.

In a further aspect, the invention concerns a method for the diagnosis of a maternal or fetal infection or immune-response related disorder, comprising:

(a) comparing the proteomic profile of a test sample of a biological fluid obtained from a pregnant female mammal with the proteomic profile of a normal sample, or a reference proteomic profile; and (b) confirming the presence of the maternal or fetal infection or immune-response related disorder, if at least one protein selected from the group consisting of macrophage capping protein (MCP), leukocyte elastase, neutrophil gelatinase-associated lipcalcin (NGAL), myeloperoxidase, L-plastin, calgranulin, FALL-39, azyrocidin (CAP37), proteases and protease inhibitors, is differentially expressed in the test sample relative to the normal sample.

In a still further aspect, the invention concerns a method for the diagnosis of neonatal sepsis, comprising detecting in the proteomic profile of a biological fluid obtained from a pregnant females mammal the presence of Gp-340.

In yet another aspect, the invention concerns a proteomic profile of a biological fluid comprising information of one or more proteins selected from the group consisting of macrophage capping protein, neutrophil gelatinase-associated lipocalin, myeloperoxidase; L-plastin; azurocidin; antibacterial protein FALL-39; Gp340 variant protein; Ebner salivary gland protein homologoue (GenBank™ Accession No. 355392); leukocyte elastase inhibitor; calgranulin A; calgranulin B; cofilin; moesin, profilin I, cronin-like protein p57; annexin II, fibronectin; glia-derived nexin; antithrombin-III; squamous cell carcinoma antigen 1, squamous cell carcinoma antigen 2; serpin 12; cystatin A; cystatin B; cystatin C; IGFBP-1; Vitamin D-binding protein; apolipoprotein A-I; 14-3-3 protein sigma; 14-3-3 protein zeta/delta; gelsolin; lactotransferrin; phosphoglycerate kinase 1; phosphoglycerate mutase 1; and transketolase; or a fragment, precursor, or naturally occurring variant thereof.

In a further aspect, the invention concerns a proteomic profile of a biological fluid comprising information of one or more proteins selected from the group consisting of macrophage capping protein; neutrophil gelatinase-associated lipocalin; myeloperoxidase; L-plastin; azurocidin; antibacterial protein FALL-39; leukocyte elastase inhibitor; calgranulin A; calgranulin B; profilin I, glia-derived nexin; serpin 12; cystatin A; and IGFBP-1; or a fragment, precursor, or naturally occurring variant thereof.

The invention further concerns a proteomic profile of a biological fluid characteristic of intra-amniotic infection, comprising information confirming the presence of a protein selected from the group consisting of IGFB-1, profilin, ceruloplasmin, L-plastin, and calgraulin.

In another aspect, the invention concerns a proteomic profile of a biological fluid characteristic of intra-amniotic infection represented in a form providing information of the molecular weight of proteins present in the biological fluid, or the proteolytic fragments thereof, comprising a unique expression signature in the 3-5 KDa and/or 10-12 KDa molecular weight range.

In a further aspect, the invention concerns the proteomic profile essentially as shown in any one of FIGS. 1A-1C, or essentially as shown in any one of FIGS. 2A-C, or essentially as shown in any one of FIGS. 3A-C, or essentially as shown in FIG. 4A or 4B, or essentially as shown in any one of FIGS. 6-10.

In a particular embodiment, the proteomic profile is analyzed in a microarray format.

In another aspect, the invention concerns a method for determining the presence of intra-uterine infection in a pregnant female mammalian subject comprising:

(a) testing in a sample of cervical-vaginal fluid obtained from said subject the abundance of two or more proteins selected from the group consisting of haptoglobin precursor (Swiss-Prot™ Acc. No. P00738); alpha-1-acid glycoprotein (Swiss-Prot™ Acc. No. P02763), fatty acid-binding protein, epidermal (Swiss-Prot™ Acc. No. Q01469), and insulin-like growth factor binding protein (Swiss-Prot™ Acc. No. P08833) relative to the abundance in normal cervical fluid or cervical fluid known to be indicative of intra-uterine infection; and (b) concluding that intra-uterine infection is present if said abundance shows a statistically significant difference relative to abundance in said normal cervical fluid, or does not show a statistically significant difference relative to abundance in said cervical fluid known to be indicative of intra-uterine infection. The mammalian subject preferably is human. In various embodiments, the abundance of at least three, or all four of the listed proteins is tested.

In another embodiment, the method may include testing the abundance of one or more additional proteins, selected from the group consisting of profilin-1 (Swiss-Prot™ Acc. No. P07737); serum albumin precursor (Swiss-Prot™ Acc. No. P2768); calgranulin B (Swiss-Prot™ Acc. No. P06702); and squamous cell carcinoma antigen 1 (Swiss-Prot™ Acc. No. P29508).

In yet another embodiment, the abundance of at least one additional protein selected from the following group is tested: alpha-1-antitrypsin precursor (Swiss-Prot™ Acc. No. P01009); fibronectin precursor (Swiss-Prot™ Acc. No.

P02751); Annexin A2 (Swiss-Prot™ Acc. No. P07355); Vitamin-D binding protein precursor (Swiss-Prot™ Acc. No. P0$_{2774}$).

In a further embodiment, the abundance of at least one additional protein selected from the following group is tested: cystatin A (Swiss-Prot™ Acc. No. P01040); mucin-5B precursor (Swiss-Prot™ Acc. No. Q9HC84); small proline-rich protein 3 (Swiss-Prot™ Acc. No. Q9UBC9); lysozyme C precursor (Swiss-Prot™ Acc. No. P61626); and serotransferrin precursor (P02787).

The abundance of such proteins can be determined by any method known in the art, such as, for example, by an immunoassay, mass spectrometry, or using protein arrays.

If a further aspect, the invention concerns a method for determining the likelihood of pre-term delivery in a pregnant female mammalian subject presenting with symptoms of pre-term labor, comprising (a) testing in a sample of cervical-vaginal fluid obtained from the subject the abundance of two or more proteins selected from the group consisting of haptoglobin precursor (Swiss-Prot™ Acc. No. P00738); alpha-1-acid glycoprotein 1 (Swiss-Prot™ Acc. No. P02763), fatty acid-binding protein, epidermal (Swiss-Prot™ Acc. No. Q01469), and insulin-like growth factor binding protein (Swiss-Prot™ Acc. No. P08833) relative to the abundance in normal cervical fluid or cervical fluid known to be indicative of intra-uterine infection; and (b) predicting the occurrence of pre-term delivery if the abundance shows a statistically significant difference relative to abundance in said normal cervical fluid, or does not show a statistically significant difference relative to abundance in the cervical fluid known to be indicative of intra-uterine infection.

Just as in the previous aspect, the method may include testing of the abundance of one or more additional proteins, such as those listed above.

In a further embodiment, if the occurrence of pre-term delivery cannot be predicted based upon testing conducted as described above, the subject is further tested for the abundance of fibronectin precursor (Swiss-Prot™ Acc. No. P02751), wherein if such abundance shows a statistically significant difference relative to abundance in the normal cervical fluid, the occurrence of pre-term delivery is predicted.

In a specific embodiment, the abundance of fibronectin precursor (Swiss-Prot™ Acc. No. P02751) is determined prior to step (a).

In a further aspect, the invention concerns an immunoassay kit comprising antibodies and reagents for the detection of two or more proteins selected from the group consisting of haptoglobin precursor (Swiss-Prot™ Acc. No. P00738); alpha-1-acid glycoprotein 1 (Swiss-Prot™ Acc. No. P$_{02763}$); fatty acid-binding protein, epidermal (Swiss-Prot™ Acc. No. Q01469); and insulin-like growth factor binding protein (Swiss-Prot™ Acc. No. P08833).

In one embodiment, the above immunoassay kit additionally comprises antibodies and reagents for the detection of at least one protein selected from the group consisting of profilin-1 (Swiss-Prot™ Acc. No. P07737); serum albumin precursor (Swiss-Prot™ Acc. No. P2768); calgranulin B (Swiss-Prot™ Acc. No. P06702); squamous cell carcinoma antigen 1 (Swiss-Prot™ Acc. No. P29508); alpha-1-antitrypsin precursor (Swiss-Prot™ Acc. No. P01009); fibronectin precursor (Swiss-Prot™ Acc. No. P02751); Annexin A2 (Swiss-Prot™ Acc. No. P07355); Vitamin-D binding protein precursor (Swiss-Prot™ Ace. No. P02774); cystatin A (Swiss-Prot™ Acc. No. P01040); mucin-5B precursor (Swiss-Prot™ Acc. No. Q9HC84); small proline-rich protein 3, (Swiss-Prot™ Acc. No. Q9UBC9); lysozyme C precursor (Swiss-Prot™ Acc. No. P61626); and serotransferrin precursor (P02787); cystatin A (Swiss-Prot™ Acc. No. P01040); mucin-5B precursor (Swiss-Prot™ Acc. No. Q9HC84); small proline-rich protein 3 (Swiss-Prot™ Acc. No. Q9UBC9); and lysozyme C precursor (Swiss-Prot™ Acc. No. P61626); and serotransferrin precursor (P02787).

BRIEF DESCRIPTION OF THE DRAWINGS

The file of this patent contains at least one drawing executed in color. Copies of this patent with color drawing(s) will be provided by the Patent and Trademark Office upon request and payment of the necessary fees.

FIGS. 2A-C. Time course analyses of the primate amniotic fluid in response to infection (GBS). Amniotic fluid was collected before the inoculation of bacteria and serially after infection and subjected to SELDI-TOF analysis as described below. FIGS. 2A: before infection; 2B: 12 hours after infection; 2C: 36 hours after infection.

FIG. 5. SDS-PAGE Commassie Blue stained gel. A) 4 human control AF samples pooled; B) individual control AF sample; C) 4 human infected AF samples pooled; D) individual infected AF sample.

FIG. 6. Detection of differential protein expression in the human amniotic fluid. A) Control AF sample (pooled); B) Infected AF sample (pooled).

FIG. 7. Detection of differential protein expression in the human amniotic fluid. A) Control AF sample (pooled); B) Infected AF sample (pooled).

FIG. 11. Schematic representation of de novo protein sequence identification of amniotic fluid proteins. PRO1_HUMAN (P07737) Profilin I (SEQ ID Nos: 5-11).

FIG. 12. IGFBP-1 de novo protein identification and proteolytic fragment sequence. (SEQ ID NO: 1). The peptide sequences found in samples 0426se_H1_12 and 0425se_H1_13 with the Ms/MS are shown in lower case. (SEQ ID Nos: 2 and 3. These came from infected amniotic fluid when run on 1-D gel bands that were trypsin digested and subjected to MS/MS analysis. The proteolytic fragment of IGF-BP-1 detected in 1-D dels (low molecular weight range, FIG. 5), Western blots (FIG. 6) and MS/MS analysis (FIG. 13) of trypsin-digested ~10.5 to 12 KDa band from infected amniotic fluid is represented in the region of the underlined sequence. (SEQ ID NO: 4).

FIG. 26. 2D DIGE analysis of PTL, PTB, and control CVF samples. A. Overlay of PTB (green) and control (red), (B) PTL (green) and control (red), and (C) PTB (green) and PTL (red). D. Map of the differentially abundant proteins between PTB and PTL. (D) Differential spot map of panel C. Spots outlined in green represent >2-fold higher in PTB and those in red represent >2-fold lower in PTB with respect to PTL. The spot map was generated by Phoretix Evolution. Proteins identified are numbered and shown in Table 9.

DETAILED DESCRIPTION OF THE PREFERRED EMBODIMENT

I. Definitions

Figure 1A:
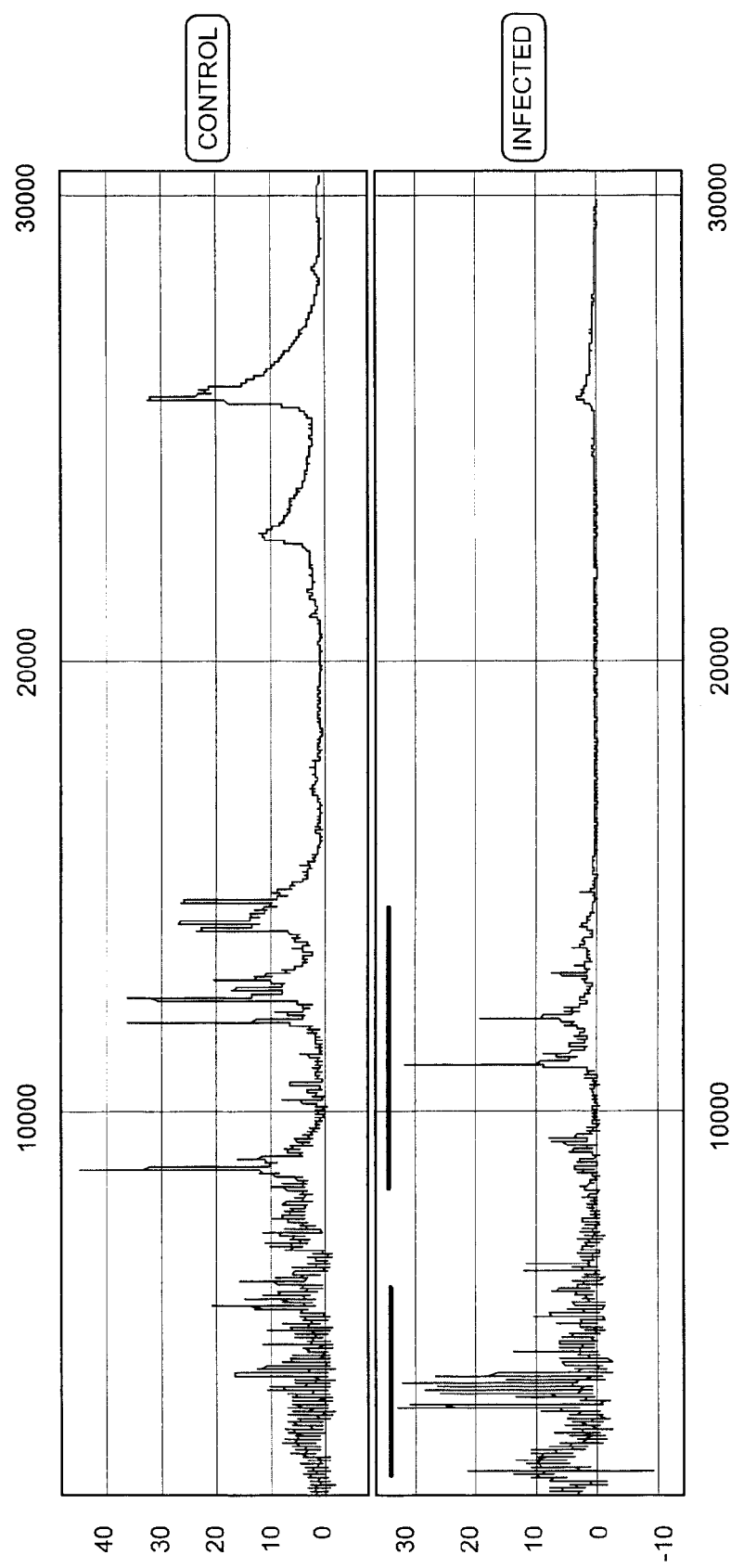
FIGS. 1A-C. Infection-induced differential protein expression in the primate amniotic fluid. SELDI-TOF analysis of amniotic fluid extracts bound to chemically defined Normal Phase chip arrays. A). Whole spectrum collected at 235 laser intensity showing the differences in the peak intensities. B) Detailed spectrum showing the differences in the 10 to 12 KDa region between control and infected. C) Detailed spectrum showing the differences in the 3-5 KDa region between control and infected. Solid lines were used to show the significant differences in expression (unique expression signatures) which could be used to develop diagnostic tests.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994) provides one skilled in the art with a general guide to many of the terms used in the present application.

The term "proteome" is used herein to describe a significant portion of proteins in a biological sample at a given time. The concept of proteome is fundamentally different from the genome. While the genome is virtually static, the proteome continually changes in response to internal and external events.

The term "proteomic profile" is used to refer to a representation of the expression pattern of a plurality of proteins in a biological sample, e.g. a biological fluid at a given time. The proteomic profile can, for example, be represented as a mass spectrum, but other representations based on any physicochemical or biochemical properties of the proteins are also included. Thus the proteomic profile may, for example, be based on differences in the electrophoretic properties of proteins, as determined by two-dimensional gel electrophoresis, e.g. by 2-D PAGE, and can be represented, e.g. as a plurality of spots in a two-dimensional electrophoresis gel. Differential expression profiles may have important diagnostic value, even in the absence of specifically identified proteins. Single protein spots can then be detected, for example, by immunoblotting, multiple spots or proteins using protein microarrays. The proteomic profile typically represents or contains information that could range from a few peaks to a complex profile representing 50 or more peaks. Thus, for example, the proteomic profile may contain or represent at least 2, or at least 5 or at least 10 or at least 15, or at least 20, or at least 25, or at least 30, or at least 35, or at least 40, or at least 45, or at least 50, or at least 60, or at least 65, or at least 70, or at least 75, or at least 80, or at least 85, or at least 85, or at least 90, or at least 95, or at least 100, or at least 125, or at least 150, or at least 175, or at least 200 proteins.

The term "pathologic condition" is used in the broadest sense and covers all changes and phenomena that compromise the well-being of a subject. Pathologic maternal conditions include, without limitation, intra-amniotic infection, conditions of fetal or maternal origin, such as, for example preeclampsia, and preterm labor and delivery. Pathologic fetal conditions include, without limitation, chromosomal defects (aneuploidies), such as Down syndrome, and all abnormalities in gestational age and fetal maturity.

The term "state of a pathologic [maternal or fetal] condition" is used herein in the broadest sense and refers to the absence, presence, extent, stage, nature, progression or regression of the pathologic condition.

The term "unique expression signature" is used to describe a unique feature or motif within the proteomic profile of a biological sample (e.g. a reference sample) that differs from the proteomic profile of a corresponding normal biological sample (obtained from the same type of source, e.g. biological fluid) in a statistically significant manner.

The terms "intra-amniotic infection (IAI)," "amniotic fluid infection," "amnionitis," and "clinical chorioamnionitis" are used interchangeably, and refer to an acute infection, including, but not restricted to bacterial, of the amniotic fluid and intrauterine contents during pregnancy.

"Patient response" can be assessed using any endpoint indicating a benefit to the patient, including, without limitation, (1) inhibition, at least to some extent, of the progression of a pathologic condition, (2) prevention of the pathologic condition, (3) relief, at least to some extent, of one or more symptoms associated with the pathologic condition; (4) increase in the length of survival following treatment; and/or (5) decreased mortality at a given point of time following treatment.

The term "treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Congenital malformation" is an abnormality which is non-hereditary but which exists at birth.

The designation of any particular protein, as used herein, includes all fragments, precursors, and naturally occurring variants, such as alternatively spliced and allelic variants and isoforms, as well as soluble forms of the protein named, along with native sequence homologs (including all naturally occurring variants) in other species. Thus, for example, when it is stated that the abundance of haptoglobin precursor (Swiss-Prot™ Acc. No. P00738) is tested, the statement specifically includes testing any fragments, precursors, or naturally occurring variant of the protein listed under Swiss-Prot™ Acc. No. P00738, as well as its non-human homologs and naturally occurring variants thereof, if subject is non-human.

II. Detailed Description

The present invention concerns methods and means for an early, reliable and non-invasive testing of maternal and fetal conditions based upon the proteomic profile of a biological fluid of the mother or fetus. The invention utilizes proteomics techniques well known in the art, as described, for example, in the following textbooks, the contents of which are hereby expressly incorporated by reference: *Proteome Research: New Frontiers in Functional Genomics (Principles and Practice)*, M. R. Wilkins et al., eds., Springer Verlag, 1007; *2-D Proteome Analysis Protocols*, Andrew L Link, editor, Humana Press, 1999; *Proteome Research: Two-Dimensional Gel Electrophoresis and Identification Methods (Principles and Practice)*, T. Rabilloud editor, Springer Verlag, 2000; *Proteome Research: Mass Spectrometry (Principles and Practice)*, P. James editor, Springer Verlag, 2001; *Introduction to Proteomics*, D. C. Liebler editor, Humana Press, 2002; *Proteomics in Practice: A Laboratory Manual of Proteome Analysis*, R. Westermeier et al., eds., John Wiley & Sons, 2002.

One skilled in the art will recognize many methods and materials similar or equivalent to those described herein, which could be used in the practice of the present invention. Indeed, the present invention is in no way limited to the methods and materials described.

1. Identification of Proteins and Polypeptides Expressed in Biological Fluids According to the present invention, proteomics analysis of biological fluids can be performed using a variety of methods known in the art.

Typically, protein patterns (proteome maps) of samples from different sources, such as normal biological fluid (normal sample) and a test biological fluid (test sample), are compared to detect proteins that are up- or down-regulated in a disease. These proteins can then be excised for identification and full characterization, e.g. using peptide-mass fingerprinting and/or mass spectrometry and sequencing methods, or the normal and/or disease-specific proteome map can be used directly for the diagnosis of the disease of interest, or to confirm the presence or absence of the disease.

In comparative analysis, it is important to treat the normal and test samples exactly the same way, in order to correctly represent the relative abundance of proteins, and obtain accurate results. The required amount of total proteins will depend on the analytical technique used, and can be readily determined by one skilled in the art. The proteins present in the biological samples are typically separated by two-dimensional gel electrophoresis (2-DE) according to their pI and molecular weight. The proteins are first separated by their charge using isoelectric focusing (one-dimensional gel electrophoresis). This step can, for example, be carried out using immobilized pH-gradient (IPG) strips, which are commercially available. The second dimension is a normal SDS-PAGE analysis, where the focused IPG strip is used as the sample. After 2-DE separation, proteins can be visualized with conventional dyes, like Coomassie Blue or silver staining, and imaged using known techniques and equipment, such as, e.g. Bio-Rad GS800 densitometer and PDQUEST software, both of which are commercially available. Individual spots are then cut from the gel, destained, and subjected to tryptic digestion. The peptide mixtures can be analyzed by mass spectrometry (MS). Alternatively, the peptides can be separated, for example by capillary high pressure liquid chromatography (HPLC) and can be analyzed by MS either individually, or in pools.

Mass spectrometers consist of an ion source, mass analyzer, ion detector, and data acquisition unit. First, the peptides are ionized in the ion source. Then the ionized peptides are separated according to their mass-to-charge ratio in the mass analyzer and the separate ions are detected. Mass spectrometry has been widely used in protein analysis, especially since the invention of matrix-assisted laser-desorption ionisation/time-of-flight (MALDI-TOF) and electrospray ionisation (ESI) methods. There are several versions of mass analyzer, including, for example, MALDI-TOF and triple or quadrupole-TOF, or ion trap mass analyzer coupled to ESI. Thus, for example, a Q-Tof-2 mass spectrometer utilizes an orthogonal time-of-flight analyzer that allows the simultaneous detection of ions across the full mass spectrum range. For further details see, e.g. Chernusevich et al., *J. Mass Spectrom.* 36:849-865 (2001).

If desired, the amino acid sequences of the peptide fragments and eventually the proteins from which they derived can be determined by techniques known in the art, such as certain variations of mass spectrometry, or Edman degradation.

2. Fetal-Maternal Conditions Benefiting from Early and Non-Invasive Diagnosis Intra-Amniotic Infection Intra-amniotic infection (IAI) is an acute bacterial infection of the amniotic fluid and intrauterine contents during pregnancy. Prospective studies indicate that IAI occurs in 4% to 10% of all deliveries (Newton, E. R., Prihoda, T. J., and Gibbs, R. S.: Logistic regression analysis of risk factors for intra-amniotic infection. *Obstet. Gynecol.* 73:571, 1989; Soper, D. E., Mayhall, C. G., and Dalton, H. P.: Risk factors for intraamniotic infection: a prospective epidemiologic study. *American Journal of Obstetrics and Gynecology* 161: 562, 1989; and Lopez-Zeno, J. A., Peaceman, A. M., Adashek, J. A., and Socol, M. L.: A controlled trial of a program for the active management of labor. *N. Engl. J. Med.* 326:450, 1992). Other terms used to describe IAI include amniotic fluid infection, amnionitis, and clinical chorioamnionitis. Intra-amniotic infection is clinically diagnosed by maternal fever, uterine tenderness, leukocytosis, and fetal tachycardia and should be distinguished from histologic chorioamnionitis. Intra-amniotic infection is an important cause of maternal and neonatal morbidity. Intra-amniotic infection accounts for 10-40% of cases of febrile morbidity in the peripartum period and is associated with 20-40% of cases of early neonatal sepsis and pneumonia (Newton, E. R.: Chorioamnionitis and intraamniotic infection. *Clin. Obstet. Gynecol.* 36:795, 1993). Maternal bacteremia occurs in 2-6% of patients with IAI and postpartum infectious morbidity is increased. There is also an increased risk of dysfunctional labor and cesarean delivery among patients with IAI. Duff et al. reported a 75% incidence of dysfunctional labor and a 34% incidence of cesarean delivery among patients who developed intra-amniotic infection while in labor (Duff, P., Sanders, R., and Gibbs, R. S.: The course of labor in term pregnancies with chorioamnionitis. *American Journal of Obstetrics and Gynecology* 147:391, 1983). Intra-amniotic infection is also associated with increased neonatal morbidity and mortality, particularly among preterm neonates. In general, there is a three to four-fold increase in perinatal mortality among low birth weight neonates born to mothers with IAI (Gibbs, R. S., Castillo, M. A., and Rodgers, P. J.: Management of Acute Chorioamnionitis. *American Journal of Obstetrics and Gynecology* 136:709, 1980; Gilstrap, L. C., III, Leveno, K. J., Cox, S. M., Burris, J. S., Mashburn, M., and Rosenfeld, C. R.: Intrapartum treatment of acute chorioamnionitis: impact on neonatal sepsis. *Am. J. Obstet. Gynecol.* 159:579, 1988). There are also increases in respiratory distress syndrome, intraventricular hemorrhage, and neonatal sepsis Morales, W. J.: The effect of chorioamnionitis on the developmental outcome of preterm infants at one year. *Obstetrics and Gynecology* 70:183, 1987). Recently, IAI has been implicated in neonatal periventricular leukomalacia and cerebral palsy; the risks of cerebral white matter damage and cerebral palsy are nine-fold greater in the setting of intra-amniotic infection Bejar, R., Wozniak, P., Allard, M., Benirschke, K., Vaucher, Y., Coen, R., Berry, C., Schragg, P., Villegas, I., and Resnik, R.: Antenatal origin of neurologic damage in newborn infants. I. Preterm infants. *Am. J. Obstet. Gynecol.* 159: 357, 1988; Grether, J. K. and Nelson, K. B.: Maternal infection and cerebral palsy in infants of normal birth weight. *JAMA* 278:207, 1997). Finally, subclinical IAI has been found in at least 10% of women in preterm labor with intact fetal membranes, suggesting that IAI is an important, and potentially preventable, cause of prematurity (Romero, R., Avila, C., Brekus, C. A., and Morotti, R.: The role of systemic and intrauterine infection in preterm parturition. *Annals of the New York Academy of Sciences* 622:355, 1991). A literature review by Newton demonstrated incidences of clinical IAI of 41% at gestational ages less than 27 weeks, 15% at gestational ages of 27'-37 weeks, and 2% at gestations of 38 weeks or greater (Newton et al., supra). Bacteria indigenous to the lower genital tract have also been recovered from the amniotic fluid of 10-20% of all women in preterm labor with intact fetal membranes without clinical signs of intraamniotic infection (Romero et al., supra), and in up to 67% of women in preterm labor with pregnancies ending at 23-24 weeks (Watts, D. H., Krohn, M. A., Hillier, S. L., and Eschenbach, D. A.: The association of occult amniotic fluid infection with gestational age and neonatal outcome among women in preterm labor. *Obstet Gynecol* 79:351, 1992). Most of these patients deliver rapidly, and clinically apparent IAI develops in many. These observations support the hypothesis that ascending, initially subclinical intrauterine infections precede preterm labor and may be an important cause of extreme preterm deliveries.

Preeclampsia

Preeclampsia, defined as maternal hypertension accompanied by proteinuria, edema, or both, occurs in 7% of pregnancies not terminating in the first trimester. Although the cause is unknown, it is more common in extremes of age in childbearing, maternal diabetes, pregnancies with multiple gestations, and pre-existing maternal renal disease and or hypertension. Preeclampsia is associated with increases in perinatal mortality, and may also lead to eclampsia, characterized by maternal seizures and increased maternal mortality. Currently the mainstay of therapy for preeclampsia is delivery and anticonvulsant prophylaxis with magnesium sulfate. Prior to the advent of magnesium sulfate therapy, the observed maternal mortality was 20-30%. However, with prompt diagnosis, allowing anticonvulsant therapy with magnesium sulfate, anti-hypertensives, and delivery the maternal mortality has been reduced to near zero.

Unfortunately, the diagnosis of preeclampsia based upon commonly recognized symptoms and signs is frequently difficult, and occurs late in the course of the disease. Frequently fetal compromise in growth or well-being is the first recognized manifestation of preeclampsia. Laboratory markers for preeclampsia include quantitation of proteinuria, and elevated serum concentrations of uric acid or creatinine. There are no currently available serum markers for early preeclampsia or markers which identify women which will develop preeclampsia. Recently prospective serum markers including leptin and uric acid have been associated with subsequent preeclampsia in one study (Gursoy T, et al. Preeclampsia disrupts the normal physiology of leptin.: Am J Perinatol. 19(6):303-10, 2002) but much work is needed to confirm these findings. Development of early and reliable markers for preeclampsia is imperative to allow for therapy and intervention to optimize the outcome for the neonate and mother.

Preterm Labor and Delivery

Preterm delivery is defined as birth prior to the 37$^{th}$ completed week of gestation. The incidence of preterm birth in the United States is 10-11% of all live births, and is increasing despite aggressive treatment of preterm labor. Overall, prematurity and its consequences are responsible for 80% of perinatal deaths not attributable to congenital malformations and add approximately $5 billion annually to the national health care budget. Risk factors for preterm birth include non-white race, young age, low socioeconomic status, maternal weight below 55 kg, nulliparity, 1$^{st}$ trimester bleeding, multiple gestations (Meis P J, Michielutte R, Peters T J, et al. Factors associated with preterm birth in Cardiff, Wales: II. Indicated and spontaneous preterm birth. *Am J Obstet Gynecol* 173:597-602, 1995).

Unfortunately the prediction of patients at risk for spontaneous preterm birth has been generally disappointing (Creasy R K, Iams J D. Preterm labor and delivery. In *Maternal-Fetal Medicine*, Creasy R K, Resnik R (eds.). W.B. Saunders Company, Philadelphia, Pa. 4$^{th}$ edition, 1999. Pages 498-531). Previous attempts at defining the population at greatest risk for preterm birth, and thereby potentially benefiting from early intervention have included risk-scoring indices, biochemical detection of cervical fetal fibronectin, ultrasound measurement of cervical length, and home uterine activity monitoring. These programs have been both costly, and have been hampered by the inability to predict with accuracy which patients might benefit from early intervention or prophylaxis. All suffer from poor positive predictive value of approximately 30%, with the majority of patients identified as "at risk" delivering at term. Interventions, including pharmacologic treatment to inhibit uterine contractions, are efficacious, but depend upon the early and reliable diagnosis of preterm labor. Early and reliable markers to identify patients at greatest risk for preterm birth are therefore necessary to reduce the tremendous costs and neonatal mortality and morbidity associated with preterm birth.

Chromosomal Aneuploidies

Chromosomal abnormalities are a frequent cause of perinatal morbidity and mortality. Chromosomal abnormalities occur with an incidence of 1 in 200 live births. The major cause of these abnormalities is chromosomal aneuploidy, an abnormal number of chromosomes inherited from the parents. One of the most frequent chromosomal aneuploidies is trisomy-21 (Down syndrome), which has an occurrence of 1 in 800 livebirths (Hook E B, Hamerton J L: The frequency of chromosome abnormalities detected in consecutive newborn studies: Differences between studies: Results by sex and by severity of phenotypic involvement. In Hook E B, Porter I H (eds): Population Cytogenetics, pp 63-79. New York, Academic Press, 1978). The primary risk factor for trisomy-21 is maternal age greater than 35, but 80% of children with trisomy-21 are born to women younger than 35 years of age. Other common aneuploidic conditions include trisomies 13 and 18, Turner Syndrome and Klinefelter syndrome.

Because 80% of children with trisomy-21 are born to women younger than 35 years of age, prenatal diagnostic screening programs designed on the basis of maternal age alone are inefficient. Prenatal screening programs have therefore been supplemented with maternal serum screening for analytes associated with fetal chromosomal aneuploidy, ultrasound, or a combination of both. Candidate serum markers that have been widely utilized include alpha-fetoprotein (AFP), unconjugated estriol, human choriogonadotrophic hormone (hHCG), and inhibin-A. However, with a screen positive rate of 2-5%, the detection rate for trisomy-21 and other aneuploidies has been disappointing, with detection rates of only 70-86% (Cuckle H. *Biochemical screening for Down syndrome*. Eur J Obstet Gynecol Reprod Biol. 92(1): 97-101, 2000). Further, the rate of true positive tests, i.e., trisomy-21 among those with a screen positive test is only 1-2%, resulting in an overall false positive rate in excess of 98%.

The definitive diagnosis of chromosomal aneuploidies following maternal serum screening and ultrasound requires a mid-trimester genetic amniocentesis. This is an invasive procedure associated with a 0.5% risk of loss of the pregnancy. Further, chromosomal analysis of amniotic fluid cells is a labor-intensive and time consuming procedure, taking up to 2 weeks. Reliable tests are therefore necessary to improve the detection of chromosomal aneuploidies from maternal serum, reduce the unacceptably high false positive rate of maternal screening, and increase the speed and efficiency of diagnosis from amniotic fluid following amniocentesis.

3. Diagnosis of Maternal/Fetal Conditions Using the Proteomic Profile of Biological Fluids The present invention provides an early and reliable, non-invasive method for the diagnosis of the foregoing and other similar maternal/fetal conditions by proteomic analysis of biological fluids, such as, for example, amniotic fluid, serum, plasma, cervical-vaginal fluid (CVF), urine, cerebrospinal fluid, breast milk, mucus, or saliva.

As noted before, in the context of the present invention the term "proteomic profile" is used to refer to a representation of the expression pattern of a plurality of proteins in a biological sample, e.g. a biological fluid at a given time. The proteomic profile can, for example, be represented as a mass spectrum, but other representations based on any physicochemical or biochemical properties of the proteins are also included. Although it is possible to identify and sequence all or some of the proteins present in the proteome of a biological fluid, this is not necessary for the diagnostic use of the proteomic profiles generated in accordance with the present invention. Diagnosis of a particular disease can be based on characteristic differences (unique expression signatures) between a normal proteomic profile, and proteomic profile of the same biological fluid obtained under the same circumstances, when the disease or pathologic condition to be diagnosed is present. The unique expression signature can be any unique feature or motif within the proteomic profile of a test or reference biological sample that differs from the proteomic profile of a corresponding normal biological sample obtained from the same type of source, in a statistically significant manner. For example, if the proteomic profile is presented in the form of a mass spectrum, the unique expression signature is typically a peak or a combination of peaks that differ, qualitatively or quantitatively, from the mass spectrum of a corresponding normal sample. Thus, the appearance of a new peak or a combination of new peaks in the mass spectrum, or any statistically significant change in the amplitude or shape of an existing peak or combination of existing peaks, or the disappearance of an existing peak, in the mass spectrum can be considered a unique expression signature. When the proteomic profile of the test sample obtained from a mammalian subject is compared with the proteomic profile of a reference sample comprising a unique expression signature characteristic of a pathologic maternal or fetal condition, the mammalian subject is diagnosed with such pathologic condition if it shares the unique expression signature with the reference sample.

A particular pathologic maternal/fetal condition can be diagnosed by comparing the proteomic profile of a biological fluid obtained from the subject to be diagnosed with the proteomic profile of a normal biological fluid of the same kind, obtained and treated the same manner. If the proteomic profile of the test sample is essentially the same as the proteomic profile of the normal sample, the subject is considered to be free of the subject pathologic maternal/fetal condition. If the proteomic profile of the test sample shows a unique expression signature relative to the proteomic profile of the normal sample, the subject is diagnosed with the maternal/fetal condition in question.

Alternatively or in addition, the proteomic profile of the test sample may be compared with the proteomic profile of a reference sample, obtained from a biological fluid of a subject independently diagnosed with the pathologic maternal/fetal condition ion question. In this case, the subject is diagnosed with the pathologic condition if the proteomic profile of the test sample shares at least one feature, or a combination of features representing a unique expression signature, with the proteomic profile of the reference sample.

In the methods of the present invention the proteomic profile of a normal biological sample plays an important diagnostic role. As discussed above, if the proteomic profile of the test sample is essentially the same as the proteomic profile of the normal biological sample, the patient is diagnosed as being free of the pathologic maternal/fetal condition to be identified. This "negative" diagnosis is of great significance, since it eliminates the need of subjecting a patient to unnecessary treatment or intervention, which could have potential side-effects, or may otherwise put the patient, fetus, or neonate at risk. The data are analyzed to determine if the differences are statistically significant.

The sensitivity of the diagnostic methods of the present invention can be enhanced by removing the proteins found both in normal and diseased proteome at essentially the same expression levels (common proteins, such as albumin and immunoglobulins) prior to analysis using conventional protein separation methods. The removal of such common proteins, which are not part of the unique expression signature, results in improved sensitivity and diagnostic accuracy. Alternatively or in addition, the expression signatures of the common proteins can be eliminated (or signals can be removed) during computerized analysis of the results, typically using spectral select algorithms, that are machine oriented, to make diagnostic calls.

The results detailed in the Examples below present proteomic profiles characteristics of intraamniotic infection (IAI) and pre-term labor that differ from the normal proteomic profile of amniotic fluid (AF) or cervical-vaginal fluid (CVF) in a statistically significant manner. In addition, the Examples present expression markers and unique expression signatures characteristic of IAI, pre-term delivery, Down syndrome, and other maternal or fetal conditions.

A particularly advantageous biological fluid for performing the non-invasive diagnostic methods of the present invention is the cervical-vaginal fluid (CVF). CVF is a complex biological fluid consisting of water, electrolytes, low-molecular-weight organic compounds (glucose, amino acids, and lipids), cells (leukocytes, lymphocytes, and epithelial cells), and a multitude of proteins and proteolytic enzymes that are predominantly synthesized by the endocervix (Blandau et al., *The Biology of the cervix*. University of Chicago Press: Chicago, 1973; p xi, 450p. CVF also contains secretions from vaginal cells, which include mucins, defensins, complement factors, immunogloblins, lactoferrin, and collectins (Blandau et al., supra). CVF flows over and lubricates the entire female reproductive tract, including the vagina, cervical, and uterine areas. CVF forms the first line of defense against external pathogens, signals fertility, and aids insemination, pregnancy, and labor (Blandau et al., supra; Bigelow, J. L. et al., *Hum Reprod* 2004, 19, (4), 889-92). CVF also contains flora such as *Lactobacilli crispatus* and *Lactobacilli vaginalis*. Secretions from this flora impart a low pH to the CVF, which enhances its anti-pathogen activity (Blandau et al., supra). Any imbalance in the vaginal flora or invasion of external flora results in bacterial vaginosis. In response to bacterial vaginosis, the secretion of several cytokines such as IL-1α, IL-1β, IL-10, IL-6 and TNF-α into the CVF by the cervical and vaginal endoepithelia changes (Mattsby-Baltzer, I et al., *Acta Obstet Gynecol Scand* 1998, 77, (7), 701-6; Eschenbach, D. A. et al., *J Clin Microbiol* 1989, 27, (2), 251-6). Failure to curb bacterial vaginosis has been positively correlated with cervical cancer (Mikamo, H et al., *J Infect Chemother* 1999, 5, (2), 82-85), pelvic inflammatory disease (Ness, R. B. et al., *Am J Epidemiol* 2005, 162, (6), 585-90.), endometritis (Haggerty, C. L. et al., *Clin Infect Dis* 2004, 39, (7), 990-5; Morris, M. et al., *Bjog* 2001, 108, (5), 439-50), and tubal infertility (Morris et al., supra). Bacterial vaginosis in pregnant women has been correlated with an increased risk of preterm labor and preterm birth (Gravett, M. G. et al., *Jama* 1986, 256, (14), 1899-903).

The cytokines and other defense molecules present in CVF also play an important role in infection, replication, and proliferation of sexually transmitted immune-deficiency viruses such as HIV and Herpes Simplex Virus (HSV) in the vagina (Poli, G. et al., *AIDS Res Hum Retroviruses* 1992, 8, (2), 191-7; Zara, F. et al., *Sex Transm Infect* 2004, 80, (2), 108-12; John, M. et al., *J Infect Dis* 2005, 192, (10), 1731-40). Analysis of the cationic polypeptide fraction of the CVF has identified 20 polypeptides that contribute to anti-HIV activity (Venkataraman, N. et al., *J Immunol* 2005, 175, (11), 7560-7). Previous studies have also identified a role for CVF in the trapping of HIV virions, thus preventing infection (Maher, D. et al., *Proc Natl Acad Sci USA* 2005, 102, (32), 11504-9; Quinones-Mateu, M. E et al., *Aids* 2003, 17, (16), F39-48). Recent studies have detected a correlation between several immune-response molecules in CVF and the incidence of subclinical premature rupture of membranes (PROM), which leads to preterm birth (Helmig, B. R. et al., *J Matern Fetal Neonatal Med* 2002, 12, (4), 237-46; Ogino, M. et al., *J Obstet Gynaecol Res* 2005, 31, (5), 421-6). During pregnancy, CVF could contain amniotic fluid (AF) derived from the uterus, either due to the disruption or parallel secretions of the chorionic-decidual interface. This "leakage" of AF into CVF provides the basis for the current non-invasive diagnosis for the presence of the fetal fibronectin, which has been used to predict preterm labor in women (Swamy, G. K. et al., *J Reprod Med* 2005, 50, (11), 851-6).

CVF is an important potential diagnostic site to monitor maternal and fetal health in pregnant women due to its minimally invasive collection method compared to AF, i.e., amniocentesis. The comprehensive catalog of proteins expressed in the CVF proteome provided herein enables better insight into the potential role of various CVF proteins that contribute to or reflect complications during pregnancy or vaginal pathologies.

Statistical methods for comparing proteomic profiles are well known in the art. For example, in the case of a mass spectrum, the proteomic profile is defined by the peak amplitude values at key mass/charge (M/Z) positions along the horizontal axis of the spectrum. Accordingly, a characteristic proteomic profile can, for example, be characterized by the pattern formed by the combination of spectral amplitudes at given M/Z vales. The presence or absence of a characteristic expression signature, or the substantial identity of two profiles can be determined by matching the proteomic profile (pattern) of a test sample with the proteomic profile (pattern) of a reference or normal sample, with an appropriate algorithm. A statistical method for analyzing proteomic patterns is disclosed, for example, in Petricoin III, et al., *The Lancet* 359:572-77 (2002).; Issaq et al., *Biochem Biophys Commun* 292:587-92 (2002); Ball et al., *Bioinformatics* 18:395-404 (2002); and Li et al., *Clinical Chemistry Journal*, 48:1296-1304 (2002).

4. Drug Screening Assays

The proteomic profiles of the invention find further utility in screening assays to identify drug candidates for the treatment of a particular maternal/fetal condition. Such screening assays are based on the ability of a test molecule to convert a proteomic profile containing an expression signature characteristic of the maternal/fetal condition to be treated into a proteomic profile devoid of the expression signature. In one particular embodiment, the ability of the test compound to convert a pathologic expression profile into a normal expression profile is tested. In another embodiment, the screening assay tests the ability of a test compound to convert a unique expression signature characteristic of a pathologic condition into a corresponding normal expression signature.

Such screening assays can be performed in vitro by treatment of a diseased biological sample and comparing the proteomics expression profiles before and after treatment. Alternatively or in addition, drug screening can be performed by treating a laboratory animal exhibiting the target pathologic maternal/fetal condition with a test compound, taking samples of a biological fluid of the animal before and after treatment, and comparing the proteomic profiles of the two samples. In this assay, it is also possible to take samples of biological fluid at various time points following treatment, and follow the time course of treatment. These methodologies may be applied also to characterize the toxicology of pharmaceutical agents, as well as to identify optimal candidates for specific therapies.

The test compounds can, for example, be peptides, non-peptide small organic molecules, proteins, polypeptides, antibodies (including antibody fragments), antisense molecules, oligonucleotide decoys, and any other classes of molecules that have been used previously as drugs or drug candidates.

The biological fluid can, for example, be amniotic fluid, serum (e.g. maternal serum), plasma, urine, cerebrospinal fluid, breast milk, mucus, or saliva.

Therapeutically active compounds identified can be formulated in conventional pharmaceutical formulations. A compendium of art-known formulations is found in Remington's Pharmaceutical Sciences, latest edition, Mack Publishing Company, Easton, Pa. Reference to this manual is routine in the art.

5. Protein Arrays

Both the diagnostic and the screening assays discussed above can be performed using protein arrays. In recent years, protein arrays have gained wide recognition as a powerful means to detect proteins, monitor their expression levels, and investigate protein interactions and functions. They enable high-throughput protein analysis, when large numbers of determinations can be performed simultaneously, using automated means. In the microarray or chip format, that was originally developed for DNA arrays, such determinations can be carried out with minimum use of materials while generating large amounts of data.

Although proteome analysis by 2D gel electrophoresis and mass spectrometry, as described above, is very effective, it does not always provide the needed high sensitivity and this might miss many proteins that are expressed at low abundance. Protein microarrays, in addition to their high efficiency, provide improved sensitivity.

Protein arrays are formed by immobilizing proteins on a solid surface, such as glass, silicon, micro-wells, nitrocellulose, PVDF membranes, and microbeads, using a variety of covalent and non-covalent attachment chemistries well known in the art. The solid support should be chemically stable before and after the coupling procedure, allow good spot morphology, display minimal nonspecific binding, should not contribute a background in detection systems, and should be compatible with different detection systems.

In general, protein microarrays use the same detection methods commonly used for the reading of DNA arrays. Similarly, the same instrumentation as used for reading DNA microarrays is applicable to protein arrays.

Thus, capture arrays (e.g. antibody arrays) can be probed with fluorescently labelled proteins from two different sources, such as normal and diseased biological fluids. In this case, the readout is based on the change in the fluorescent signal as a reflection of changes in the expression level of a target protein. Alternative readouts include, without limitation, fluorescence resonance energy transfer, surface plasmon resonance, rolling circle DNA amplification, mass spectrometry, resonance light scattering, and atomic force microscopy.

For further details, see, for example, Zhou H, et al., *Trends Biotechnol.* 19:S34-9 (2001); Zhu et al., *Current Opin. Chem. Biol.* 5:40-45-(2001); Wilson and Nock, *Angew Chem Int Ed Engl* 42:494-500 (2003); and Schweitzer and Kingsmore, *Curr Opin Biotechnol* 13:14-9 (2002). Biomolecule arrays are also disclosed in U.S. Pat. No. 6,406,921, issued Jun. 18, 2002, the entire disclosure of which is hereby expressly incorporated by reference.

6. Immunoassays

The diagnostic assay of the present invention can also be performed in the form of various immunoassay formats, which are well known in the art. There are two main types of immunoassays, homogenous and heterogenous. In homogenous immunoassays, both the immunological reaction between an antigen and an antibody and the detection are carried out in a homogenous reaction. Heterogeous immunoassays include at least one separation step, which allows the differentiation of reaction products from unreacted reagents.

ELISA is a heterogenous immunoassay, which has been widely used in laboratory practice since the early 1970's. The assay can be used to detect antigens in various formats.

In the "sandwich" format the antigen being assayed is held between two different antibodies. In this method, a solid surface is first coated with a solid phase antibody. The test sample, containing the antigen (i.e. a diagnostic protein) being measured, is then added and allowed to react with the bound antibody. Any unbound antigen is washed away. A known amount of enzyme-labelled antibody is then allowed to react with the bound antigen. Any excess unbound enzyme-linked antibody is washed away after the reaction. The substrate for the enzyme used in the assay is then added and the reaction between the substrate and the enzyme produces a colour change. The amount of visual colour change is a direct measurement of specific enzyme-conjugated bound antibody, and consequently the antigen present in the sample tested.

ELISA can also be used as a competitive assay. In the competitive assay format, the test specimen containing the antigen to be determined is mixed with a precise amount of enzyme-labelled antigen and both compete for binding to an anti-antigen antibody attached to a solid surface. Excess free enzyme-labelled antigen is washed off before the substrate for the enzyme is added. The amount of color intensity resulting from the enzyme-substrate interaction is a measure of the amount of antigen in the sample tested.

Homogenous immunoassays include, for example, the Enzyme Multiplied Immunoassay Technique (EMIT), which typically includes a biological sample comprising the compound or compounds to be measured, enzyme-labeled molecules of the compound(s) to be measured, specific antibody or antibodies binding the compound(s) to be measured, and a specific enzyme chromogenic substrate. In a typical EMIT excess of specific antibodies is added to a biological sample. If the biological sample contains the proteins to be detected, such proteins bind to the antibodies. A measured amount of the corresponding enzyme-labelled proteins is then added to the mixture. Antibody binding sites not occupied by molecules of the protein in the sample are occupied with molecules of the added enzyme-labelled protein. As a result, enzyme activity is reduced because only free enzyme-labelled protein can act on the substrate. The amount of substrate converted from a colorless to a colored form determines the amount of free enzyme left in the mixture. A high concentration of the protein to be detected in the sample causes higher absorbance readings. Less protein in the sample results in less enzyme activity and consequently lower absorbance readings. Inactivation of the enzyme label when the Ag-enzyme complex is Ab-bound makes the EMIT a unique system, enabling the test to be performed without a separation of bound from unbound compounds as is necessary with other immunoassay methods.

Part of this invention is also an immunoassay kit comprising, in separate containers (a) monoclonal or polyclonal antibodies having binding specificity for the polypeptides used in the diagnosis of a particular maternal/fetal condition, such as intra-amniotic infection or preterm birth; (b) and anti-antibody immunoglobulins. This immunoassay kit may be utilized for the practice of the various methods provided herein. The monoclonal or polyclonal antibodies and the anti-antibody immunoglobulins may be provided in an amount of about 0.001 mg to 100 grams, and more preferably about 0.01 mg to 1 gram. The anti-antibody immunoglobulin may be a polyclonal immunoglobulin, protein A or protein G or functional fragments thereof, which may be labeled prior to use by methods known in the art. The monoclonal or polyclonal antibodies specific for the polypeptides used in the diagnosis of a particular maternal/fetal condition can be adapted to rapid spot quantification utilizing calorimetric or charge state detection using suitable reading devices available in the field.

7. Mass Spectrometry Based Assays

Recent advances in mass spectrometry (Anderson L. and Hunter C. L., *Mol Cell Proteomics,* 2006 April; 5(4):573-88) enable quantification of specific proteins and polypeptides by monitoring the specific ions by mass selection. These assays use mass selection to provide absolute specificity, first selection (MS1) involves capture of parent ion and, second step captures specific fragment of the parent ion (Multiple reaction monitoring, MRM) detection and quantification. With appropriate standards for a specific protein, MRM assays could provide a reliable quantification of analytes to monitor various disease specific biomakers. Monoclonal or polyclonal antibodies for markers of maternal fetal diseases can be used to capture and analyze by MRM assays.

8. Diagnostic and Treatment Methods

The diagnostic methods of the present invention are valuable tools for practicing physicians to make quick treatment decisions, which are often critical for the survival of the infact and/or mother. Thus, for example, if a pregnant woman shows symptoms of pre-term labor, it is important to perform a diagnostic test to determine if intra-uterine infection is present. If the quick and non-invasive diagnostic test herein confirms the presence of intra-uterine infection, the physician has to assume that a pre-term birth will inevitably take place, and needs to take immediate steps to improve the chances of the survival of the pre-term infact and limit the risks to the mother's health.

If the test for intra-uterine infection is negative, the question remains if a pre-term delivery is still to be expected. Currently, sometimes a single-marker fetal fibronectin (fFN) test is used for this purpose. The absence of fFN in the CVF of the pregnant patient is a good indicator that the pregnancy will continue for at least two additional weeks. However, based on the presence of fFN (positive test), it is not possible to reliably predict whether pre-term birth in likely to take place. The multi-marker diagnostic tests of the present invention provide are reliable predictors of the likelihood of pre-term delivery both in the case of negative and positive test results.

Alternatively, if the patient shows symptoms of pre-term delivery and a diagnostic test (either a test herein or any other test used in clinical practice) is used to assess the likelihood of pre-term delivery, a test for intra-uterine infection can be performed as a follow-up, to provide more specific information and enable the physician to make better treatment decisions.

Further details of the invention will be apparent from the following non-limiting examples.

Example 1

Protocols Used in the Proteomic Analysis of Amniotic Fluid to Determine Diagnostic Markers of Intra-Amniotic Infection The following protocols were used in the proteomic analysis of amniotic fluid described in Examples 2-13 below.

Primate Model of Intra-Amniotic Infection

This protocol was approved by the Institutional Animal Care Utilization Committee of the Oregon National Primate Research Center, and guidelines for humane care were followed. Three pregnant rhesus monkeys (*Macaca mulatta*) with timed gestations were chronically catheterized as previously described (Haluska G J, et al., Temporal changes in uterine activity and prostaglandin response to RU 486 in rhesus macaques in late gestation, *Am J Obstet Gynecol* 157: 1487-95 (1987); and Gravett M G, et al., An experimental model for intramniotic infection and preterm labor in rhesus monkeys. *Am J Obstet Gynecol* 171: 1660-7 (1994)). Briefly, at approximately day 110 of gestation (term is 167 days) pregnant animals were conditioned to a jacket and tether system (Ducssay C A, et al., Simplified vest and tether system for maintenance of chronically catheterized pregnant rhesus monkeys. *Lab. Anim Sci* 38:343-4 (1988)). After conditioning, intrauterine surgery was performed between days 119 and 126 of gestation under general anesthesia. Maternal femoral arterial and venous catheters, fetal arterial and venous catheters, two open-ended intra-amniotic pressure catheters, myometrial electromyographic electrodes, and fetal electrocardiographic electrodes were surgically implanted. All animals received terbutaline sulfate (1 mg intravenously over 3 to 5 hours twice daily) for 1 to 5 days after surgery to control uterine irritability. Animals also received cefazolin (250 mg intravenously every 12 hours), which was discontinued at least 48 hours before inoculation of bacteria.

After postoperative stabilization for 8 to 13 days (day 126 to 138 of gestation), intra-amniotic infection was established by intra-amniotic inoculation of $10^6$ colony-forming units (cfu) of group B *Streptococcus*, type III, grown in overnight cultures in Todd-Hewitt broth, centrifuged, washed, and suspended in 0.5 ml of saline solution (n=3 animals), $10^7$ cfu of *Ureaplasma urealyticum* (1 animal) or *Mycoplasma hominis* (1 animal), grown in broth. Amniotic fluid samples were collected serially from all animals during the study period (daily before inoculation and every 4 to 12 hours after inoculation) for quantitative bacterial cultures, white blood cell analysis by hemocytometer, and cytokine and prostaglandin concentrations (previously reported—Gravett M G, et al., An experimental model for intra-amniotic infection and preterm labor in rhesus monkeys. *Am J Obstet Gynecol* 171: 1660-7 (1994)).

Fetal electrocardiographic and uterine activity (electromyographic and intra-amniotic pressure) were continuously recorded from surgery until delivery. Uterine contractility was recorded as the area under the contraction curve per hour and expressed as the hourly contraction area (HCA) in millimeters of mercury times seconds/hour.

The maternal cervix was palpated vaginally before infection and serially thereafter. Consistency, effacement, and dilatation were recorded at each examination. After delivery, by cesarean section in all except one animal and vaginally in one animal, decidual, placental, and inter membrane bacterial cultures were obtained form infected animals to confirm infection and histopathologic studies were performed.

Amniotic Fluid Assays

Amniotic fluid samples (3 ml) were immediately centrifuged after collection at 3,000 rpm and 4° C. for 20 minutes. The sediment was saved for cellular analysis and the supernatant stored in pyrogen-free sterile vials at −20° C. until assayed.

Human Study

The study population was drawn from 309 women admitted in premature labor with intact fetal membranes to the University of Washington Medical Center or associated hospitals in Seattle between Jun. 25, 1991 and Jun. 30, 1997, as previously described (Hitti J, et al., Amniotic fluid tumor necrosis factor-$\alpha$ and the risk of respiratory distress syndrome among preterm infants. *Am J Obstet Gynecol* 177:50-6 (1997)). All women provided written informed consent, and the study protocol was approved by the Institutional Review Boards for all participating hospitals. The participants were at gestational ages of 22 to 34 weeks by last menstrual period or from the earliest available ultrasound. All participants had intact fetal membranes at study enrollment. Preterm labor was defined as regular uterine contractions at a frequency of 10 minutes with either documented cervical change or a cervical dilatation of 1 centimeter or effacement of 50%. Women with cervical dilatation >4 centimeters or ruptured membranes at admission were excluded. Women with multiple gestations, cervical cerclage, placenta previa, abruptio placentae, diabetes, hypertension, and pre-eclampsia were considered eligible if they otherwise met study criteria.

Transabdominal amniocentesis was performed under ultrasound guidance for all study participants and maternal venous blood was also collected by venipuncture at the time of enrollment From this study population, a subset (Tables 1A and B) was retrospectively identified for proteomic analysis as reported here. This subset included 11 patients with evidence of intrauterine infection (as defined by the recovery of a microbial pathogen form amniotic fluid or an amniotic fluid IL-6 concentration of >2,000 pg/ml), and a randomly selected subset of 11 patients without intrauterine infection but with preterm birth and 11 patients without infection and with preterm labor responsive to tocolytic therapy and who had subsequent term birth. These patients constitute the study population for this report.

The study population was divided into three groups: 1) those patients with evidence of intrauterine infection, based upon either recovery of microorganisms from amniotic fluid or an amniotic fluid IL-6 concentration of >2,000 pg/ml; 2) those patients with preterm labor and delivery prior to 35 weeks of gestation without evidence of intrauterine infection; and 3) those patients with preterm labor responsive to tocolytic therapy who delivered at >35 weeks of gestation. There were no differences in maternal age, race, or parity between these three groups (Tables 1A and B). However, patients with intrauterine infection were seen at a somewhat earlier gestational age at enrollment (p=0.10) and delivered at a significantly earlier gestation age than those patients with preterm delivery without infection or those with term delivery (27.3+0.9 weeks versus 29.8+1.0 and 37.0+0.9 weeks respectively, p<0.0001). In addition, those with intrauterine infection had a significantly shorter enrollment to delivery interval (2.1+5.6 days, compared to 8.4+6.3 and 46.9+5.6 days for the other two groups, p<0.0001). Ninety-one percent of those with intrauterine infection delivered within seven days of enrollment.

Among those eleven patients with infection, microorganisms were recovered from four (2 with *Escherichia coli*, 1 with *Candida albicans*, and 1 with mixed anaerobes); all of these patients delivered within seven days. Seven other patients were identified based upon amniotic fluid IL-6 concentrations of greater than 2,000 pg/ml. The mean amniotic fluid concentration of interleukin-6 was 27.7+7.8 ng/ml among these patients, compared to 0.68+0.20 ng/ml among those with preterm delivery without infection and 0.25+0.13 ng/ml among those with preterm labor and term delivery ($p<0.01$).

The characteristics of the study population are shown in Table 1A. In Table 1A data expressed as mean standard deviation. Analysis by ANOVA for continuous data and Chi-square for categorical data. Abbreviations: PMD, premature delivery <35 weeks; IUI, intrauterine infection; PML, premature labor without delivery.

The screening results are shown in Table 1B.

In Tables 1A and 1B, data are expressed as mean standard deviation. Analysis by ANOVA for continuous data and Chi-square for categorical data. Abbreviations: PMD, premature delivery <35 weeks; IUI, intrauterine infection; PML, premature labor without delivery. Table 1C shows the Fisher's test significance values for the screening test results.

Proteomic Analysis of Amniotic Fluid

1-Dimensional (1-D) Gel Electrophoresis Analysis

100 μg of amniotic fluid after reduction with iodoacetamide was loaded on a 15% SDS-PAGE gel. Electrophoresis was conducted at 80V to separate the proteins in the sample. After electrophoresis the gel was stained with Coomasie blue R-250 and images were collected using Bio-Rad GS800 densitometer and PDQUEST software. Individual bands were cut from the gel, destained and digested in-gel with trypsin for 24-48 hrs at 37° C. The peptides were extracted with 0.1% TFA and dried in a speedvac. The extract was dissolved in 0.1% TFA and purified using Zip Tip$_{c18}$ pipette tips from Millipore. (Marvin L., et al. Identification of proteins from one-dimensional sodium dodecyl sulfate-polyacrylamide gel electrophoresis using electrospray quadrupole-time-of-flight tandem mass spectrometry. Rapid Commun Mass Spectrom. 14(14): 1287-92, 2000).

2-Dimensional (2-D) Gel Electrophoresis Analysis

Amniotic fluid (400-2000 μg) with or without removal of albumin was dissolved in IEF buffer and rehydrated on to a 24 cm IPG strip (pH 3-10) for 12 h at room temperature. After rehydration, the IPG strip was subjected to 1-dimension electrophoresis at 70~90 kVhrs. The IPG strip was then equilibrated with DTT equilibration buffer I and IAA equilibration buffer II for 15 minutes sequentially, before second dimension SDS-PAGE analysis. The IPG strip was then loaded on to a 4~20% SDS-PAGE gel and electrophoresis conducted at 120 V for 12 hrs to resolve proteins in the second dimension. The gel was stained with Coomassie Blue R-250 and imaged using Bio-Rad GS800 densitometer and PDQUEST software. Individual spots were cut from the gel, destained and digested in-gel with trypsin for 24-48 hrs at 37 C. The peptides were extracted with 0.1% TFA and purified using Zip Tip$_{c18}$ pipette tips from Millipore (2-D Proteome analysis protocols: Methods in Molecular Biology: 112, 1999).

HPLC Fractionation

Human amniotic fluid samples after removal of albumin and IgG (1-15 mg protein) were dissolved in 20 mM Tris-HCl, pH 7.5. Anion-exchange chromatography was performed using TSK gel DEAE-5PW column on a Waters 1525 HPLC equipped with an auto sampler and a UV absorbance detector. A linear salt elution gradient was used to fractionate the proteins. Fractions were collected at one minute intervals. Fractions were pooled, digested with trypsin and peptide mixtures were analyzed using the mass spectrometer (Q-Tof-2).

Mass Spectrometry Analysis (1) Q-Tof-2

Samples after in-gel digestion were analyzed on a Micromass™ Q-Tof-2 mass spectrometer connected to a Micromass™ CapLC. The Q-Tof-2 was equipped with a regular Z-spray or nanospray source and connected to a Integrafrit C18 75 um ID×15 cm fused silica capillary column. The instrument was controlled by, and data were acquired on, a Compaq™ workstation with Windows NT™ and MassLynx 3.5 software. The Q-Tof-2 was calibrated using Glu1Fibrinopeptide B by direct infusion or injection into the CapLC. A MS/MSMS survey method was used to acquire MS/MSMS spectra. Masses 400 to 1500 were scanned for MS survey and masses 50 to 1900 for MSMS. Primary data analysis was performed on a PC with Windows 2000 and SEQUEST™ (version 1.3) and/or LUTEFISK. Peak lists were generated, using the built-in automatic functions for peak-picking and applying centroid-fitting to each peak.

(2) LCQ™-MS

Protein spots from dried Coomassie blue stained gels were excised and rehydrated/washed for 30 min. in 0.5 ml of 20 mM ammonium bicarbonate, 50% acetonitrile solution. The gel regions were then dried by vacuum centrifugation and digested in situ by rehydrating in 20 nM sequencing grade modified trypsin (ProMega, Madison, Wis., USA) using the method of Courchesne and Patterson, Identification of proteins by matrix-assisted laser desorption/ionization masses, Methods Mol. Biol. 112:487-511 (1999). Tryptic digests were then concentrated by vacuum centrifugation, separated by reverse phase chromatography, and peptides analyzed by a model LCQ™ ion trap mass spectrometer (ThermoFinnigan, San Jose, Calif.). Samples were separated with Zorbax™ C-18 0.5 mm×150 mm microbore column using a 10 μL min$_{-1}$ flow rate and a gradient of 0 to 40% B (75% Acetonitrile in water) over one hour with an 1100 Capillary LC System (Agilent Technologies, Foster City, Calif.). Peptides were introduced directly into the standard ThermoFinnigan electrospray source. MS/MS spectra were acquired in an automated fashion using standard LCQ™ software and then analyzed further using SEQUEST™ (ThermoFinnigan). For further details see, Courchesne, P. L. and Patterson, S. D., supra.

Data Analysis (1) Sequest™ and DTASelect

Automated analysis of tandem mass spectra (MS/MS) was performed using SEQUEST™ software (ThermoFinnigan) as described by Yates et al., Methods Mol. Biol. 112:553-69 (1999). SEQUEST™ matches uninterrupted tandem mass spectra to database peptide sequences. Searches were run with the default parameters using a combined indexed non-redundant database of protein sequences obtained from the Protein Information Resource (release date) and SwissProt™ (release date). The database was constructed using the Xcalibur™ Database Manager (ThermoFinnigan). S-Carboxyamidated cysteine was the only considered modification.

Sequest™ results were further analyzed using DTASelect (The Scripps Research Institute, Tabb, 2002). DTASelect organizes and filters SEQUEST™ identifications. The default parameters were used except as follows: 1) any database matches including the string "keratin" in the protein description were excluded and 2) spectra from the LCQ™ mass spectrometer were filtered with a cross correlation score cut-off of 2.4 for the doubly charged ions. Each spectra and proposed sequence pair selected by DTASelect were visually inspected and the final results were input into a spreadsheet (Microsoft Excel™) or a database (Microsoft Access™) for management.

For further details, see also: Tabb D L, et al., DTASelect and Contrast: Tools for Assembling and Comparing Protein Identifications from Shotgun Proteomics. *J. Proteome Res.* 1:21-26 (2002).

(2) Lutefisk

Automated de novo sequencing of all spectra was performed using a computer program, Lutefisk 1900 v1.2.5 (Taylor J A, Johnson R S. Implementation and uses of automated de novo peptide sequencing by tandem mass spectrometry. *Anal Chem* 73(11):2594-604 (2001). Lutefisk generates peptide sequences for spectra of which some are sufficiently detailed for homology-based sequence searches. Modifications, acrylamide, carbamidomethylation, and phosphorylation, were considered.

MALDI Detection Protocol and Parameters

MALDI mass spectrometry was performed on a custom-built time-of-flight reflector mass spectrometer (Jensen O N, et al., Direct observation of UV-crosslinked protein-nucleic acid complexes by matrix-assisted laser desorption ionization mass spectrometry. *Rapid Commun Mass Spectrom* 7(6):496-501 (1993)) equipped with a two-stage delayed extraction source. Approximately 1 µL of sample solution was mixed with 1 µL SA (Sinapinic acid in 60:40 water/acetonitrile 0.1% TFA final conc.) A 1.0 µL droplet of this analyte/matrix solution was deposited onto a matrix pre-crystallized sample probe and allowed to dry in air. Mass spectra were produced by radiating the sample with a (355 nm) Nd:YAG laser (Spectra Physics) and operating the ion source at 23 kV with a 700 ns/1.0 kV delay. Every mass spectrum was recorded as the sum of 20 consecutive spectra, each produced by a single pulse of photons. Ions from an added standard were used for mass calibration.

SELDI Analysis of Amniotic Fluid

A total of 0.5-3.0 ug protein from amniotic fluid samples was spotted on a Normal Phase NP20 ($SiO_2$ surface), Reverse Phase H4 (hydrophobic surface: C-16 (long chain aliphatic), or immobilized nickel (IMAC) SELDI ProteinChip® array (Ciphergen Biosystems, Inc. Fremont, Calif.). After incubation at room temperature for 1 hour, NP1 and H4 chips were subjected to a 5 ul water wash to remove unbound proteins and interfering substances (ie buffers, salts, detergents). After air-drying for 2-3 minutes, two 0.5 ul applications of a saturated solution of sinapinic acid in 50% acetonitrile (v/v), 0.5% trifluoroacetic acid (v/v) was added and mass analysis was performed by time-of-flight mass spectrometry in a Ciphergen Protein Biology System II (PBS II), Issaq, J. H, et al.: The SELDI-TOF MS Approach to Proteomics: Protein Profiling and Biomarker Identification. Biochem Biophys Res Commun. 5:292(3):587-92, 2000.

Example 2

Identification of Proteins and Polypeptides Expressed in the Amniotic Fluid

Using the materials and methods described in Example 1, proteins and polypeptides expressed in normal and infected amniotic fluid were identified. Human and primate amniotic fluid samples (pooled and individual) were subjected to protein separation techniques (1-D, 2-D and HPLC fractionation) as described in Example 1. The separated proteins (gel bands, spots and fractions) were digested with trypsin to generate peptide pools. The peptide pools were analyzed using tandem MS to decipher their amino acid sequence and composition.

Five thousand MS spectra were selected using spectral verification programs. These spectral files were analyzed using de novo sequencing programs (Lutefisk, Peaks) to generate the amino acid sequence corresponding to each peptide. The de novo sequences generated from the peptide pool were used to search protein and DNA databases as described in Example 1.

Using homology maps and sequence verification, expression of a variety of proteins was discovered in the amniotic fluid. The detected proteins were analyzed for potential function based on known structural similarities (sequence homology maps). Proteins belonging to important functional classes involved in a wide range of diseases were discovered. Proteins and polypeptides discovered for the first time in the human amniotic fluid are listed in the attached Table 2 under these potential functional categories.

Proteins shown to be differentially expressed by immunoassays also, and proteins more abundantly or uniquely represented in the infected amniotic fluid are separately marked. In this context, relative abundance is defined as the amount of the peptides representing a certain polypeptide or protein in a test sample, relative to a reference sample. Accordingly, a protein is more abundantly represented in infected amniotic fluid if more peptides derived from the same protein are present in infected amniotic fluid than in a non-infected reference sample of amniotic fluid.

Table 3 lists proteins and polypeptides previously known to be present in amniotic fluid, the presence of which was reaffirmed by the present assays. Proteins which are known markers for infection related events are separately marked.

Diagnostic Markers for Intrauterine Conditions:

In view of their known biological functions, several proteins listed in the foregoing tables are promising candidates for detecting and monitoring intrauterine conditions. A few examples of such conditions and the corresponding protein markers are discussed below in greater detail.

Actin-Modulating and Related Proteins as Markers of Developmental Defects:

Moesin (Membrane-organizing extension spike protein), listed among the structural proteins in Table 2, is known to be responsible for linking transmembrane proteins to the actin cytoskeleton and implicated in various cell signaling pathways (Speck O, et al.: Moesin functions antagonistically to the Rho pathway to maintain epithelial integrity. *Nature* 2:421(6918):83-7, 2003). It was shown that Rho-family GTPases and their effectors to modulate the activities of actin modifying molecules such as Cofilin and Profilin (also listed as a structural protein in Table 2), resulting in cytoskeletal changes associated with growth cone extension or retraction (Tang B L. Inhibitors of neuronal regeneration: mediators and signaling mechanisms. Neurochem Int, 42(3):189-203, 2003). Coronin-like protein p57 (yet another structural protein listed in Table 2) is also involved in actin cross-linking and capping (Weitzdoerfer R et al.: Reduction of actin-related protein complex 2/3 in fetal Down syndrome. Biochem Biophys Res Commun. 293:836, 2002) and are dysregulated in known developmental defects. Gelsolin (see, the Gelsolin precursor listed an a transporter/binding protein in Table 2), another actin-modulating protein is also known to be developmentally regulated and important in organ systems (Arai M, Kwiatkowski D J. Differential developmentally regulated expression of gelsolin family members in the mouse. Dev Dyn, 215, 297, 1999). 14-3-3 proteins are also known epithelial markers which participate in signal transduction and differentiation pathways and are essential for normal development of brain and other vital organs (Wu C, Muslin A J. Role of 14-3-3 proteins in early *Xenopus* development. Mech Dev, 119, 45, 2002).

Accordingly, the listed actin-modulating proteins and other related molecules with important roles during development, that were identified for the first time in human amniotic fluid, could be used to detect developmental defects of various organ systems such as, central nervous system, cardiovascular system and other musculoskeletal deformities, which can, for example, result from chromosomal aneuploidies. This is particularly true for Profiling I, which has been shown to be differentially expressed in infected amniotic fluid, and the differential expression of which has been confirmed by immunoassay.

Markers of Infection and Immune-Response Related Disorders:

The present detection of macrophage capping protein, leukocyte elastase, neutrophil gelatenase-associated lipocalicn, myleoperoxidase, L-plastin (lymphocyte cytosolic protein) and calgranulins (see the list of immune response related genes in Table 2) infected amniotic fluid is the first demonstration of the presence and regulation of these proteins in intraamniotic infection. Several of these proteins are known responders of immune cells in response to infection, inflammation and stress. Macrophage capping protein (MCP) is a Ca(2+)-sensitive protein which modulates actin filaments and involved in inflammatory process (Dabiri G A, Molecular cloning of human macrophage capping protein cDNA. A unique member of the gelsolin/villin family expressed primarily in macrophages J Biol Chem 15; 267(23):16545-52, 1992). Similarly, Calgranulins are calcium binding proteins known to play a role in injury and wound healing (Thorey I S. et al. The Ca2+-binding proteins S100A8 and S100A9 are encoded by novel injury-regulated genes. J Biol Chem 21; 276(38):35818-25, 2001). Leukocyte elastase and neutrophil gelatinase-associated lipocalcin (NGAL) are involved in bacteriostatic and baceterolysis mechanisms (Goetz D H. et al. The neutrophil lipocalin NGAL is a bacteriostatic agent that interferes with siderophore-mediated iron acquisition. Mol Cell 10(5):1033-43, 2002).

In addition to the above immunomodulators we also discovered, for the first time, two antibacterial proteins Fall-39 and azurocidin in the infected amniotic fluid. Antibacterial protein Fall-39 (LL-37) binds to bacterial lipopolysaccharides (lps), and is expressed in bone marrow, testis and neutrophils. Fall-39 stimulates the degranulation of mast cells, and is a potent chemotactic factor for mast cells. Besides its antibacterial activities, Fall-39 may have the potential to recruit mast cells to inflammation foci. In the presence of the basal medium E, synthetic FALL-39 was highly active against *Escherichia coli* D21 and *Bacillus megaterium* Bm11. A protective role for Fall 39 has been proposed, when the integrity of the skin barrier is damaged, participating in the first line of defense, and preventing local infection and systemic invasion of microbes (Agerberth B, et al.: FALL-39, a putative human peptide antibiotic, is cysteine-free and expressed in bone marrow and testis. Proc Natl Acad Sci USA, 3:92(1):195-9, 1995).

Azurocidin (CAP37) is a cationic antimicrobial protein isolated from human neutrophils and has important implications in host defense and inflammation. It is released during inflammation and regulates monocyte/macrophage functions, such as chemotaxis, increased survival, and differentiation (Pereira H A. CAP37, a neutrophil-derived multifunctional inflammatory mediator. J Leukoc Biol 57(6):805-12, 1995).

Proteases and protease inhibitors play a key role in protein regulation and thus control several key physiological mechanisms. We have identified the expression of Serpin family of proteases (Serpin, squamous cell carcinoma antigen 1 & 2, glia derived nexin) for the first time in human amniotic fluid, including intraamniotic infection. The serpin superfamily of serine proteinase inhibitors has a central role in controlling proteinases in many biological pathways and implicated in conformational diseases, such as the amyloidoses, the prion encephalopathies and Huntington and Alzheimer disease (Lomas D A, Carrell R W, Serpinopathies and the conformational dementias. Nat Rev Genet; 3:759, 2002).

Additionally, in intraamniotic infection we identified the expression of Cystatins, well known proteinase inhibitors involved in immunomodulation (Vray B, Hartmann S, Hoebeke J. Immunomodulatory properties of cystatins. Cell Mol Life Sci:59(9):1503-12, 2002).

The listed proteins are promising markers of infection and/or immune-response related disorders.

It is noteworthy that peptides representing macrophage capping protein, neutrophil gelatinase-associated lipocalin, myeloperoxidase precursor, L-plastin, azurocidin, antibacterial protein Fall-39, calgranulin A, profilin I, glia-derived nexin, serpin I2, and cystatin A were more abundantly or uniquely detected in infected amniotic fluid relative to normal amniotic fluid, and/or showed differential expression in immunoassays. Accordingly, these proteins are particularly important as markers of intra-amniotic infection and/or immune-response related disorders.

Other Disease (Infection) Specific Proteins Detected in Human Amniotic Fluid

Gp-340 variant protein listed in Table 2, which has been detected in human infected amniotic fluid, is a scavenger receptor previously identified in lung. This protein is known to bind to bacteria (streptococcus and variants) The detection of this protein in infected amniotic fluid complements the sensitive proteomic approach of the present invention to identify biomarkers for IAI. Thus, Gp-340 variant protein identified in the infected amniotic fluid lends itself for the detection of neonatal sepsis).

IGFBP-1 (Proteolytic Fragment)

As shown in Table 2, IGFBP-1 has been shown to be differentially expressed in infected amniotic fluid. The insulin-like growth factor (IGF) systems is critically involved in fetal and placental growth and modulates steroid hormone actions in the endometrium through autocrine/paracrine mechanisms. IGF-I and IGF-II stimulated proliferation and differentiation, and maintain differentiated cell functions in several cell types in vitro. Endometrial stromal cells produce IGF-I and IGF-II as well as the high affinity IGF-binding proteins (IGFBPs). The mRNA of six high affinity IGFBPs, which can modulate IGF actions, are expressed in human endometrium. The most abundant IGFBP in human endometrium is IGFBP-1, which is secreted by predecidualized/decidualized endometrial stromal cells in late secretory phase and during pregnancy. This has implications for clinical obstetrics and gynecology, where there is evidence for a pathophysiological role for IGFBP-1 in pre-eclampsia, intrauterine growth restriction, polycystic ovarian syndrome and trophoblast and endometrial neoplasms.

The presence and regulation of an IGFBP-1 proteolytic fragment in human amniotic fluid and maternal serum opens a new way for monitoring intrauterine and maternal conditions associated with pregnancy.

For further details see, also Example 12 below.

Example 3

Figure 1B:
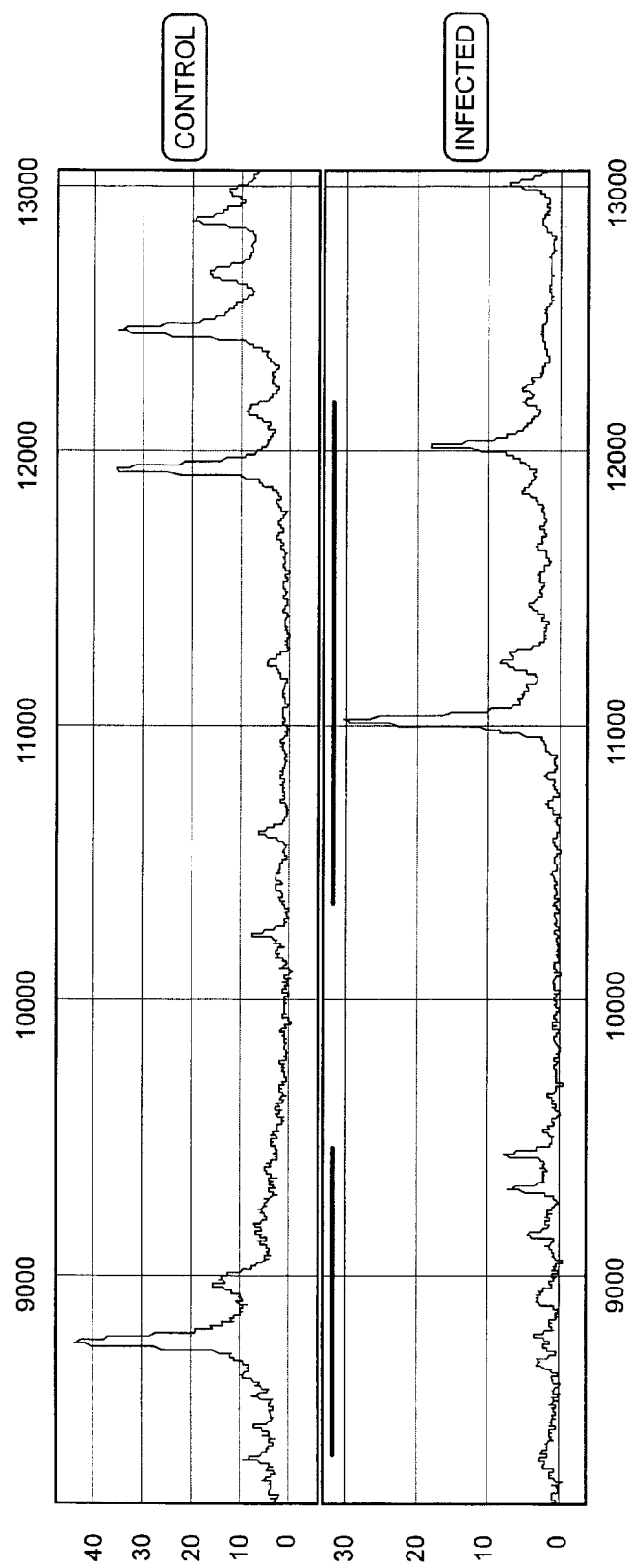
Figure 1C:
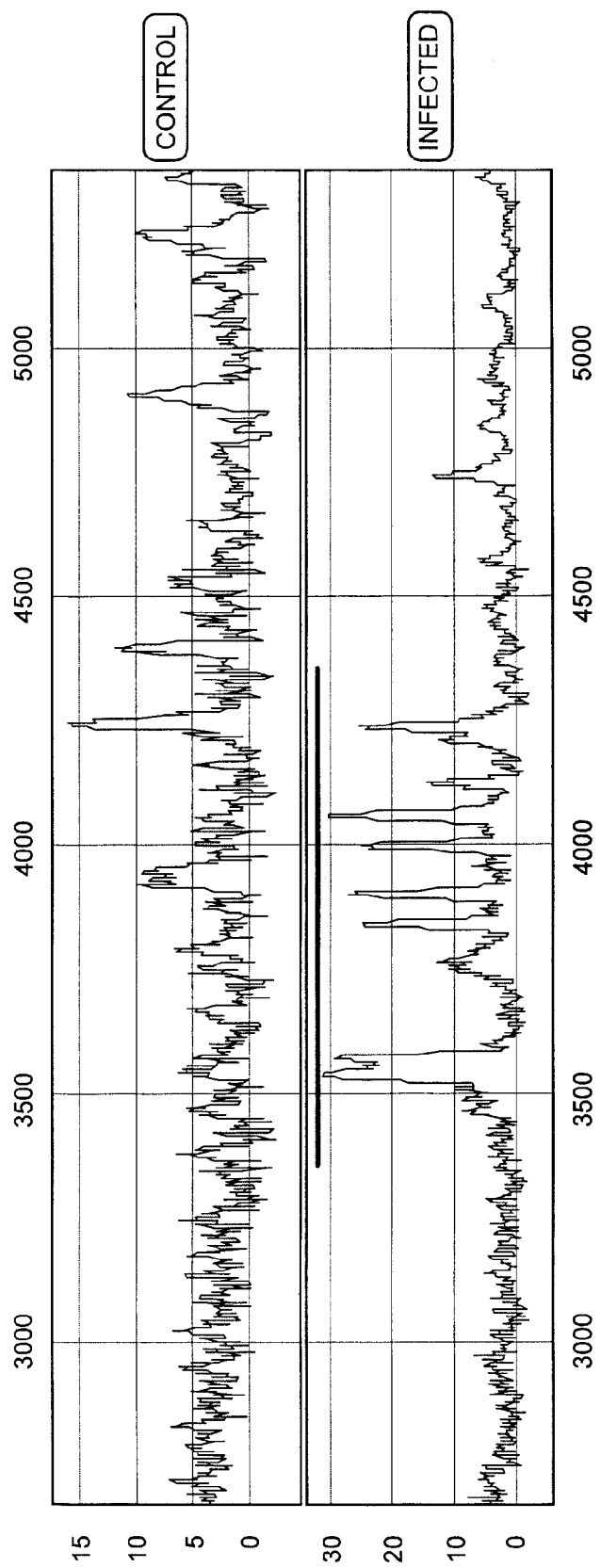

Protein Expression Profiles of Primate Amniotic Fluid Following Intrauterine Infection Protein expression profiles of primate amniotic fluid following intrauterine infection, compared with the corresponding normal expression profiles, are shown in FIGS. 1A-C.

As illustrated in FIGS. 1A-C, the global protein expression profiles of control and infected amniotic fluid are distinct. A detailed spectra of amniotic fluid profiles in a smaller mass range (FIGS. 1B and 1C), shows distinct and characteristic differences between the protein expression profiles of control and infected samples approximately in the 3-5 KDa and 10-12 KDa range. This illustrates global regulation of protein expression in response to intrauterine infection and the ability to detect a unique expression signature diagnostic of intrauterine infection.

Example 4

Early Detection of Diagnostic Pattern/Profile of Infection in the Primate Amniotic Fluid FIGS. 2A-C show the time course analyses of the primate amniotic fluid in response to infection (GBS). Amniotic fluid was collected before the inoculation of bacteria and serially after infection and subjected to SELDI-TOF analysis as described in Example 1. FIG. 2A shows the protein expression profile before infection, FIG. 2B 12 hours after infection, and FIG. 2C 36 hours after infection.

As shown in FIG. 2C, one of the diagnostic peaks (10-11 KDa) of intrauterine infections clearly reaches high levels of expression within 36 hours of acute infection. This demonstrates that diagnostic protein profiles can be used for monitoring the disease state and response to treatment.

Example 5

Figure 3A:
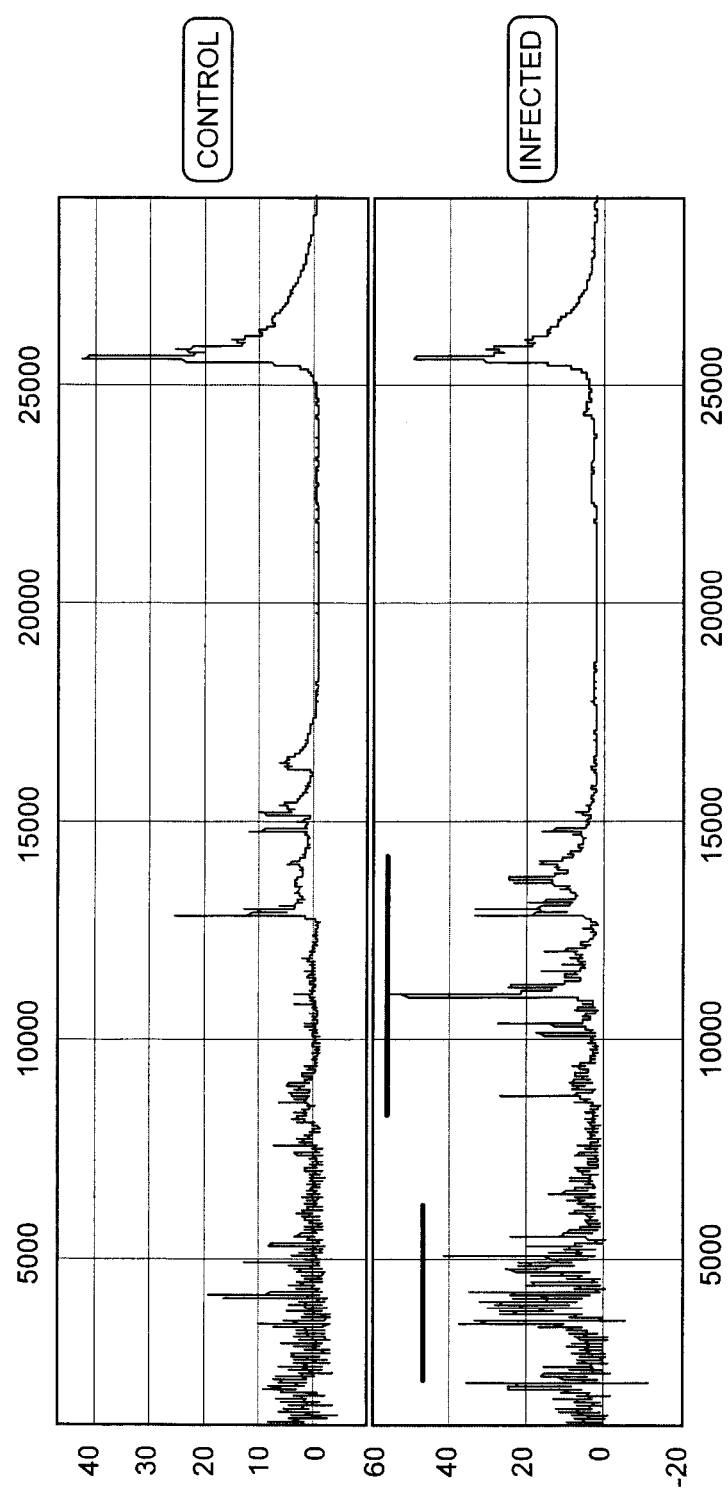
FIGS. 3A-C. Infection-induced differential protein expression in the human amniotic fluid. SELDI-TOF analysis of amniotic fluid extracts bound to chemically defined Normal Phase chip arrays. A). Whole spectrum collected at 235 laser intensity showing the differences in the peak intensities. B) Detailed spectrum showing the differences in the 10 to 12 KDa region between control and infected. C) Detailed spectrum showing the differences in the 3-5 KDa region between control and infected. D) Peak intensity based clusters that differentiates between control and infected.
Figure 3B:
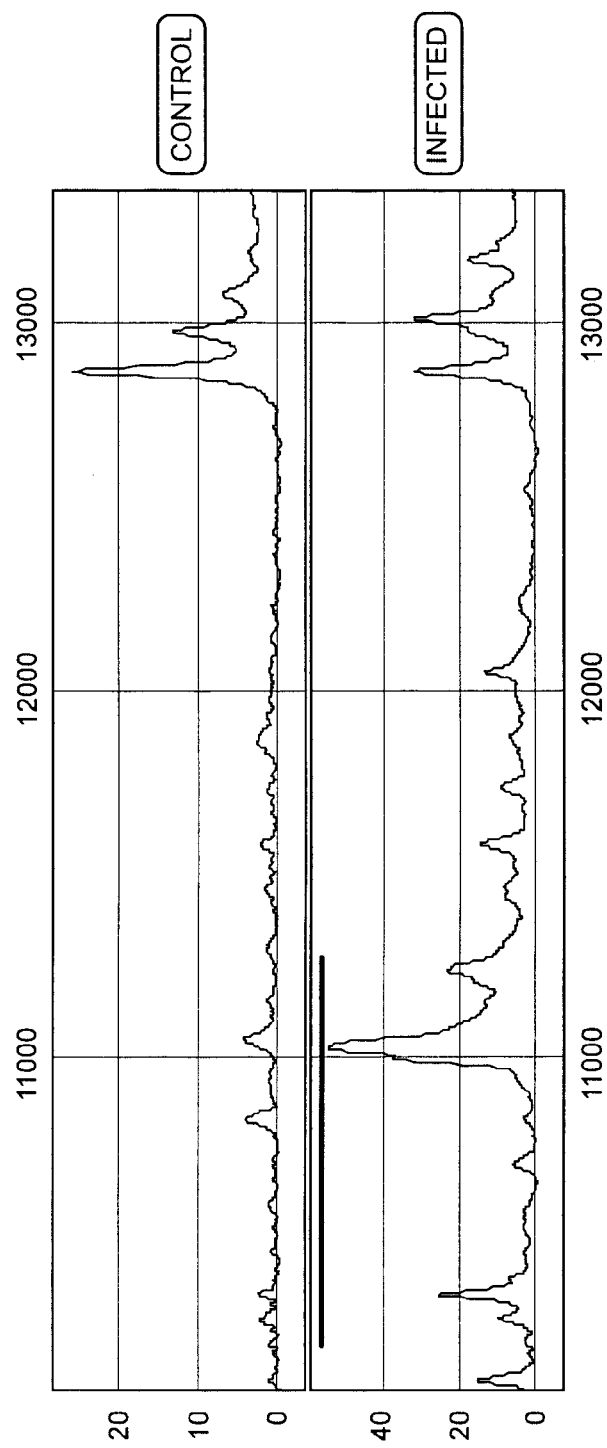
Figure 3C:
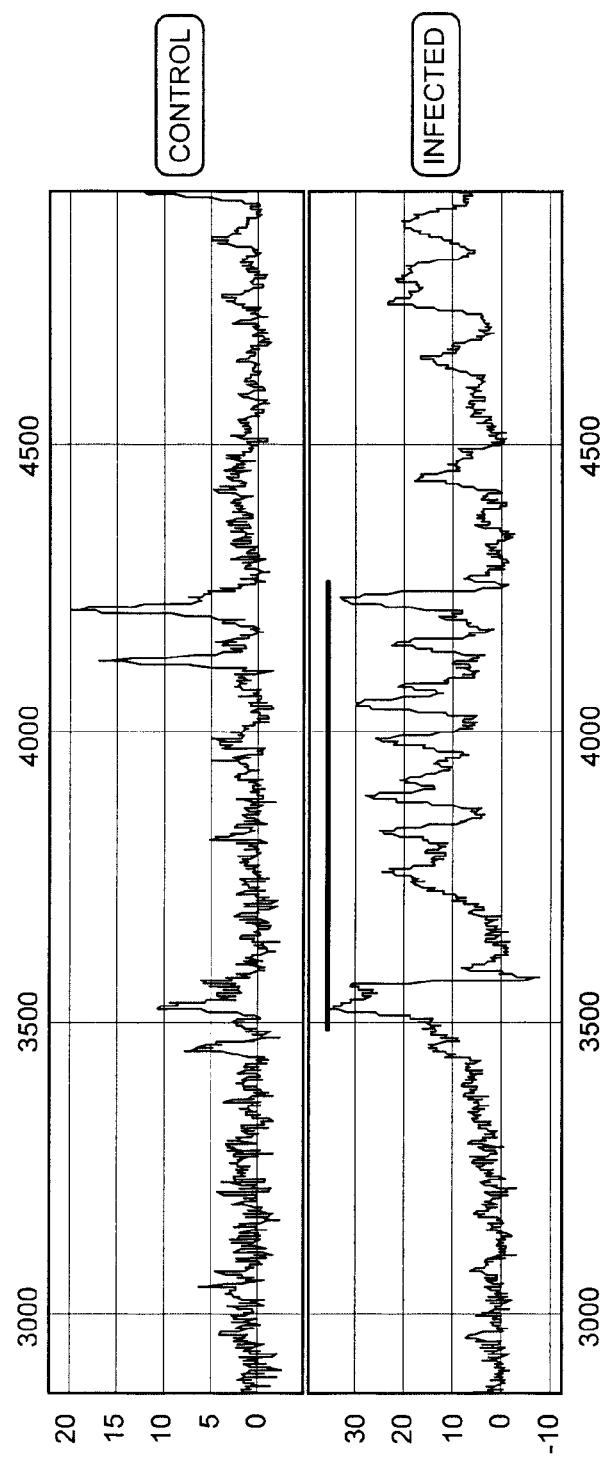

Protein Expression Profiles of Human Amniotic Fluid Following Intrauterine Infection FIGS. 3A-C show the results of SELDI-TOF analysis of amniotic fluid extracts bound to chemically defined normal phase chip arrays. FIG. 3A shows the whole spectrum at 235 laser intensity. FIG. 3B is a detailed spectrum showing the differences between infected and control samples in the 10-12 kDa region. FIG. 3C is a detailed spectrum showing the characteristic differences between infected and control samples in the 3-5 kDa region.

As shown in FIGS. 3A-C, the global protein expression profiles of control and infected amniotic fluid are distinct. A detailed spectra of amniotic fluid profiles in a smaller mass range (FIGS. 3B and C), shows distinct over expressed proteins (3-5. KDa and 10-12 KDa range) between control and infected samples. Analysis of protein peaks relative intensities suggests the presence of two distinct diagnostic clusters (10-12 kDa and 3-5 kDa ranges). This illustrates global regulation of protein expression in response to intrauterine infection and the ability to detect a unique expression signature diagnostic of intrauterine infection both in human and primate models.

It is noteworthy that the diagnostic pattern of human amniotic fluid is in good agreement with the diagnostic pattern of primate amniotic fluid (Examples 3 and 4).

Example 6

Generation of Diagnostic Profiles Using Different Mass Spectrometers

The diagnostic protein expression profile can be detected using different types of mass spectrometers. It has been examined whether different mass spectrometers produce similar diagnostic profiles. If the diagnostic profiles are substantially independent on the type of mass spectrometer, the detected differential protein expression in the amniotic fluid can provide a diagnostic signature for intrauterine infection.

Figure 4A:
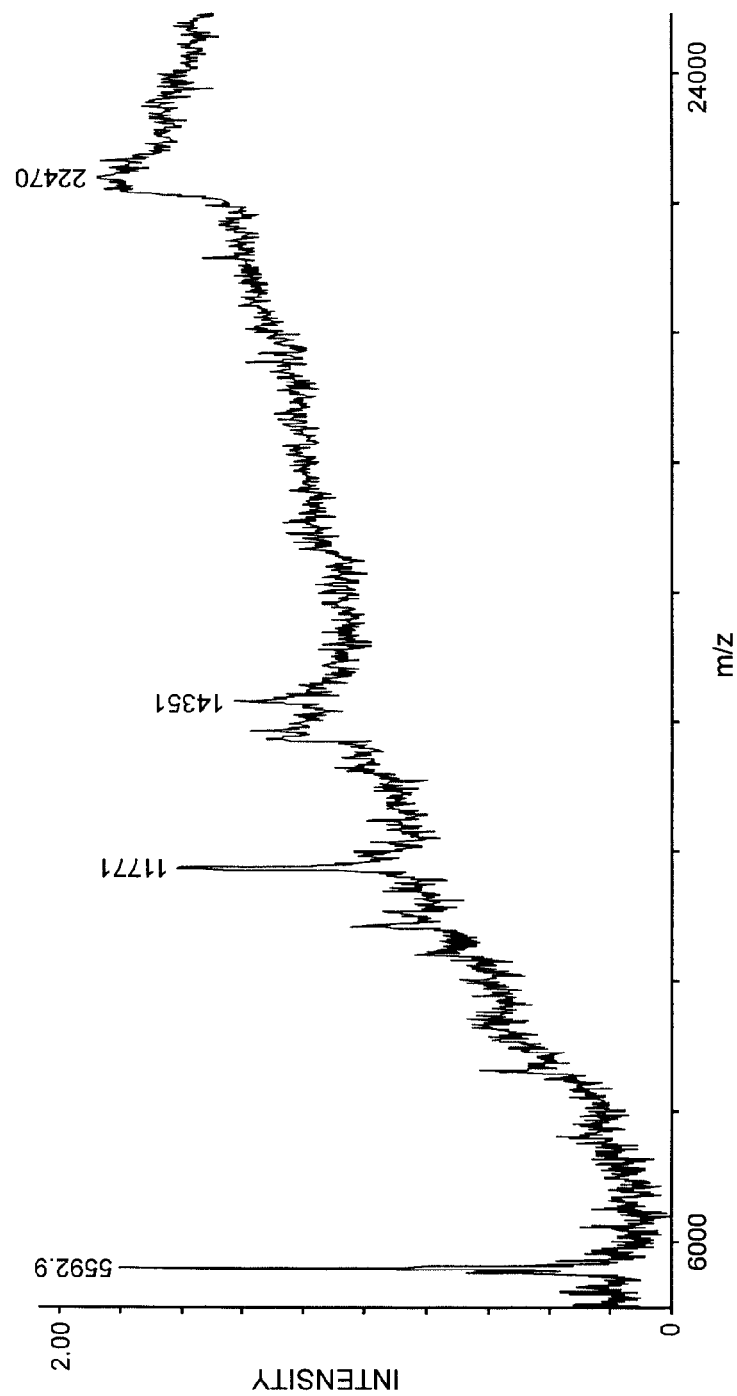
FIGS. 4A and 4B. Mass spectra acquired on a generic MALDI-TOF mass spectrometer, using amniotic fluid from human A) control, without intrauterine infection and B) sample, with intrauterine infection.
Figure 4B:
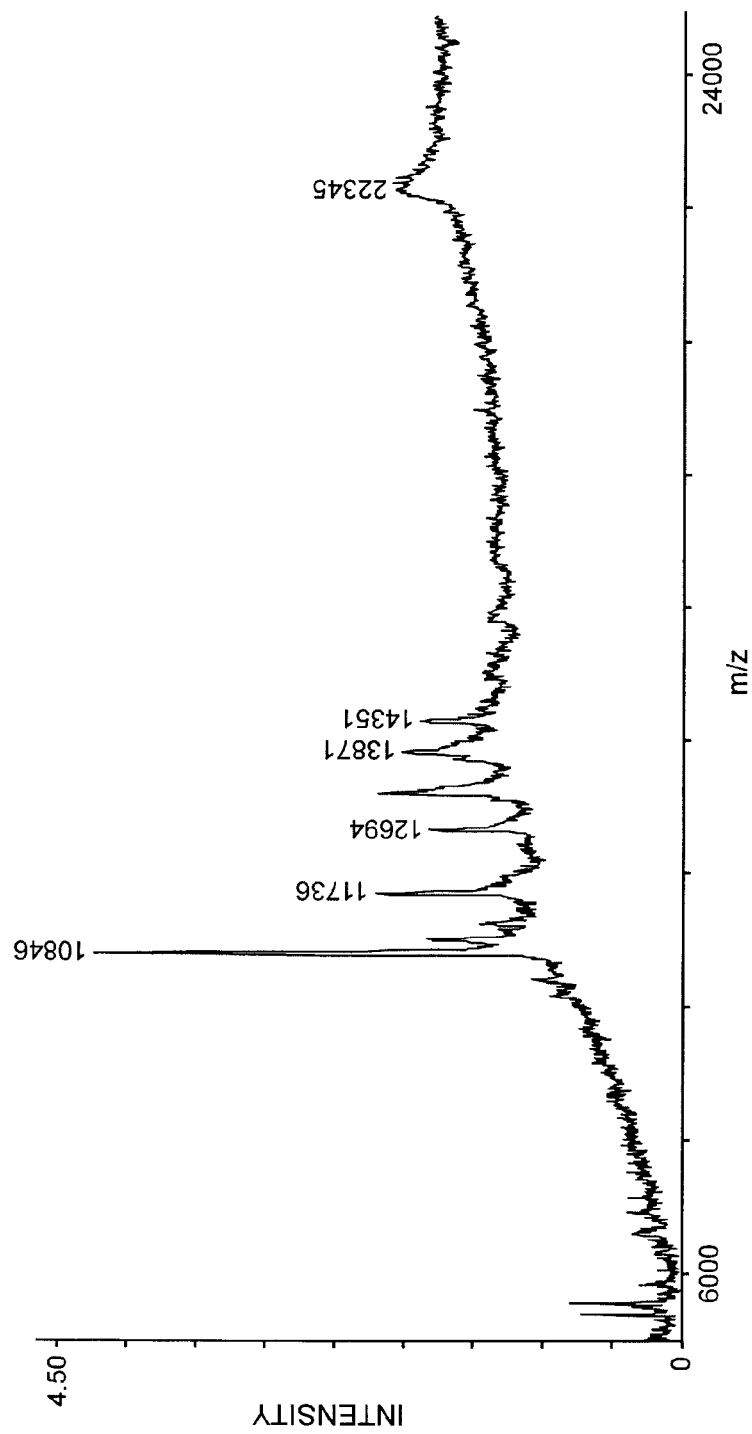

FIGS. 4A and 4B show mass spectra acquired on a generic MALDI-TOF mass spectrometer (Jensen O N, et al., Direct observation of UV-crosslinked protein-nucleic acid complexes by matrix-assisted laser desorption ionization mass spectrometry. *Rapid Commun Mass Spectrom* 7(6):496-501 (1993)) using amniotic fluid from human control (A), without intrauterine infection, and a sample (B) with intrauterine infection.

As shown in FIGS. 4A and B, the diagnostic profile of intrauterine infection in the 10-12 KDa range is detected using the alternate mass spectrometer is similar to the profile detected using the SELDI-TOF machine. This indicates that differential protein expression profiles are robust and can be detected using a wide range of current mass spectrometers.

In summary, it has been discovered that amniotic fluid proteins and polypeptides exhibit differential expression patterns diagnostic of disease state. The results presented here demonstrate that disease-specific diagnostic patterns can be detected using multiple mass spectrometry approaches. The patterns or protein expression profiles are comparable between humans and primates. The profiles can be used to monitor a time-course (infection or treatment) effect.

Example 7

Quantification of Protein and Polypeptide Expression in Amniotic Fluid for Diagnostic and Prognostic Monitoring

SDS-PAGE:

Proteins from human amniotic fluid (AF) containing high salt was precipitated with acetone. 100 µg of amniotic fluid proteins was run on a 15% SDS-PAGE. The gel was stained with Coomassie Blue R-250. The gel image was scanned by Bio-Rad gel Scanner.

FIG. 5 shows the SDS-Coommassie Blue stained gel of A) 4 human control AF samples pooled; B) individual control AF sample; C) 4 human infected AF samples pooled; and D) individual infected AF sample.

FIG. 5 shows significant differences between the control and infected protein expression levels in the 10-15 KDa range. It has been concluded that some of the proteins and proteolytic fragments in this mass detected using the mass spectrometers are responsible for the diagnostic profiles reflective of the protein expression levels, and have diagnostic and prognostic utility.

Example 8

Western Blot Analysis of Amniotic Fluid from Intrauterine Infection

100 µg of AF proteins were run on 4-20% SDS-PAGE at 200 V for 60 minutes and transferred to PVDF membrane at 90 mM for 75 minutes. The membrane was blocked with 5% milk PBST for 45 min at RT and incubated with 1 µg/ml primary antibody (Santa Cruz and Dako) overnight at 4 C. After wash with TBST 3 times, the membrane was incubated with secondary antibody IgG-HRP (Sigma) for 90 min at RT and visualized with ECL (Pierce).

The results are shown in FIG. 6: A) Control AF sample (pooled); B) Infected AF sample (pooled). FIG. 6 shows that IGFBP1 (11 KDa), profilin and ceruloplasmin (130 KDa) are expressed at a higher level in infected AF compared to non-infected AF. L-Plastin levels were lower in the infected sample compared to control AF sample. These proteins were also identified from the human infected samples using MS approaches (de novo sequencing) and are listed in Example 2 above.

Example 9

Immunoprecipitation Analysis of Amniotic Fluid from Intrauterine Infection

Two micrograms of primary antibody was mixed with 600 µg of AF protein and incubated at 4° C. overnight. 15 µl of protein G Sepharose beads was added and incubated on a shaker for 60 minutes at room temperature. The beads were washed with IP buffer for 6 times.

The results are shown in FIG. 7, where (A) shows the control amniotic fluid sample (pooled), and (B) shows the infected amniotic fluid sample. FIG. 7 shows that ceruloplasmin (~130 KDa) and calgranulin (~16 KDa) are expressed at a higher level in the infected amniotic fluid than control amniotic fluid.

Example 10

Figure 8:
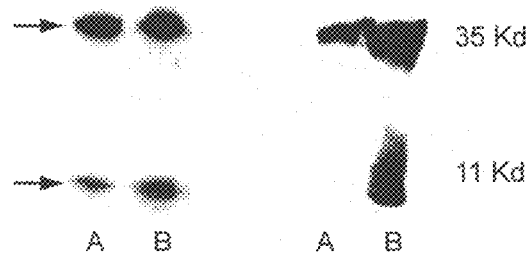
FIG. 8 shows the detection of differential protein expression in the human amniotic fluid and maternal serum. A) control sample (pooled); B) infected sample (pooled).

Detection of Differential Protein Expression in the Human Amniotic Fluid and Maternal Serum It has been examined if the differentially expressed proteins in the amniotic fluid can be used as a lead to measure similar proteins in the maternal serum. This will enable to develop rapid and non-invasive testing for diagnoses and monitoring. The results are shown in FIG. 8, where (A) is the control sample (pooled), and (B) is the infected sample (pooled). FIG. 8 shows that an IGFBP-1 smaller proteolytic fragment is consistently differentially expressed both in AF and maternal serum in response to intrauterine infection.

Example 11

Protein Microarray Analysis of Amniotic Fluid from Intrauterine Infection

Antibodies: IGFBP-1 (DSL); complement C3, Desmin, neutrophil elastase, NSE antibody (DAKO); calgranulin, ceruloplasmin, TIMP-1, plastin and profiling (Santa Cruz).

Antibody spotting: antibodies were dissolved in 40% glycerol, 60% PBS, pH 7.5 at a concentration of 100 µg/ml and were spotted on aldehyde slides using a Arrayer (Cartesian).

Following a 3 hr. incubation in a humid chamber at room temperature, the slides were incubated for one hour in a solution of PBS, pH 7.5 containing 1% BSA (w/v at room temperature with gentle agitation.

Figure 9:
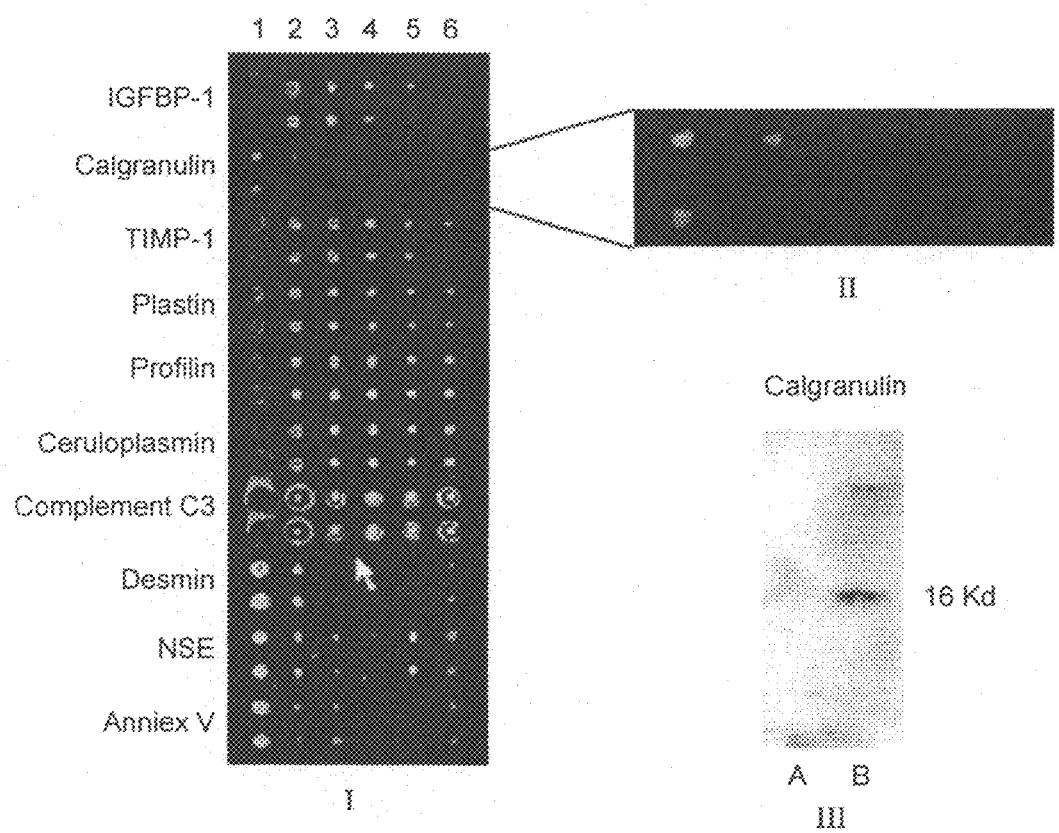
FIG. 9 shows the detection of differentially expressed proteins in maternal serum using protein arrays. 1) pseudocolor image of the protein array showing the binding of corresponding proteins with their antibodies; 2) enlarged area of the array; 3) Western blot of calgranulin IP.

Biotinylation of proteins: Biotin-NHS was dissolved in DD water at 50 mg/l. 10 ul of this solution was added into maternal serum protein solution (5 mg/ml in 10 mM PB, pH8.5) and incubated for 3 hours on a shaker. 5 ul of ethanolamine was added to stop the reaction. Biotinylated proteins were diluted in 200 ul of TNB buffer and added to antibody arrays and incubated overnight at 4 C. Following three washes in TNT buffer, streptavidin-HRP was added and incubated for 30 minutes at room temperature. Antigen-Antibody interaction was detected using Cy5-tyramide fluorescence. Slides were scanned on a PE fluorescent scanner for quantification. Images of control and infected slides were overlayed using a image analysis program to generate a pseudocolor representation for relative abundance. The results are shown in FIG. 9, which is a pseudocolor image of the protein array showing the binding of corresponding proteins with their antibodies. Green color represents infected sample, red color represents control sample. Part II is an enlarged area of the array showing that calgranulin expression (green) is higher in the infected serum sample. Part III is a western blot of calgranulin IP showing similar increased expression in the infected amniotic fluid sample.

Example 12

Figure 13:
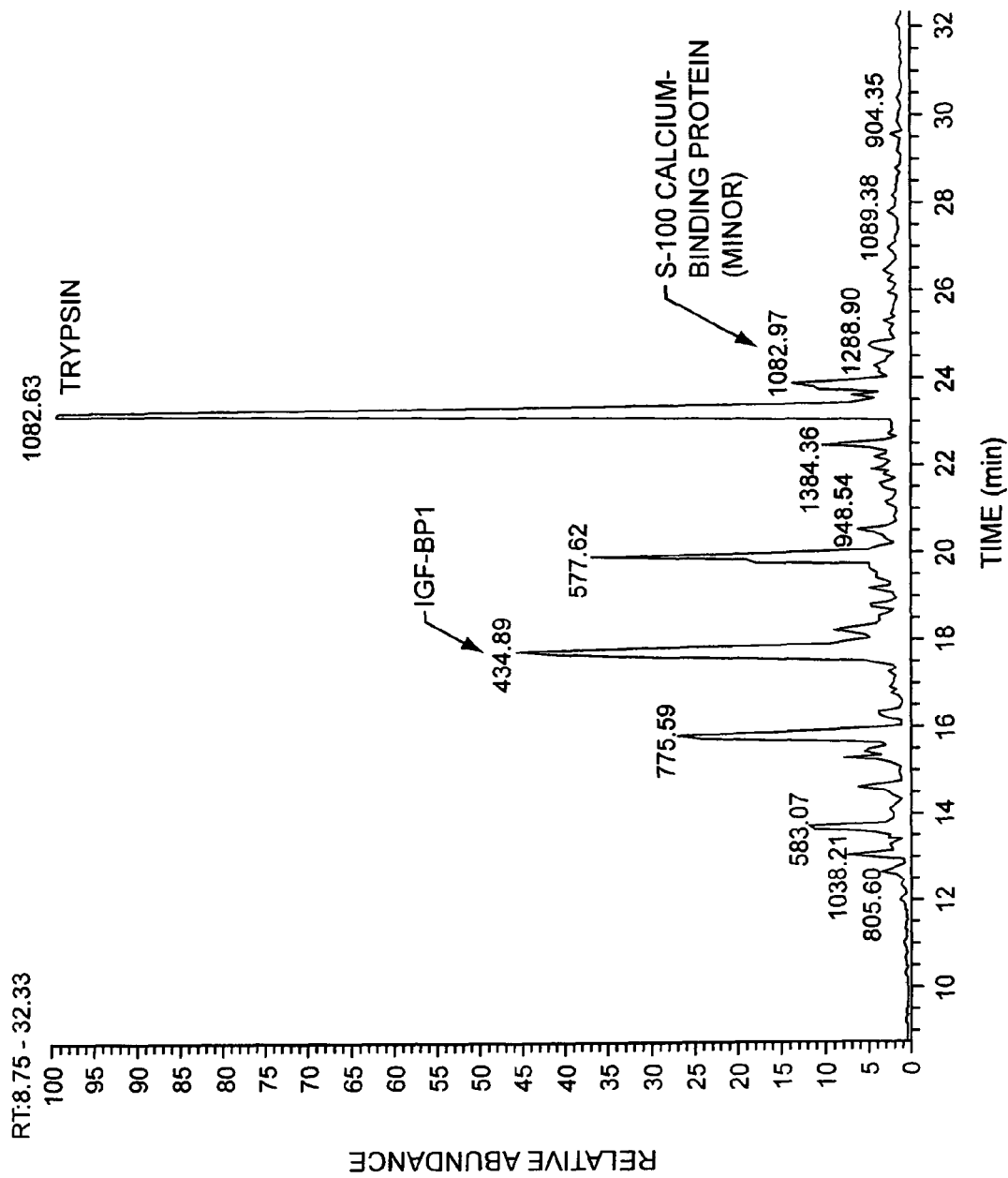
FIG. 13. LCQ™-MS profile of trypsin digestion of 10.5-11 kD ID gel band from infected amniotic fluid. LCQ™-MS showing parent ions representing potential proteins present in the sample.

Further Analysis of Proteins Represented in the Unique Diagnostic Signature of Infected Amniotic Fluid It has been demonstrated that the SELDI-TOF profiles of control and infected amniotic fluid show a unique signature in the mass range of 10-12 KDa (FIGS. 1, 2 and 3), representative of positively infected sample. The control and infected amniotic fluid resolved on a 1-D gel (FIG. 5) also shows bands in the mass range of 10-12 KDa that are more abundant in the pooled or independent infected amniotic fluid samples. Isolation of these 1-D gel bands and further analysis using LCQ™-MS as shown in FIG. 13, identified peptides representative of IGF-BR-1 and S-100 calcium binding proteins.

Western blot analysis of control and infected amniotic fluid using an anti-IGF-BP1 antibody as shown in FIG. 8, also demonstrates the differential expression of a proteolytic fragment (~11 KDa) in infection.

Sequencing of the amniotic fluid polypeptides also identified the presence of IGF-BP1 and calgranulins in the infected amniotic fluid (Table 3).

The sequence of the identified novel proteolytic fragment of IGFBP-1 is shown in FIG. 12. (SEQ ID NO: 1). In the Figure, the peptide sequences found in samples "0426seq_HI_12" and "0425seq_HI-113" following 1-D gel electrophoresis, trypsin digestion and MS/MS analysis of infected amniotic fluid are shown in lower case. (SEQ ID Nos: 2 and 3). The proteolytic fragment of IGF-BP-1 detected in 1-D gels (low molecular weight range, FIG. 5), Western blots (FIG. 6), and MS/MS analysis (FIG. 13) of trypsin digested ~10.5-12 KDa band from infected amniotic fluid, is represented in the region of the underlined sequence. (SEQ ID NO: 4).

Indeed, MS/MS analysis and sequence search results demonstrated that the parent ion 434.89 in the mass spectrum shown in FIG. 13 represents an IGF-BP-1 sequence (RSPG-SPEIR), which is also shown in the FIG. 12 sequence map of the IGF-BP-1 proteolytic fragment. The parent ion 1082.97 represents S-100 calcium binding proteins (i.e., Calgranulins A and B), also independently identified by de novo sequencing of AF (Tables 2 and 3).

Figure 14:
FIG. 14. Mass spectrum for the 17.55-18.21 minute retention time peak shown in FIG. 13.

FIG. 14 shows mass spectrum for the 17.55-18.21 minute retention time peak shown in FIG. 13. It is apparent that the dominate peak appears at mass 434.9.

Figure 15:
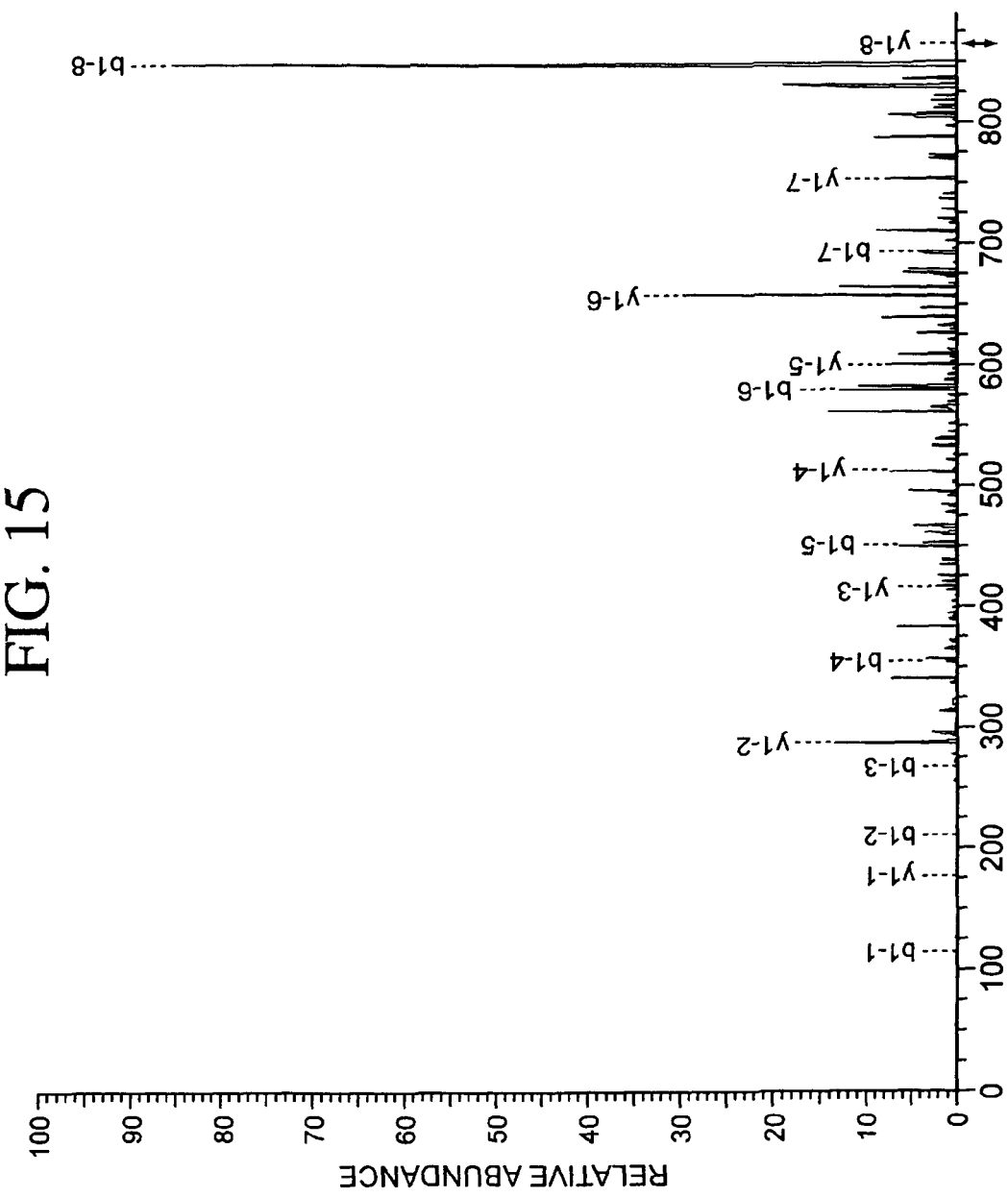
FIG. 15. MS/MS spectrum for the parent ion of the 434.9 peak shown in FIG. 14.

FIG. 15 shows the MS/MS spectrum for the parent ion of the 434.9 peak shown in FIG. 14. Based on database search, the parent ion corresponds to a partial sequence of IGFBP-1.

Example 13

Diagnostic Profiles Characteristic of Chromosomal Aneuploidies

The utility of proteomic profiling was examined to identify trisomy-21 more accurately, using maternal serum screening. This study was performed with a panel of (control (n=6), trisomy-21 (n=6) and trisomy-18 (n=4), well-characterized maternal serum samples (matching amniotic fluid samples for the same cases were tested by standard chromosomal mapping method and positively confirmed the presence of trisomies) and analyzed using SELDI-TOF methodology as described above for the intrauterine infection model.

Figure 10:
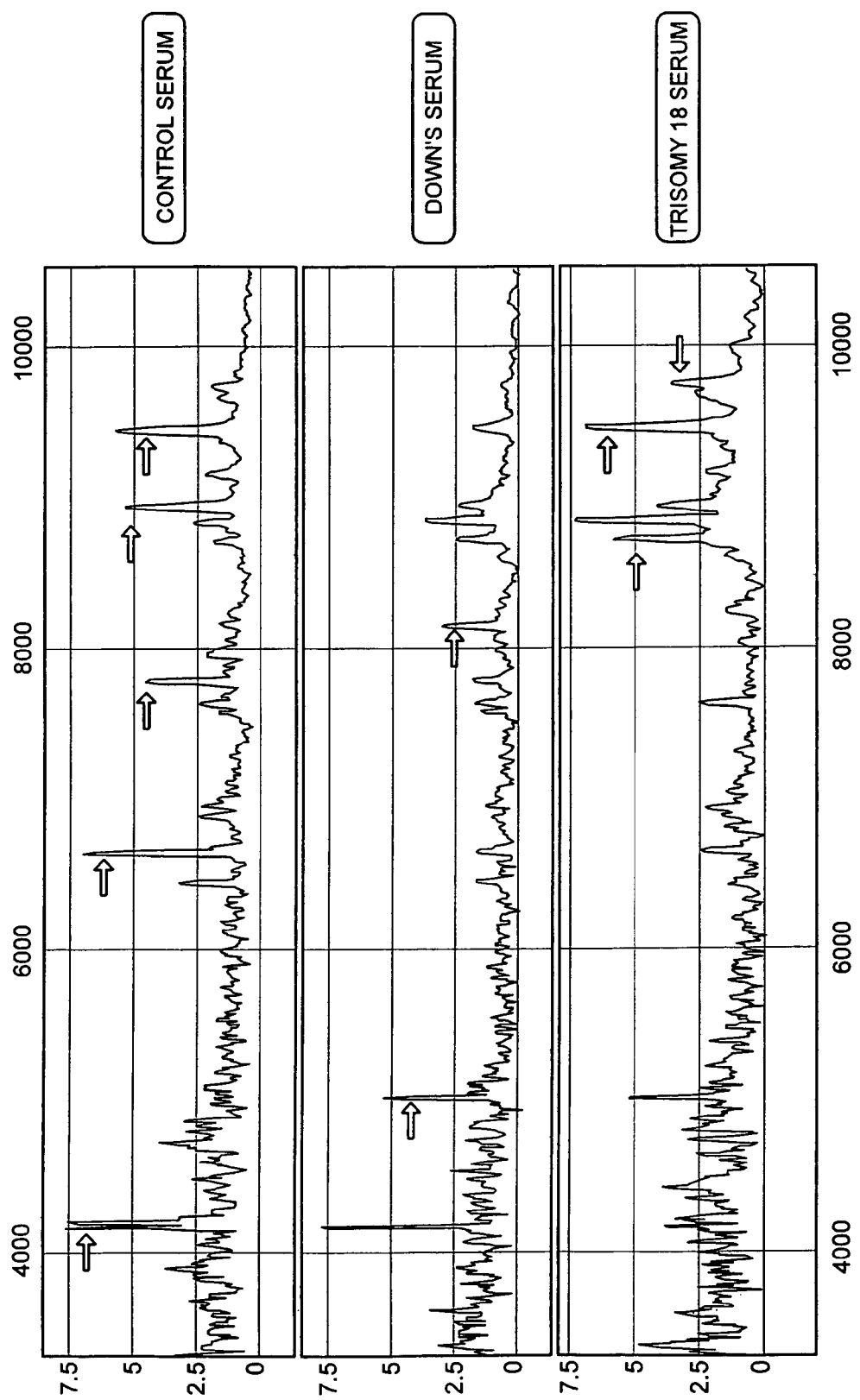
FIG. 10 shows differential protein expression patterns in the maternal serum with unique profiles to distinguish trisomies.

FIG. 10 shows differential protein expression patterns in the maternal serum with unique profiles to distinguish trisomies. One microgram of maternal serum (after removal of albumin and immunoglobulins using protein separation columns, BioRad technologies) was used to perform SELDI-TOF analysis of maternal serum extracts bound to chemically defined Normal Phase chip arrays as described in the methods. Whole spectrum collected at 235-laser intensity showing the differences in the peak intensities. A) Control serum; B) trisomy-21 (Down's) serum; C) trisomy-18 serum. Detailed spectrum showing the differences in the 4-15 KDa region unique for each case. Arrows indicate diagnostic peaks that can be used in a combination to formulate an algorithm to develop diagnostic screening tests.

Example 14

Protocols used in Comprehensive Proteomic Analysis of Human Cervical-Vaginal Fluid Sample Collection and Processing This study was approved by the IRB committee at Oregon Health & Science University. All subjects were identified prospectively and gave informed written consent to participate in the study. Seven subjects were recruited, at a mean gestational age (GA) of 18.5 weeks with a standard deviation of +/−2.1 weeks. CVF samples were collected by placing 2 sterile 6-inch Dacron-tipped plastic applicators (Solon, Skowhegan, Me.) into the posterior vaginal fornix and rotating them for 15 seconds during sterile speculum examination. Following collection, protein was extracted into phosphate-buffered saline with a protease inhibitor cocktail (Roche Diagnostics, Alameda, Ca.). Samples were spun down after extraction to remove any debris and cellular material, and the supernatant was stored at −70° C. Two pooled samples (GA 16-18 weeks, 19-21 weeks) were prepared (n=3 for each pool) by combining GA-matched samples. A total of 530 µg of protein from each pooled sample was acetone-precipitated and dissolved in 10 mM Tris, pH 8.5, for 2D-LC analysis. 100 µg each from two individual samples was used for one-dimensional gel electrophoresis (1DGE).

Multidimensional Liquid Chromatography (2D-LC).

530 µg of protein from each pooled sample was dried and dissolved in 100 µl of digestion buffer containing 8 M urea, 1 M Tris base, 100 mM methylamine, and 10 mM $CaCl_2$ (pH 8.5). Samples were reduced and alkylated by first incubating at 50° C. in 12.5 µl of 0.9 M DTT for 15 min and, then, in 25 µl of 1.0 M iodoacetamide in dark at room temperature for another 15 min. An additional 12.5 µl of 0.9 M DTT along with 210 µl of water and 1N NaOH was added to the solution to adjust its pH to 8.5. Sampels were digested with 40 µl of 1 mg/ml trypsin (Promega) stock solution overnight at 37° C. Digestion was stopped with 40 µl of formic acid and desalted using C18 SepPak Plus cartridges. Digests (1 ml) were injected onto a polysulfoethyl strong cation exchange column (2.1-mm ID×100 mm, 5-µm particle size and 300-Å pore size (The Nest Group, Southborough, Mass.) and fractionated using an HPLC equipped with a UV detector and a fraction collector. Solvent A was 10 mM potassium phosphate (pH 3) with 25% acetonitrile (ACN), and solvent B was 10 mM potassium phosphate (pH 3), 350 mM KCl with 25% ACN. A 95-min. gradient at a flow rate of 200 µl/min was employed for fractionation of peptides. A total of 80 fractions were collected, evaporated and resuspended in 100 µl of 0.1% TFA for desalting using a 96-well Vydac C18 silica spin plate (The Nest Group, Southborough, Mass.). Fractions were eluted in 80% ACN/0.1% formic acid (FA), evaporated, and resuspended in 20 µl of 5% FA, and 5 µl of each fraction was analyzed on a Q-Tof-2 mass spectrometer connected to a CapLC (Waters, Milford, Mass.).

1-Dimensional (1-D) Gel Electrophoresis Analysis.

100 µg of protein from each of two samples was reduced with iodoacetamide and resolved on a Tris-tricine, 10-20% gradient SDS-PAGE gel. The gel was stained with Coomassie blue R-250. Each lane was sliced into 25 individual bands, destained, and digested in-gel with trypsin for 24 hours at 37° C. The peptides were extracted in ammonium bicarbonate and then filtered with a 0.22 µm MultiScreen filter plate (Millipore, Billerica, Mass.). Filtered solutions were dried down and reconstituted in 5% formic acid and analyzed on a Q-Tof-2 mass spectrometer equipped with a CapLC (Waters, Inc., Milford, Mass.).

Mass Spectrometry.

2D-LC fractions and gel digests were further separated using a Nanoease C18 75-µm ID×15-cm fused silica capillary column (Waters Inc., Milford, Mass.) and a 95-min water/ACN gradient. The mass spectrometer was calibrated using Glu1Fibrinopeptide B. An MS/MSMS survey method was used to acquire spectra. Masses from m/z 400 to 1500 were scanned for MS survey and masses from m/z 50 to 1900 for MSMS. A total of 10,824 MS/MS spectra were acquired from the 2D-LC fractions. Raw MS/MS spectra were pre-processed with ProteinLynx Global Server v.2.1 software (Waters Inc., Milford, Mass.).

Protein and Peptide Identification.

Figure 16A:
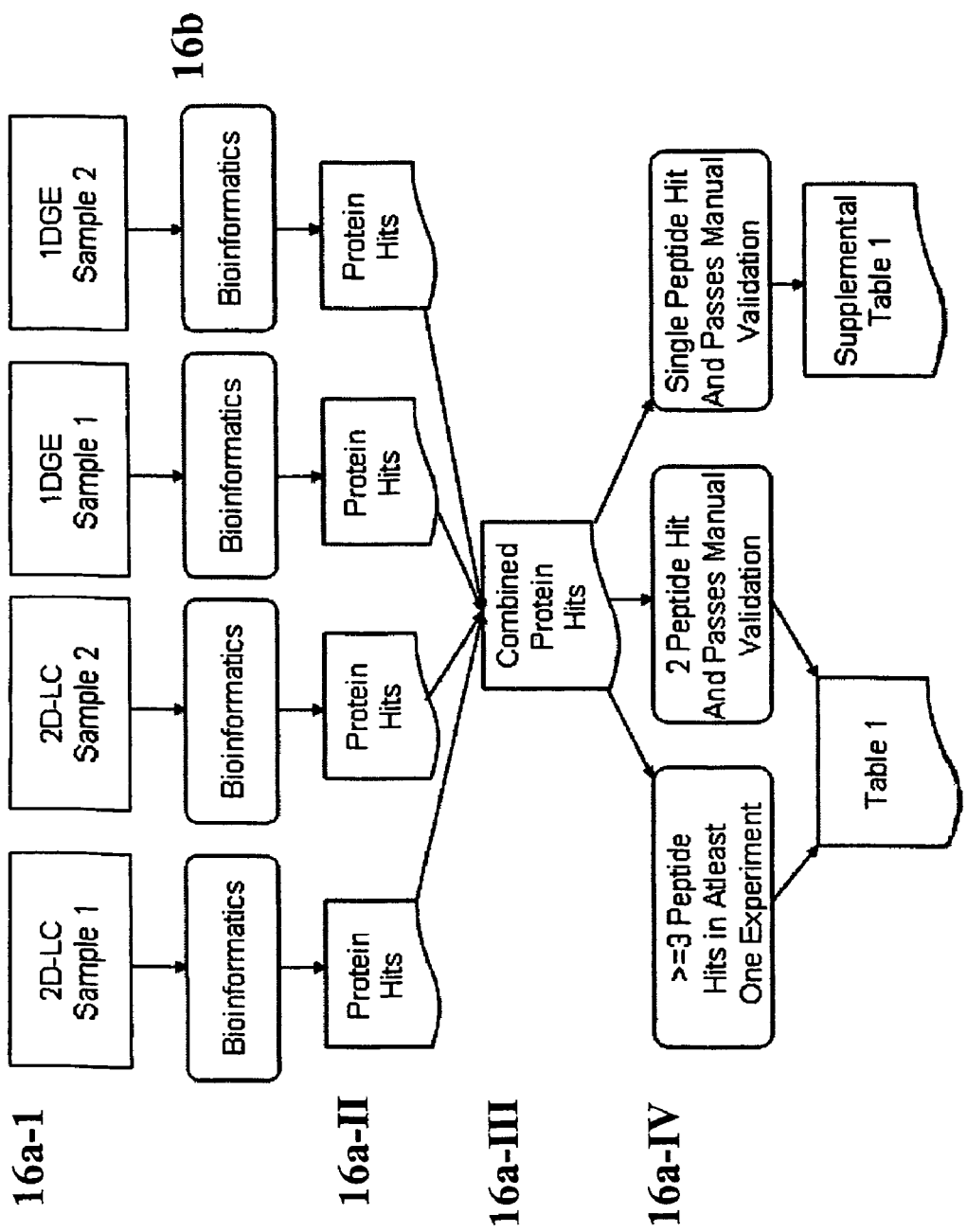
FIG. 16. LC/MS/MS spectra acquired from all samples (16a-I) were processed using the bioinformatics workflow shown in FIG. 16b. Protein identifications (16a-II) from individual samples were combined in to a comprehensive protein list (16a-III). All proteins with at least three unique peptide hits from the comprehensive list were accepted into Table 4 without manual validation (16a-IV). Proteins in the comprehensive list that had at most two unique peptide hits were manually validated using the rules outlined in the methods section (16a-IV). All proteins that have two unique peptide hits that passed manual validation were added to Table 4 (16a-IV). Proteins with a single peptide hit that passed manual validation were added to Table 5 (FIGS. 16a-IV).
FIG. 16b shows the bioinformatics workflow for protein and peptide identification. LC/MS/MS spectra from a sample were deisotoped and centrioded (16b-I). Peptides and proteins in the sample were identified by searching the preprocessed MS/MS spectra against a combined protein database (see methods section) using TurboSequest (ThermoFinnigan, Waltham, Mass.), X! Tandem (Fenyo, D.; et al., *Anal Chem* 2003, 75, (4), 768-74), and OpenSea Searle, B. C., et al., *Anal Chem* 2004, 76, (8), 2220-30; Searle, B. C. et al., *J Proteome Res* 2005, 4, (2), 546-54.). Peptide and protein hits from all three programs were combined using Scaffold software (Proteome Software, Portland, Oreg.).
Figure 16B:
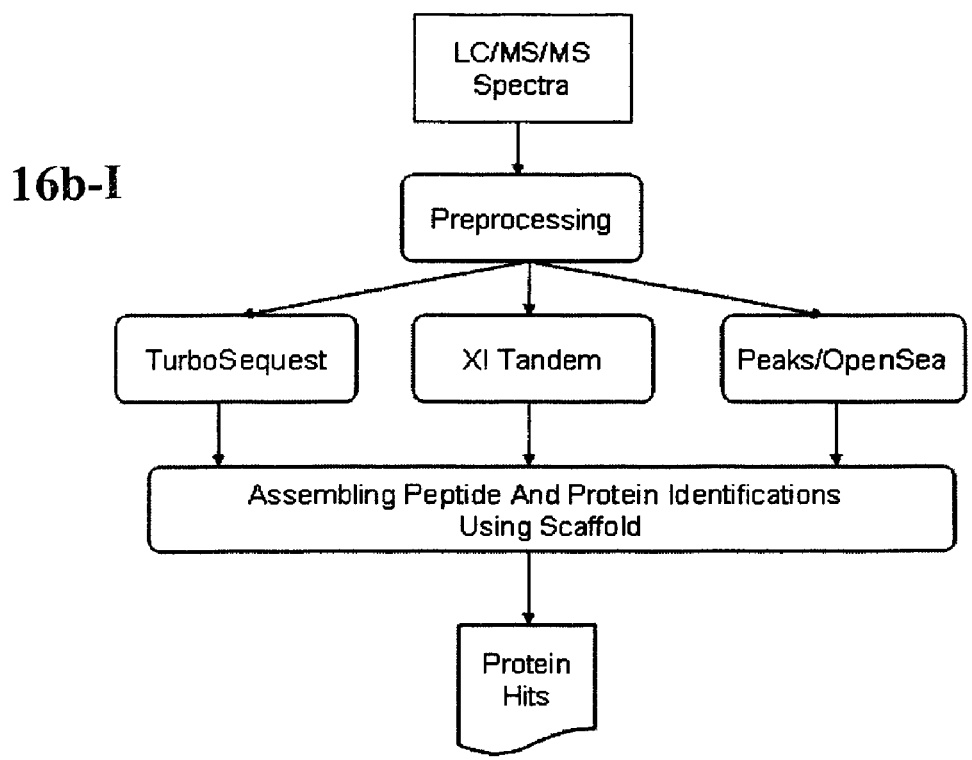

FIGS. 16A and B show the protein and peptide identification workflow. Raw MS/MS spectra from either 2D-LC samples or 1DGE samples were further processed by de-isotoping and centroiding the raw data. Preprocessed MS/MS spectra from different fractions of the sample were pooled for further analysis. Peptides present in the sample were identified by matching pooled MS/MS spectra to a combined protein database containing known contaminants and forward and reverse entries from the SwissProt™ database (version 46.6) selected for human species. Peptide identification searches were performed using three independent search engines: TurboSequest (ThermoFinnigan, Waltham, Mass.), X! Tandem, and OpenSea. Sequest™ and X! Tandem are database search engines that match experimental spectra to theoretical spectra generated from a theoretical enzymatic digest of the protein database. OpenSea is a de novo sequence-based search engine that performs an error-tolerant matching between inexact de novo sequences and protein sequences in the database. Peaks software (Bioinformatics Solutions, Ontario, Calif.) was used to provide de novo sequences to the OpenSea search engine. The reduction and alkylation step of the sample processing introduces a fixed cabamidomethylation modification on all cysteine residues in the proteins. Hence, all the programs were configured to use the modified cysteine mass (160.03 Da) as standard mass for all cysteine residues. The de novo sequencer and all search engines were configured to use monoisotopic masses to calculate parent and fragment ion masses. Peaks software was configured to use 0.2 Da and 0.1 Da for parent ion and fragment ion mass tolerances, respectively. The top five candidate de novo sequences reported by Peaks software for each MS/MS spectra were fed to OpenSea for error-tolerant database matching. OpenSea was configured to use 0.25 Da as the fragment ion mass tolerance. For Sequest™ searches, a parent ion mass tolerance of 2.0 Da was used to calculate parent ion mass. X! Tandem was configured to use mass tolerances of 0.5 Da and 0.25 Da for parent and fragment ions, respectively. To speed up Sequest™ searches, it was not configured to search for any variable modifications. In turn, based on our prior experience, X! Tandem and OpenSea were configured to search for variable modifications (i.e., oxidation of methionine, pyroglutamic acid formation at the N terminus, carbamylation of the N terminus, dehydration of internal serine, threonine, aspartic acid, and glutamic acid residues, and deamidation intermediates of glutamine and asparagine) that could have been present in the MS/MS spectra either as artifacts from sample processing or peptide fragmentation mechanisms. Peptide identifications from individual search engines were combined into protein identifications using probabilistic protein identification algorithms implemented in Scaffold (Version: 1.3.2, Proteome Software, Portland, Oreg.).

Protein identifications that had at least one unique, highly confident (probability $\geq 0.9$) peptide identification were considered likely to be present in the sample. A protein was accepted into the comprehensive list without manual validation if it was confidently identified in at least one of the samples with three highly confident unique peptide hits. Proteins that did not meet this filtering criterion were manually validated. Manual validation was performed using all criteria listed in reference (Wilmarth, P. A. et al., *J Proteome Res* 2004, 3, (5), 1017-23), enhanced fragmentation C-terminal to aspartic acid (Gu, C., et al., *Anal Chem* 2000, 72, (23), 5804-13), and the presence of low-mass immonium ions (proline, valine, isoleucine, leucine, histidine, phenylalanine, and tyrosine) whenever these residues were present in the peptide sequence.

Example 15

Comprehensive Proteomic Analysis of Human Cervical-Vaginal Fluid (CVF)

Analysis

Following the protocols described in Example 14, human CVF was analyzed using two different proteomics techniques: 2D-LC and 1DGE. Two pooled samples were trypsinized and subjected to SCX fractionation, resulting in a total of 40 fractions. Two individual samples were fractionated using 1DGE and the resulting bands were subject to in-gel trypsin digestion. A total of 27,397 MS/MS spectra were collected by analyzing all fractions on a LC-ESI-qTOF mass spectrometer. All MS/MS spectra were searched using Sequest™, X! Tandem, and OpenSea. Peptide identifications from all programs were assembled into protein identifications using Scaffold.

A total of 831 proteins at the single peptide identification level were identified when the lowest possible peptide identification probability thresholds (0.2) were employed. 30% of the identified proteins were false-positive identifications (reverse database entries). Several protein isoforms and proteins that were subsets of other proteins were present in the list. Furthermore, the low scoring (peptide identification probability <0.9) peptide identifications didn't manifest the necessary characteristics to pass the manual validation criterion listed in the methods section. A large proportion (54%) of the protein hits were also single-peptide identifications. Since single-peptide protein identifications are more likely to be false-positives and, therefore, insufficient for protein quantitation and inferring pathobiological function, a peptide identification probability of 0.9 was established as a minimal criterion to consider only highly confident peptide and protein identifications. Degenerate protein identifications were grouped together and reported as one entry, and any proteins that were subsets of other proteins were removed from the analysis.

A total of 206 unique proteins from all experiments were mapped to 55% of the experimental MS/MS spectra after applying the filtering described above. 3% and 15% of the identified proteins in the list are false-positive identifications and single-peptide identifications, respectively. A total of 177 proteins remained after removing contaminants such as keratins, trypsin and bovine casein. 105 proteins that had at least three unique peptide hits in at least one of the experiments were accepted without further manual validation. The remaining protein identifications were manually validated using the criteria listed in the methods section. An additional 45 proteins passed manual validation; 29 of them had at least two unique peptide hits, and 16 had a single peptide hit. This increased the number of proteins that were identified with at least two distinct peptide hits to 134, and with at least one distinct peptide hit to 150.

In order to ensure the reliability of protein identifications, all searches were performed with a combined database that was constructed with reverse entries of the database appended at the end of the forward sequences. The number of reverse database entries that passed all criteria for protein identification was considered to reflect the reliability of the protein identification criteria outlined in the methods section. Since none of the reverse entries met these criteria, the reliability of the protein identifications is estimated to be 100%.

MS/MS spectral counting is generally considered to be a sensitive and semi-quantitative method for measuring protein abundances (Old, W. M., et al., *Mol Cell Proteomics.* 2005, 4, (10), 1487-502. Epub 2005 Jun. 23). However, homologous proteins pose a greater problem for accurate MS/MS spectral count representation due to their high sequence similarity. In order to avoid either inflation or deflation of MS/MS spectral counts of homologous proteins, a final level of filtering was performed to combine MS/MS spectral counts of protein homologues that share greater than 50% sequence homology. For example, squamous cell carcinoma 1 and 2 antigens share greater than 90% sequence homology. Although we have identified peptide hits that suggest the presence of both proteins in the sample, their MS/MS spectral counts were combined and represented as a single entry. Proteins that were combined under this criterion were IGHA1 and IGHA2, IGHG1, IGHG2 and IGHG4, SCCA1 and SCAA2, and SPR2A, SPR2B, and SPR2D. MS/MS spectral counts of peptides common to proteins that do not share high sequence homology were pulled towards the protein that was considered most likely (greater number of peptide hits) to be present in the sample. Finally, a combined MS/MS spectral count for each protein was established by combining the respective MS/MS spectral counts of the protein in all experiments. The combined MS/MS spectral count was normalized by the total number (12,827) of MS/MS spectra that were matched to non-contaminant proteins at a single-peptide probability threshold of 0.9 in all experiments. The normalized spectral counts are not strictly quantitative, but they can be used to gauge the relative abundance of the proteins present in a sample with respect to each other.

The final 134 proteins that had at least two unique peptide hits and passed manual validation are listed in attached Table 4 by their decreasing order of normalized MS/MS spectral counts.

Human CVF proteome. Proteins having at least two peptide identifications found in human CVF are listed with their SwissProt™/TrEmbl accession number[a] and description. Homologous protein identifications are grouped together as a single entry. Theoretical PIs[b] and monoisotopic molecular weights[c] were calculated using the CalPI/MW tool (Gasteiger, E. et al., Nucleic Acids Res 2003, 31, (13), 3784-

8) on the SwissProt™ website. Functional annotation[d] was performed using the DAVID database (Dennis, G., Jr. et al., Genome Biol 2003, 4, (5), P3) bioinformatics resource. Combined spectral counts for each of the protein identifications from both 1DGE and 2D-LC experiments were normalized[e] by the total number (12,827) of MS/MS spectra that were matched (non-contaminant proteins) at a single-peptide probability threshold of 0.9 in all samples. The proteins in the table are ordered by decreasing normalized spectral counts. [f]Proteins that were also seen in either AF (A) and/or serum (S) are marked accordingly.

The 16 proteins that had a single peptide hit and passed the manual validation are listed in attached Table 5 by their decreasing order of combined MS/MS spectral counts. Thus, in Table 5 single-peptide protein identifications found in human CVF that passed the manual validation criteria listed in the Methods section are enumerated with their SwissProt™/TrEmbl accession number[a] and description. Homologous protein identifications are grouped together as a single entry. Theoretical PIs[b] and monoisotopic molecular weights[c] were calculated using the CalPI/MW tool on the SwissProt™ website. Functional annotation[d] was performed using the DAVID database bioinformatics resource. The proteins in the table are ordered by decreasing order of combined spectral counts[e] for each of the protein identifications from both 1DGE and 2D-LC experiments. [f]Proteins that were also seen in either AF (A) and/or serum (S) are marked accordingly (see text for discussion).

Proteins listed in Tables 4 and 5 are functionally annotated based on the classification from the Database for Annotation, Visualization and Integrated Discovery (DAVID) (Dennis, G., Jr., et al., *Genome Biol* 2003, 4, (5), P3).

The CVF proteins found in this study were cross-referenced with the highly confident HUPO plasma proteome (Anderson, N. L. et al., Mol Cell Proteomics 2004, 3, (4), 311-26; States, D. J. et al., Nat Biotechnol 2006, 24, (3), 333-8) and AF proteome (Park, S. J. et al., Proteomics 2006, 6, (1), 349-63; Michel, P. E. et al., Electrophoresis 2006, 27, (5-6), 1169-81). The HUPO plasma proteome was further curated by converting the IPI database protein accessions into SwissProt™/TrEmbl protein accessions wherever possible and removing common contaminants like keratin. Protein isoforms reported in the HUPO plasma proteome were collapsed into a single protein entry due to the lack of direct MS/MS spectral evidence that could resolve different isoforms. The curated HUPO plasma proteome (526 proteins) was combined with the 195 proteins listed in Anderson et al. 2004, supra, to make a non-redundant, highly confident HUPO plasma proteome (data not shown). CVF protein identifications were compared to the curated HUPO plasma proteome and the AF proteome based on their SwissProt™/TrEmbl protein annotation and are marked accordingly (A-found in amniotic fluid, S-found in serum) in the last column of the corresponding tables.

Discussion

Figure 17:
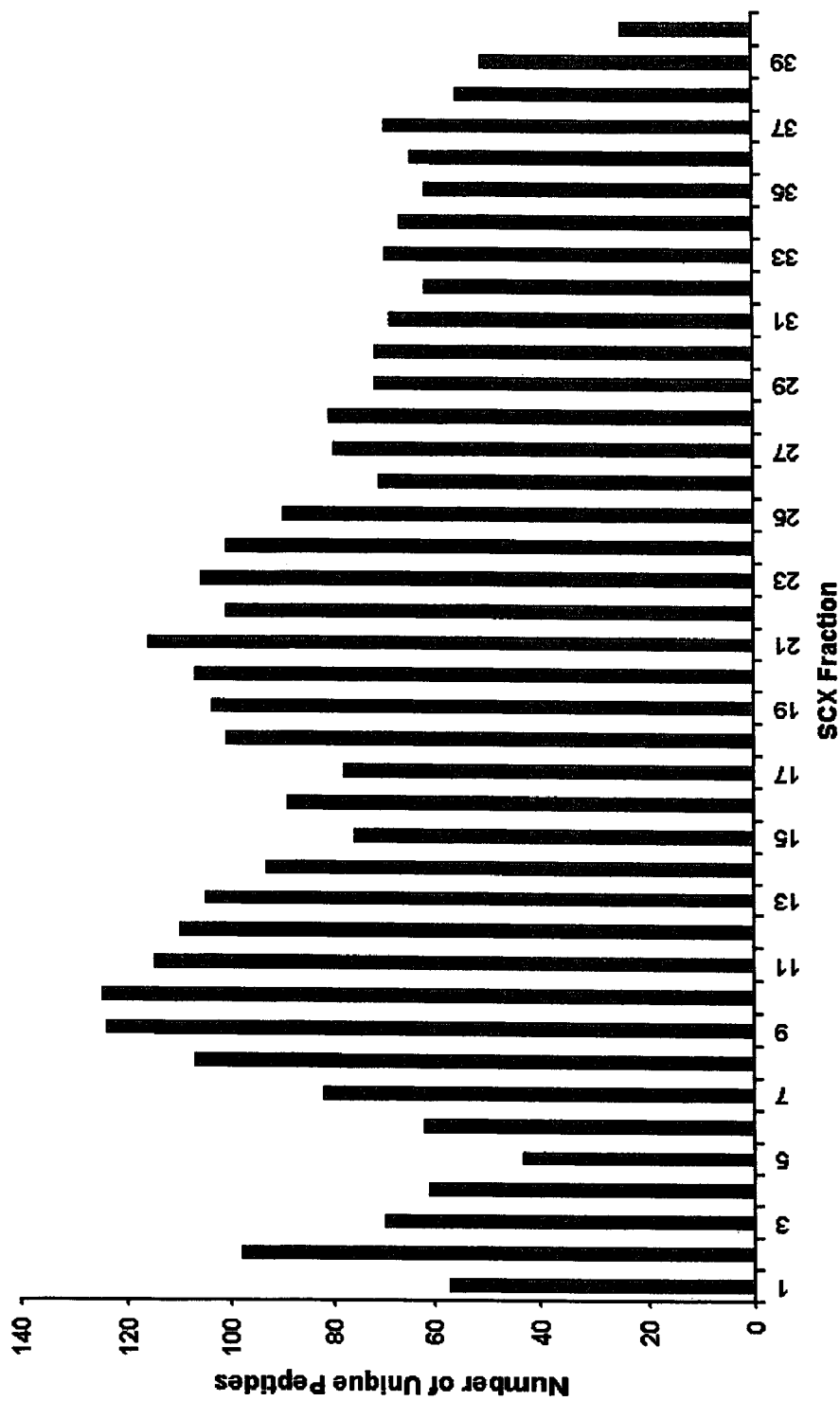
FIG. 17. Distribution of the number of unique peptides identified in SCX fractions. The total number of unique peptides identified per fraction in human CVF 2D-LC samples shows the advantage of the technique over traditional gel-based electrophoresis techniques.

The 2D-LC technique is known to provide enhanced fractionation compared to traditional gel-based electrophoresis methods. FIG. 17 shows the number of unique peptides identified per SCX fraction from the 2D-LC fractionation. Clearly, the enhanced fractionation of the technique, when coupled with RP-HPLC, contributed to the identification of greater number of unique peptides per SCX fraction and, overall, a large number of protein identifications in the sample.

Figure 18A:
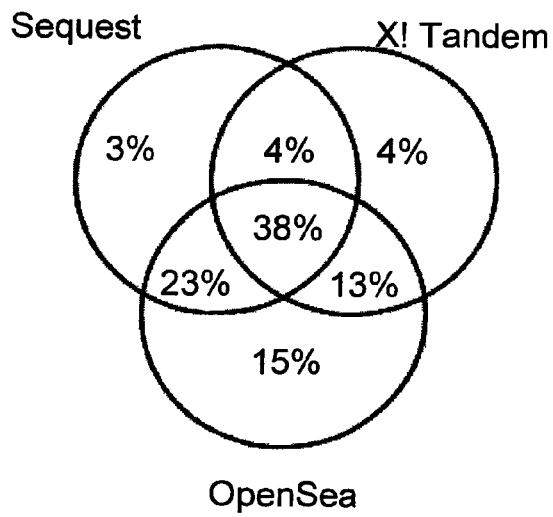
FIG. 18. Spectral and protein identification overlap between different search engines. (A) A total of 9,507 MS/MS spectra from a human CVF 2D-LC experiment were searched with Sequest™, X! Tandem, and OpenSea search engines. When three independent search engines are used, a total of 5601 (59%) MS/MS spectra in the sample were matched to proteins at a two unique peptide identification threshold. The distribution of percentage of identified spectra (above threshold) between search engines shows that using multiple independent search engines identified more MS/MS spectra in a sample. (B) A total of 118 candidate proteins were identified when all three search engines were used to analyze MS/MS spectra from a single human CVF 2D-LC sample. The distribution of number of candidate protein hits among three search engines shows that using multiple independent search engines identified more proteins.
Figure 18B:
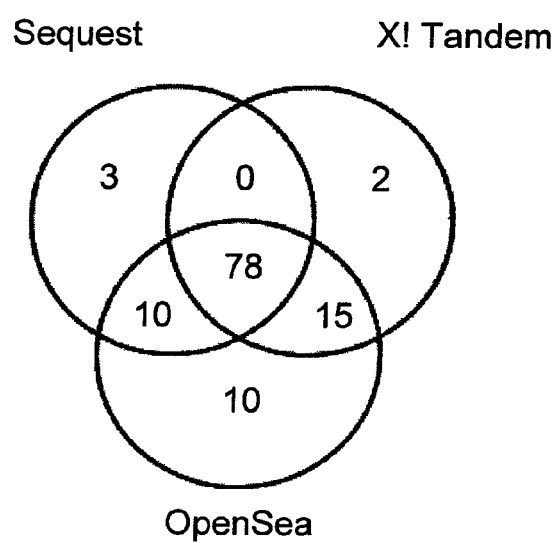

Recent studies have shown that a MS/MS dataset can be thoroughly characterized by using multiple search engines to identify the peptides in that dataset (Resing, K. A. et al., Anal Chem 2004, 76, (13), 3556-68). When different search engines are used to identify peptides in a dataset, they identify different sets of MS/MS spectra due to the difference in heuristics that are encoded in the corresponding search engines. Thus, a combination of different search engine results on the same dataset gives a more comprehensive list of peptide identifications. In this study, we have used three different search engines to identify the peptides present in the samples: Sequest™, X! Tandem, and OpenSea. Using this combinatorial approach, we were able to identify 59% of the acquired MS/MS spectra in one of the 2D-LC experiments. The breakdown of percentages of spectral identifications (above the score cutoffs of the corresponding programs) between the three programs (FIG. 18A) shows that only 38% of spectra were identified by all three programs, whereas 21% of spectra were identified uniquely by only one of the programs. Interestingly, 15% of the spectra were identified solely by the OpenSea search engine. This is due to the ability of OpenSea to identify spectra with missing fragment ions and unexpected sequence modifications. The total number of candidate proteins identified in the sample was also increased due to the combinatorial search technique. Among a total of 118 candidate protein identifications as shown in FIG. 18B, 66% were identified by all three programs, whereas 13% were identified uniquely by only one of the programs. Thus, the combinatorial search technique employed in this study identified more peptide and candidate protein identifications from the datasets.

Figure 19:
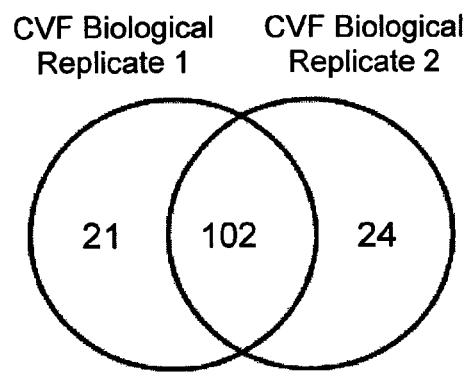
FIG. 19. Protein ID distribution in biological replicates. The Venn diagram shows the distribution of protein identifications between CVF biological replicates that were analyzed using 2D-LC. Among a total of 147 identified proteins, 102 proteins were present in both samples, and 45 proteins were present in one sample or the other.
Figure 20:
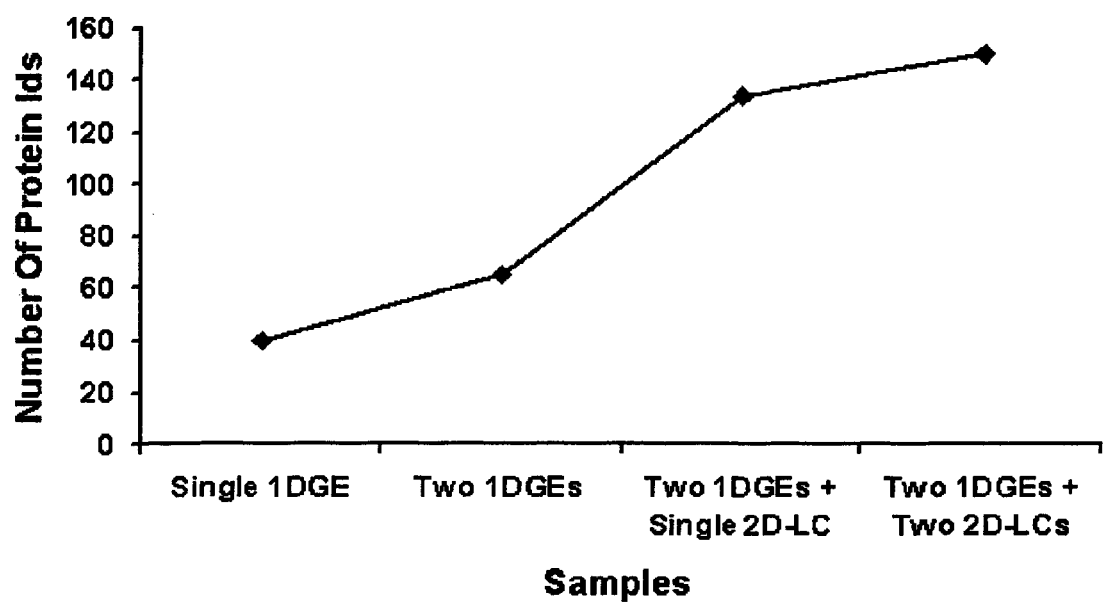
FIG. 20. Protein ID distribution in different analytical approaches. The protein identification rate increased by addition of biological replicates and experimental replicates to the analysis. Among a total of 150 proteins, 62 proteins were detected by both 1DGE and 2D-LC techniques, 85 were only detected by 2D-LC alone, and 3 (all of them having at least 2 unique peptide identifications) were detected by 1DGE alone.

The composition of various body fluids changes over time, especially CVF during gestation. The overlap of proteins identified in two biological replicates from 2D-LC experiments is shown in FIG. 19. 69% of the proteins were identified in both biological replicates, whereas 31% of the proteins were identified solely in one of the replicates. This was not unexpected, as both samples differed by two weeks of GA. The random sampling of low-abundance proteins by the mass spectrometer might also have contributed to the above-mentioned difference. Among 65 proteins that were identified by 1DGE technical replicates, 69% were identified in both replicates, whereas 31% were identified uniquely in one of the replicates. This underscores the importance of having biological and technical replicates when characterizing proteomes. The overall increase in the number of protein identifications with the addition of experiments to the analysis is summarized in FIG. 20. A total of 40 proteins were identified by our protein identification criteria when using a single 1DGE experiment. An increase of 15, 69, and 16 protein identifications was observed when a single 1DGE technical replicate, 2D-LC experiment, and its corresponding biological replicate were added to the analysis, respectively. This is the first comprehensive proteomics study that has employed a variety of analysis programs, technical replicates, biological replicates, and experimental methods to characterize the human CVF proteome.

Figure 21:
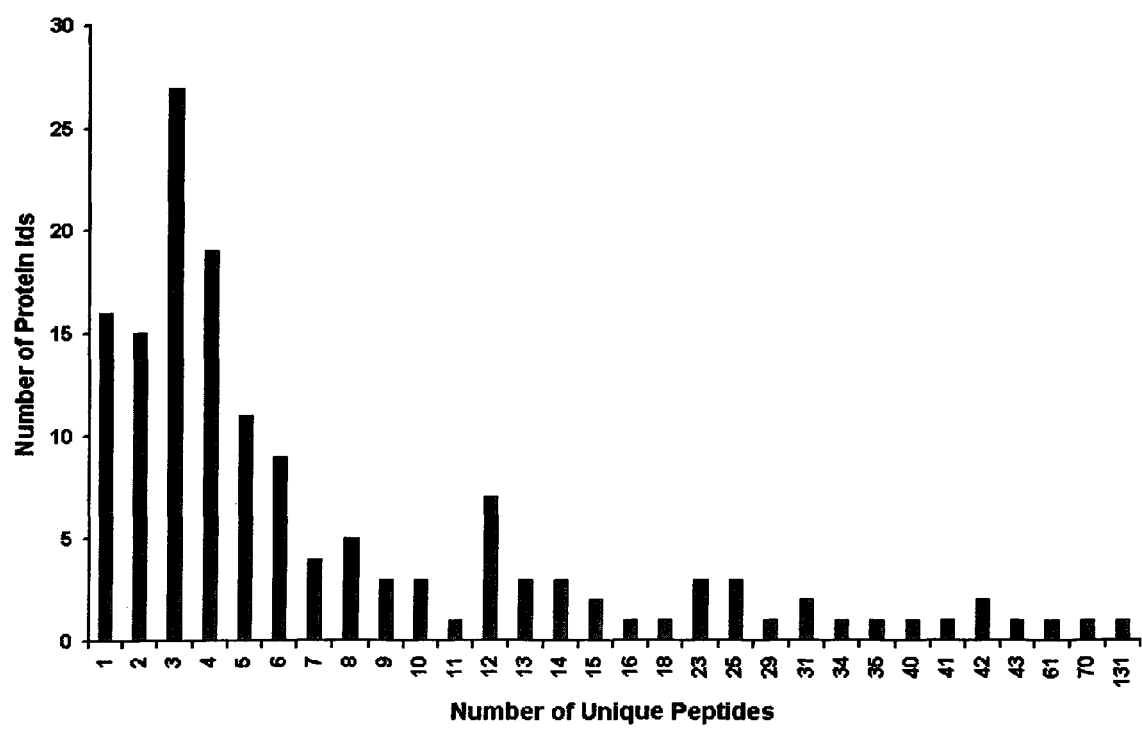
FIG. 21. Tryptic peptide profile of proteins in human CVF. The tryptic peptide profile of the proteins identified in CVF shows that over 89% of the identifications had at least two unique peptide identifications; however, proteins with a wide range of tryptic peptide yields were identified in CVF.
Figure 22:
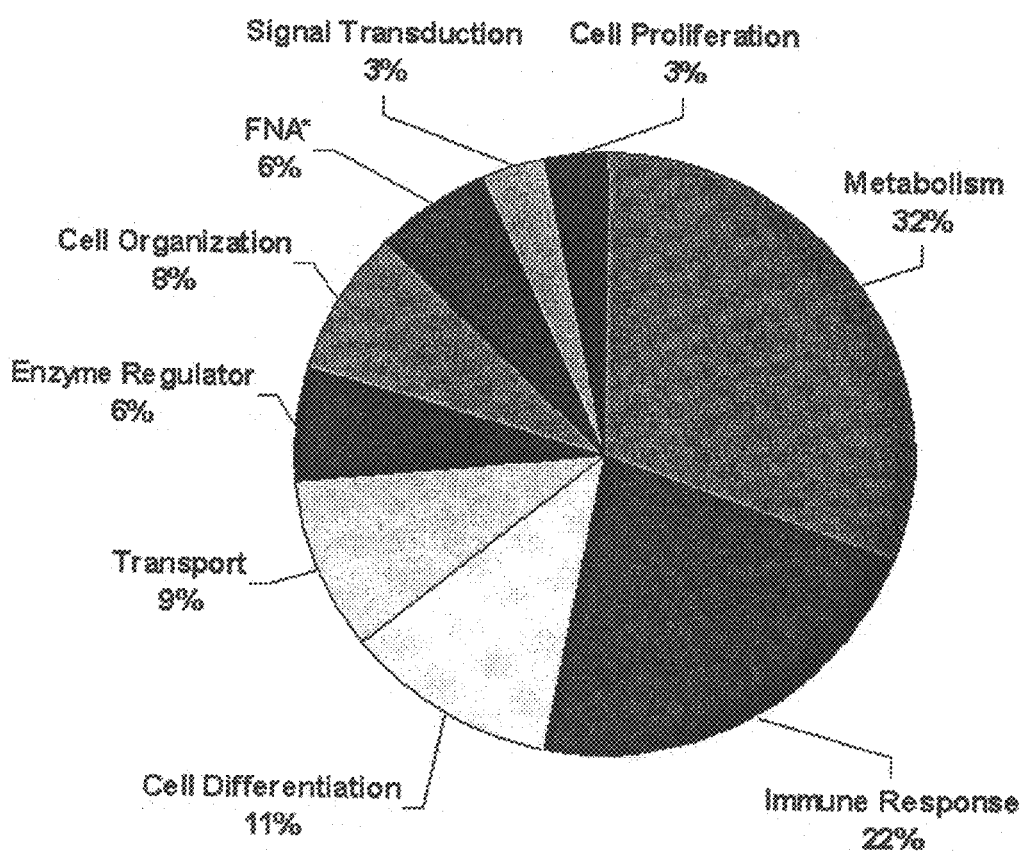
FIG. 22. Functional classification of the human CVF proteome. Functional annotation of human CVF proteins was performed using functional classification tools available on the DAVID bioinformatics resource Dennis, G., Jr. et al., *Genome Biol* 2003, 4, P3. From a total of 150 identified proteins, 32% are involved in metabolism, 22% are involved in immune response, 11% are involved in cell differentiation, 9% are involved in transportation, 8% are involved in cell organization, 6% are involved in enzyme regulation, 3% are involved in signal transduction, and 3% in cell proliferation. No relevant functional annotations* were found in the DAVID database for 6% of the identified proteins.

The combinatorial proteomics approach applied in this study characterized the proteomic composition of CVF during pregnancy by uncovering a large number of proteins that were not previously known to be present in CVF. Table 4 and Table 5 list a comprehensive set of proteins present in CVF that are involved in homeostasis of the reproductive area and fetal protection. The tryptic peptide profile of the proteins listed in Table 4 is shown in FIG. 21. Over 89% of the proteins had at least two unique peptide identifications. The peptide profile also shows that CVF contains a variety of proteins that have a wide range of tryptic peptide yields. FIG. 22 shows the functional classification of the CVF proteome during pregnancy. The major functional groups in CVF are immune and defense-related molecules (such as calgranulins A and B) and metabolic molecules (ranging from proteases like cathepsins B and G to chaperones like HSP 90-α).

The immune-response proteins found in this study fell into three categories: pro-inflammatory response molecules, anti-inflammatory response molecules, and anti-microbial molecules. Apart from commonly occurring immunoglobulins, the most notable pro-inflammatory response molecules found in CVF are two calcium-binding proteins from the S100 family, calgranulins A and B. These proteins form a heterodimer mediated by $Ca^{+2}$ ions and are commonly implicated in both acute-phase and chronic inflammation responses (Kerkhoff, C. et al., *Biochim Biophys Acta* 1998, 1448, (2), 200-11). The relative abundance of these proteins in a control CVF sample, when compared to albumin (Table 4), suggests their vital role in fighting vaginal infections. It is also interesting to note that calgranulins A and B are also found in the intra-amniotic fluid during intra-amniotic infection (Gravett, M. G. et al., *Jama* 2004, 292, (4), 462-9.; Ruetschi, U. et al., *J Proteome Res* 2005, 4, (6), 2236-42), which could lead to preterm labor and birth. Anti-inflammatory response molecules are vital during pregnancy to down-regulate the maternal immune response and prevent immune rejection of the fetus, or to avoid preeclampasia (Lachapelle, M. H. et al., *J Immunol* 1996, 156, (10), 4027-34; Borzychowski, A. M. et al., *Eur J Immunol* 2005, 35, (10), 3054-63). Several of the proteins we detected in CVF, most notably Interleukin 1 Receptor Antagonist (IL1-ra) and Heat Shock Protein 70 kDa (HSP70), belong to the group of molecules which, when expressed during pregnancy, help in down-regulation of the immune response. The secretion of HSP70 into the CVF during pregnancy complicated with vaginal infection induces the expression of IL1-ra (Genc, M. R. et al., *Am J Obstet Gynecol* 2005, 192, (3), 916-21). Presumably, this is a mechanism to preserve a pregnancy on the immunoregulatory level, despite the untoward effects of infection.

Anti-microbial proteins play an important role in preventing infection of the vagina from bacterial and fungal pathogens. Confirming previous reports (MasCasullo, V. et al, *Viral Immunol* 2005, 18, (4), 595-606), we have detected Neutrophil Defensin 1 (Defensin family) and Lactotransferrin in CVF, which are known to have antimicrobial properties and may protect the vagina from infections like *Neisseriae gonorrhoeae* and HSV (MasCasullo et al., supra). Additionally, we have also detected several proteins from the histone family (H4, H2A, H2B, and H1.2). Traditionally, histones are considered to be intracellular proteins that are involved chromatin arrangement inside the nucleus. However, recent studies have indicated that secreted neutrophil extracellular traps (NETs) contain histones (Brinkmann, V. et al., *Science* 2004, 303, (5663), 1532-5; Buchanan, J. T. et al., *Curr Biol* 2006, 16, (4), 396-400), and that secreted histones have a broad range of antimicrobial properties (Venkataraman, N. et al., *J Immunol* 2005, 175, (11), 7560-7; Silphaduang, U. et al., *Biochem Biophys Res Commun* 2006, 340, (2), 648-55; Jacobsen, F. et al., *J Antimicrob Chemother* 2005, 55, (5), 735-41; Kim, H. S. et al., *J Immunol* 2002, 168, (5), 2356-64; Rose, F. R. et al., *Infect Immun* 1998, 66, (7), 3255-63). The detection of a wide range of pro- and anti-inflammatory response molecules, along with various anti-microbial molecules, suggests that the CVF has a complex milieu of innate immune response.

A major proportion (32%) of proteins found in this study are involved in various metabolic activities (FIG. 22) like inflammatory regulation, protein degradation, and protease inhibition. Among the inflammatory regulation proteins we have observed are Heat Shock Protein 90-alpha (HSP90-A), Bradykinin (Kininogen 1 Precursor), and Kallikrein (Kallikrein 11 and 13 precursors). HSP90-A has been recently reported to be involved in cell-mediated activation of the pro-inflammatory bradykinin-kallikrein complex (Joseph, K. et al., *Proc Natl Acad Sci USA* 2002, 99, (2), 896-900). Such cell-mediated immunity has been shown to be a key factor in defense against pathogens that infect lower female genital tract (Pudney, J. et al., *Biol Reprod* 2005, 73, (6), 1253-63). The balance between proteases and protease inhibitors is critical for maintenance of healthy tissue, and imbalances often lead to serious cervical epithelial pathology. Among several proteases and antiproteases we observed in CVF, one of the interesting pairs is cathepsin B and α1 Antitrypsin (A1AT). In cases of cervical carcinoma, the levels of cathepsin B in CVF are elevated, while the levels of A1AT are unchanged (Bhuvarahamurthy, V. et al., *Mol Cell Biochem* 1995, 144, (1), 35-43; Makarewicz, R. et al., *Neoplasma* 1995, 42, (1), 21-4; Benitez-Bribiesca, L. et al., *Arch Invest Med (Mex)* 1980, 11, (4), 523-45). Thus, imbalance between protease and anti-protease expression in the cervix could lead to invasive cervical carcinomas. Detection of the above-mentioned metabolic proteins in CVF suggests that it contains enzymes that regulate a variety of functions ranging from regulation of inflammatory response to maintenance of cervical tissue health.

Apart from immune response and metabolic proteins, we also found proteins that aid in cell differentiation (11%), transport (9%), cell organization (8%), enzyme regulation (6%), signal transduction (3%), and cell proliferation (3%). A protein could have multiple functions depending on its environment. For example, according to the DAVID functional annotation tool, histones are classified as proteins involved in cell organization. However, as discussed earlier, they also have antimicrobial properties when secreted outside the cell. Thus, the role of most of the other proteins found in CVF during pregnancy is still unclear and warrants further investigation.

Prior to this study, the relative abundance of proteins that are native to CVF during pregnancy was largely unknown. The proteins in Table 4 are arranged by their decreasing order of normalized spectral counts. The generic ratio of IgG/IgA protein abundance in our analysis matches well with previous studies (Mestecky, J. et al., *Am J Reprod Immunol* 2005, 53, (5), 208-14). It is interesting to note that the protein abundance profile of CVF and serum differ significantly. Among top 15 abundant CVF proteins, six proteins are known to be either non-native and/or low-abundance in serum (squamous cell carcinoma antigens, calgranulins A and B, small proline rich protein 3, fatty acid-binding protein epidermal, and mucin 5B) (Anderson, N. L. et al., *Mol Cell Proteomics* 2004, 3, (4), 311-26; Wilmarth, P. A. et al., *J Proteome Res* 2004, 3, (5), 1017-23; Qin, S. et al., *Proteomics* 2005, 5, (12), 3183-92; Katz, A. B. et al., *J Invest Dermatol* 1999, 112, (5), 818-21). Furthermore, proteins that are known to be in medium abundance in serum (complement factor C4, complement factor H, and apolipoprotein A-1) were found to be in low abundance in CVF (Anderson et al., supra). Inspection of Table 4 suggests that 40% of the top ten most-abundant proteins in the CVF are inflammatory response molecules. This further supports the assertion that CVF has an effective and aggressive cytokine response system in order to deal with pathogenesis.

A quantitative analysis of proteome overlap between the AF, serum, and CVF was carried out, and the last column in Table 4 and Table 5 denotes the CVF proteins that were also observed in AF (A) and serum (S). Active serum transport and local synthesis are known to be the sources of serum proteins in the cervix (Bard, E. et al., *J Immunoassay Immunochem* 2002, 23, (2), 145-62). Confirming this, we found the sIgA complex, which is locally synthesized in the cervix (Hocini, H. et al., *Scand J Immunol* 1995, 42, (2), 269-74). In addition, we detected several abundant serum proteins (Anderson, N. L. et al., supra; States, D. J et al., supra; Bard, E. et al., supra) like serum albumin, alpha-1-antitrypsin precursor, apolipoprotein A1 precursor, serotransferrin, lactotransferrin, apolipoprotein A1 precursor, Alpha-2-HS glycoprotein, Ig γ 1,2, and 4 chain C regions, and beta-2-glycopotein 1 precursor in CVF. It is interesting to note that we also detected several proteins in CVF, like small proline rich protein 3, CD59 glycoprotein precursor, cystatin A, cystatin B, cornifin A, involucrin, thioredoxin, which are found in AF but not serum. Parallel secretions of the chorionic-decidual membrane could be a source of these proteins in CVF. Among the proteins that were present in all three biological fluids, A1AT and ceruloplasmin (copper transporter) are known to have diagnostic importance. The abundance ceruloplasmin in maternal vaginal secretions and serum has been inversely correlated with incidence of premature rupture of membranes (PROM) (Ogino, M. et al., *J Obstet Gynaecol Res* 2005, 31, (5), 421-6; Kiilholma, P. et al., *Gynecol Obstet Invest* 1984, 17, (4), 194-201), and increased expression of A1AT in serum has been correlated with cervical cancer (Benitez-Bribiesca, L.; et al., *Arch Invest Med (Mex)* 1980, 11, (4), 523-45). This suggests that serial assessment of easily accessible body fluids like CVF or serum could be used in maternal and fetal health diagnostics.

In summary, we have employed a combinatorial proteomics approach using multiple biological replicates, multiple experimental techniques for protein and peptide fractionation, and multiple search engines for data mining was employed in this study to characterize the CVF proteome. This multiplexed approach identified a large set of proteins that were not previously known to be present in CVF. The functional classification of the CVF proteome suggested the presence of a wide variety of cytokine response proteins that play a vital role in fighting pathogens and protecting the fetus. A quantitative analysis of proteome overlap between serum, AF, and CVF identified several serum and AF proteins as present in the CVF during pregnancy. Differential expression of some of those proteins has already been linked to PROM and cervical cancer. However, the exact roles of the majority of new proteins found in CVF during pregnancy are still unclear and will require extensive further investigation. Large-scale high-throughput proteomics technologies are vital to further our understanding of the CVF proteome during pregnancy and its development as a potential diagnostic tool for monitoring maternal and fetal health.

Example 16

Protocols for Global Analysis of the CVF Proteome in a Non-Human Primate Experimental IAI Model Using Multi-dimensional Protein Identification Technology (MudPIT)

Experimental IAI in Non-Human Primates

This protocol was approved by the Institutional Animal Care and Utilization Committee of Oregon Health & Science University. Four pregnant rhesus monkeys (*Macaca mulatta*) with timed gestations were chronically catheterized at 120 days gestation (term is 167 days) as previously described (Gravett, M. G. et al., *Am J Obstet Gynecol* 1994, 171, (6), 1660-7). Experimental IAI was established by intra-amniotic inoculation of $10^7$ colony-forming units of a clinical low-passage *Ureaplamsa parvum*, serovar 1, grown in 10B culture media (Novy M J, et al., Experimental primate model for *Ureaplasma* chorioamnionitis and preterm labor. Society for Gynecologic Investigation, 2001, Toronto, Canada, Mar. 14-17, 2001). Each animal served as its own control. Before and after inoculation, AF and CVF samples were serially collected for quantitative bacterial cultures, white blood cell analysis, and cytokine and prostaglandin concentrations, as previously reported (Gravett et al., supra, Novy et al., supra), and for proteomic analysis. CVF was collected from the posterior vaginal fornix with sterile Dacron swabs (Solon, catalogue #36816), which were then placed into phosphate-buffered saline containing a protease inhibitor cocktail (Roche Diagnositics, catalogue #11836). Following protein extraction, samples were centrifuged to remove cellular debris and the supernatant stored at –70° C. until assayed. For these assays, pooled CVF samples were utilized from samples obtained prior to infection and from 24-72 hours after infection. Uterine contractility was recorded as the area under the amniotic fluid pressure curve and expressed as the hourly contraction area (HCA; mmHg times second/per). Fetal, decidual, placental, and bacterial cultures were obtained after delivery, by Cesarean, from infected animals to confirm infection, and histopathologic studies were performed to confirm histologic chorioamnionitis.

MALDI-TOF-MS Profiling of CVF and AFs

A total of 0.5-3.0 μg of unfractionated protein from CVF and AF was analyzed on a MALDI-TOF-TOF mass spectrometer (AutoFLEX II TOF/TOF, Bruker Daltonics, Billerica, Mass.) equipped with a pulsed-ion extraction source. Briefly, 1 μl of sample was diluted with 4 μl of 50% acetonitrile (ACN)/0.1% trifluoroacetic acid (TFA) and 5 μl of matrix solution (saturated sinapinic acid in 50% ACN/0.5% TFA). Samples were spotted (2 μl) in quadruplicate, onto a 382-well ground steel Scout target (Bruker Daltonics, Billerica, Mass.). The Autoflex was used in linear mode with an accelerating voltage of +20 kV. The pulsed-ion extraction drop voltage was 1500 V with a delay time of 350 ns. Matrix ions were suppressed up to 3000 Da using the maximum ion gating setting. The sampling rate was 2.0 GHz, and each profile spectrum represents a sum of 500 laser shots fired at 10 different positions. A nitrogen laser (λ=337 nm) operating at 50 Hz was used to irradiate samples. The output energy of the laser was ~110 μJ attenuated with an offset of 62% and a range of 36%. Samples were irradiated at a laser power of 30% and standards at 20%. Spectra were manually collected from m/z 3000 to 20000 at a fixed laser power. Spectra were calibrated by external calibration using Protein calibration standard I mixture (Bruker Daltonics, Billerica, Mass.) containing the following: insulin (m/z 5734.6), ubiquitin (m/z 8565.9), cytochrome c (m/z 12361.9), and myoglobin (m/z 16952.6), and analyzed using ClinProt software version 2.0 (Bruker Daltonics, Billerica, Mass.).

One-Dimensional PAGE Coupled to LC-MS/MS Analysis

One hundred μg of CVF protein from control and infected samples was reduced with iodoacetamide and resolved on a Tris-tricine, 10-20% gradient SDS-PAGE gel. The gel was stained with Coomassie blue R-250 and distinct bands from each lane were cut from the gel, destained, and digested in-gel with trypsin for 24 hours at 37° C. using the method of Courchesne and Patterson (Courchesne, P. L. et al., *Methods Mol Biol* 1999, 112, 487-511). Peptides were then extracted with 0.1% TFA and purified using Zip-Tip c18 pipette tips from Millipore. After in-gel digestion, samples were analyzed on a Q-Tof-2 mass spectrometer (Micromass UK Ltd, United kingdom) coupled to a CapLC (Waters, Inc., Milford, Mass.). Masses from 400 to 1500 Da were scanned for the MS survey, and masses of 50 to 1900 Da were scanned for MS/MS. Data analysis for protein identification was done as described below in MudPIT analysis.

MudPIT Protein Identification and Spectral Counting

For CVF MudPIT analysis, 100 µg from each of 4 control and infected samples were pooled to create a 0.4 mg sample from each condition. Protein was dissolved in 100 µl of digestion buffer containing 8 M urea, 1 M Tris base, 80 mM methylamine, and 8 mM $CaCl_2$ (pH 8.5). For reduction and alkylation of cysteine residues, samples were first incubated at 50° C. in 12.5 µl of 0.9 M DTT for 15 min. and then in 25 µl of 1.0 M iodoacetamide in the dark at room temperature for another 15 min. Before adding 40 µl of mass spectrometry-grade trypsin (1 µg/µl; Promega, Madison Wis.), an additional 12.5 µl of 0.9 M DTT along with 210 µl of water and 1 N NaOH to adjust the solution to pH 8.5 was added. Samples were then thoroughly mixed and incubated overnight at 37° C. Digestion was halted by the addition of 40 µl of formic acid. Digests were desalted prior to MudPIT analysis using C18 Sep-Pak cartridges (Waters, Inc., Milford, Mass.).

Desalted digests (1 ml) were injected onto a polysulfoethyl strong cation exchange column (2.1 mm ID×100 mm, 0.5 µm particles and 300-µ pore size (Nest Group, Southborough, Mass.), and fractionated using an HPLC equipped with a UV detector and a fraction collector. Solvent A was 5.6 mM potassium phosphate (pH 3) with 25% acetonitrile (ACN), and Solvent B was 5.6 mM potassium phosphate (pH 3) and 350 mM KCl with 25% ACN. A 95-min. gradient at a flow rate of 200 µl/min was employed for fractionation of peptides: 100% A for 10 min., ramp to 50% B over 45 min., ramp to 100% B over 15 min., and ramp back to 100% A in 0.1 min., hold at 100% A for 20 min. A total of 80 fractions were collected and stored at −20° C. The fractions were evaporated and resuspended in 100 µl of 0.1% TFA for desalting using a 96-well spin column (Vydac C18 silica: Nest Group, Southborough, Mass.). After elution in 80% ACN/0.1% formic acid (FA), fractions were consolidated into 43 fractions, evaporated, and resuspended in 25 µl of 5% FA.

SCX fractions (5 µl each) were analyzed on a Q-Tof-2 mass spectrometer connected to a CapLC (Waters Inc., Milford, Mass.). The Q-Tof-2 was equipped with a nanospray source. Each SCX fraction was separated using a Nanoease C18 75 µm ID×15 cm fused silica capillary column (Waters Inc., Milford, Mass.) and a 95-min water/ACN gradient. The mass spectrometer was calibrated using Glu1Fibrinopeptide B. An MS/MSMS survey method was used to acquire spectra. Masses from m/z 400 to 1500 were scanned for MS survey and masses from m/z 50 to 1900 for MSMS. MS/MS spectra were processed with ProteinLynx Global Server v.2.1 software (Waters Inc., Milford, Mass.).

A total of 3,120 MS/MS spectra from control samples and 2,800, MS/MS spectra from IAI samples were searched against a combined database containing known contaminants and forward and reverse entries of the Swiss-Prot™ human database (version 46.6) using three independent search engines: OpenSea, TurboSequest (ThermoFinnigan, Waltham, Mass.), and X! Tandem. PEAKS software (Bioinformatics Solutions, Ontario, Calif.) was used to generate de novo sequences for the OpenSea search engine. Protein identifications from individual search engine results were combined using probabilistic protein identification algorithms implemented in Scaffold software (Proteome Software, Portland, Oreg.). 52% of the spectra from the control sample and 50% of the spectra from the IAI sample were assigned to proteins with at least one confident peptide (probability.g-toreq.0.8) identification. Protein identifications having at least two independent peptide identifications (probability ≧0.8) were considered likely to be present in the sample.

Polyclonal Antibodies and Western Immunoblotting

Immunogenic peptides and/or recombinant proteins were used to generate rabbit and goat polyclonal antibodies (DSL Laboratories, Webster, Tex.). Affinity-purified antibodies were then used for western blots. One hundred µg of CVF protein was resolved on 4-20% SDS-PAGE and transferred to PVDF membranes. The membranes were blocked with 5% fat-free milk in PBST for 45 min at room temperature and incubated with 1 µg/ml primary antibody (IGFBP-1, Azurocidin, Calgranulin-A, Calgranulin-B, Anexin II, Lipocalin, Profilin) overnight at 4° C. After three washes with TBST, the membrane was incubated with IgG-HRP secondary antibody (Sigma-Aldrich Co.) and visualized with enhanced chemiluminescence (Pierce).

Statistical Analysis

Spectral counting was used to determine the proteins that were differentially expressed between control and infected MudPIT samples. All proteins with more than two confident peptide identifications were considered for protein quantification using spectral counting. Identified protein lists were further curated by collapsing spectral counts for similar proteins (e.g., immunoglobulins, α-1-acid-glycoproteins 1 and 2, and pregnancy-specific glycoproteins) into a single entry. Spectral counts of identical peptides between dissimilar proteins were split between the proteins in equal ratios. Curated protein lists for both samples were merged and an independent 2×2 $\chi^2$ test on the spectral counts for each protein between the samples was used to find proteins that were differentially present between them. In order to reduce the false-positive rate of differentially abundant proteins, only proteins with a p-value<0.1 and with at least two independent peptides matched to at least four MS/MS spectra (probability >0.8) in at least one of the samples were considered as statistically significant. Fold changes of proteins passing the above criteria were determined using a published formula for calculating spectral count ratios (Old, W. M. et al., *Mol Cell Proteomics* 2005, 4, (10), 1487-502.)

Example 17

Global Analysis of the CVF Proteome in a Non-Human Primate Experimental IAI Model Using Multidimensional Protein Identification Technology (MudPIT)

Using the protocols described in Example 16, the following results were obtained.

Results

Experimental IAI Following *Ureaplasma parvum* Infection

Following intra-amniotic inoculation, infection was rapidly established in all animals. Increases in uterine contractility from basal levels of 100 HCA to levels in excess of 3,000-6,000 HCA occurred an average of 54 (range 34-72) hours after inoculation with *Ureaplasma parvum*, and led to progressive cervical changes, as measured by the Bishop score. Increases in uterine contractility were preceded by significant elevations in the pro-inflammatory cytokines TNF-α, IL-1β, IL-6, and IL-8, and prostaglandins $E_2$ and $F_{2\alpha}$ as previously reported (Gravett, M. G., et al., *Am J Obstet Gynecol* 1994, 171, (6), 1660-7; Novy M J, et al.: Experimental primate model for *Ureaplasma* chorioamnionitis and preterm labor. Society for Gynecologic Investigation. 2001, Toronto, Canada, Mar. 14-17, 2001). No animal had other clinical signs of IAI at the time of initial increases in uterine contractility. Following delivery, histopathologic examination confirmed chorioamnionitis in all cases.

Global Analysis of the CVF Proteome in a Non-Human Primate Experimental IAI Model Using Multidimensional Protein Identification Technology (MudPIT)

Increasing confidence in mass spectrometry-based peptide identification and quantification methods has launched the development of extensive and varied multi-dimensional peptide separations coupled with MS/MS. Such "shotgun" peptide sequencing endeavors produce reliable protein identifications, as well as relative quantitative information for comparing sets of samples analyzed in parallel.

Figure 23A:
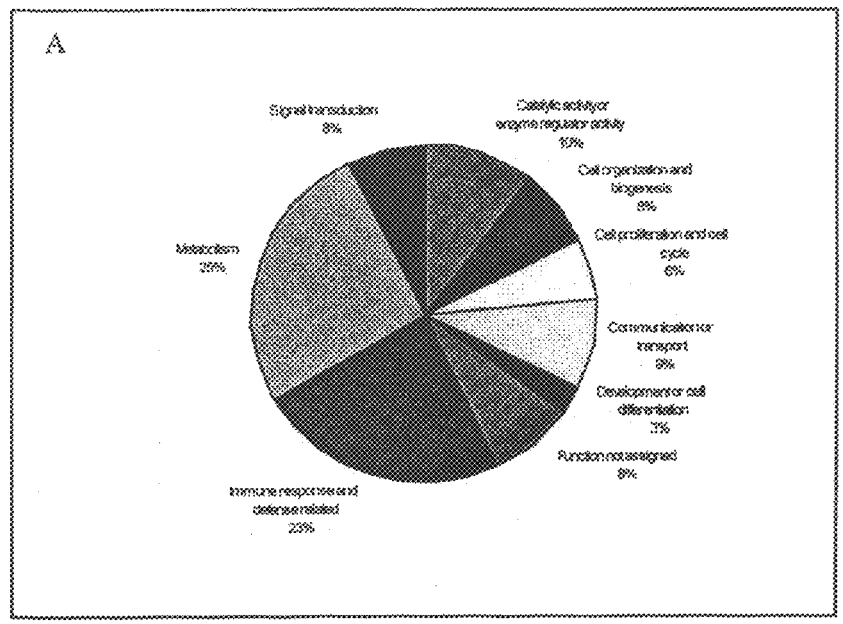
FIGS. 23 A-B. Functional annotation and cellular localization of proteins expressed in CVF. Two hundred and five proteins identified utilizing MudPIT and gel-based fractionation were analyzed for GeneOntology terms (GO terms) using an annotation database (DAVID, Version 2.0, NIAID). 8% of the total proteins did not show any known functional annotation.
Figure 23B:
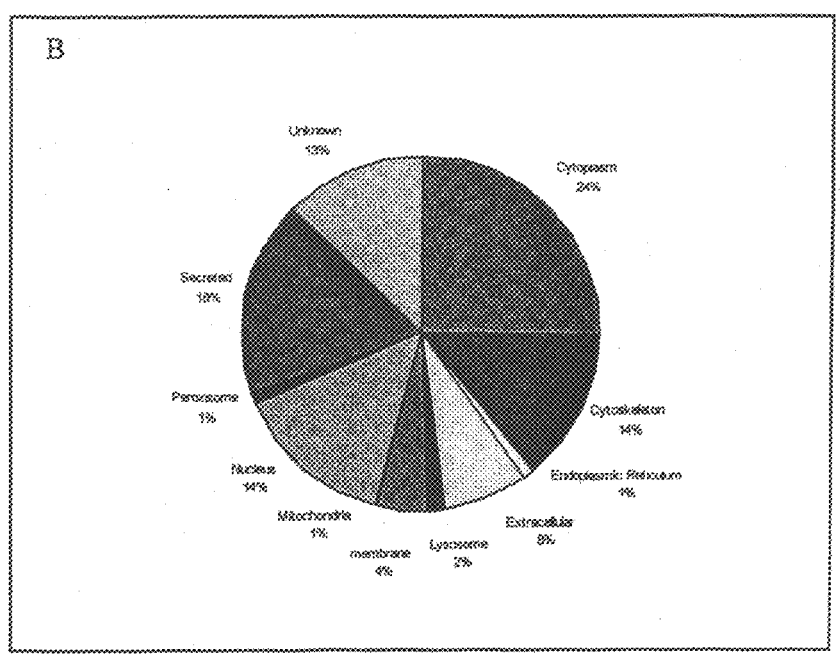

A total of 205 unique proteins (Table 6) were identified in CVF using MudPIT and gel-based fractionation (1D PAGE coupled to LC-Tandem mass spectrometry) analyses. Functional annotation of the CVF proteome using GeneOntology terms (DAVID V 2.1) showed (FIG. 23A) a majority of them to be associated with metabolism (25%) and immune response (23%). Analysis of the predicted sub-cellular location of the proteins identified from CVF (FIG. 23B) showed that the annotated proteins are from cytoplasmic (24%), secretory (18%), cytoskeletal (14%), and nuclear (14%) categories. No information was available regarding the cellular location of 13% of the proteins identified.

For the analysis of differential protein levels in the setting of infection, CVF samples obtained before and after experimental IAI were digested with trypsin and subjected to MudPIT analysis. MS/MS spectra derived from the MudPIT analysis led to the high-confidence identification (2 or more peptides/protein) of 149 and 151 proteins in the control and infected samples, respectively. To decrease false-positive protein identification rates, MS/MS spectra were searched against a database containing known contaminants (i.e., trypsin, keratin, and serum albumin) and both forward and reverse peptide sequence entries from the Swiss-Prot™ human and primate databases using three independent search engines. A probability-based algorithm, Scaffold (Proteome Software Inc., Portland, Oreg.), was used to combine results from the three search engines. The use of multiple searching algorithms increases the confidence in reported identifications by decreasing peptide identifications occurring by chance. Protein identification numbers reported above had two or more unique peptide identifications.

For quantitative comparison of control and IAI samples, a spectral counting method was implemented. Spectral counting permits rapid detection of abundance differences between two sample pools without resorting to complicated differential labeling experimentation (Zybailov 2005). Curated protein lists from control and IAI were compiled, and independent $\chi^2$ tests on the spectral counts of each protein were performed. Proteins with calculated $\chi^2$ values over 2.706 (90% confidence interval) are reported in Table 7.

Included in the table are the spectral counts and the number of MS/MS peptide spectra matching to the given protein, for the control and IAI samples. The fold change between control and IAI for each of the significant proteins was also calculated. Of the 27 proteins found to be differentially present between control and IAI by spectral counting, 19 proteins had $\chi^2$ values in the 99% confidence interval, and 8 proteins had $\chi^2$ values in the 95% confidence interval. When compared to quantitative proteomic studies performed using protein separations (1D PAGE LC-MS/MS), 15 proteins found by spectral counting corresponded to differential trends seen in 1-D gel-based experiments. The identification of potential lower-abundance serum protein markers is one of the benefits of MudPIT analysis. The multi-dimensional front-end peptide separations (SCX and RP-LC) permit the interrogation of a wider dynamic range of concentration over gel-based proteomic analyses as well as MALDI profiling technologies.

Figure 24:
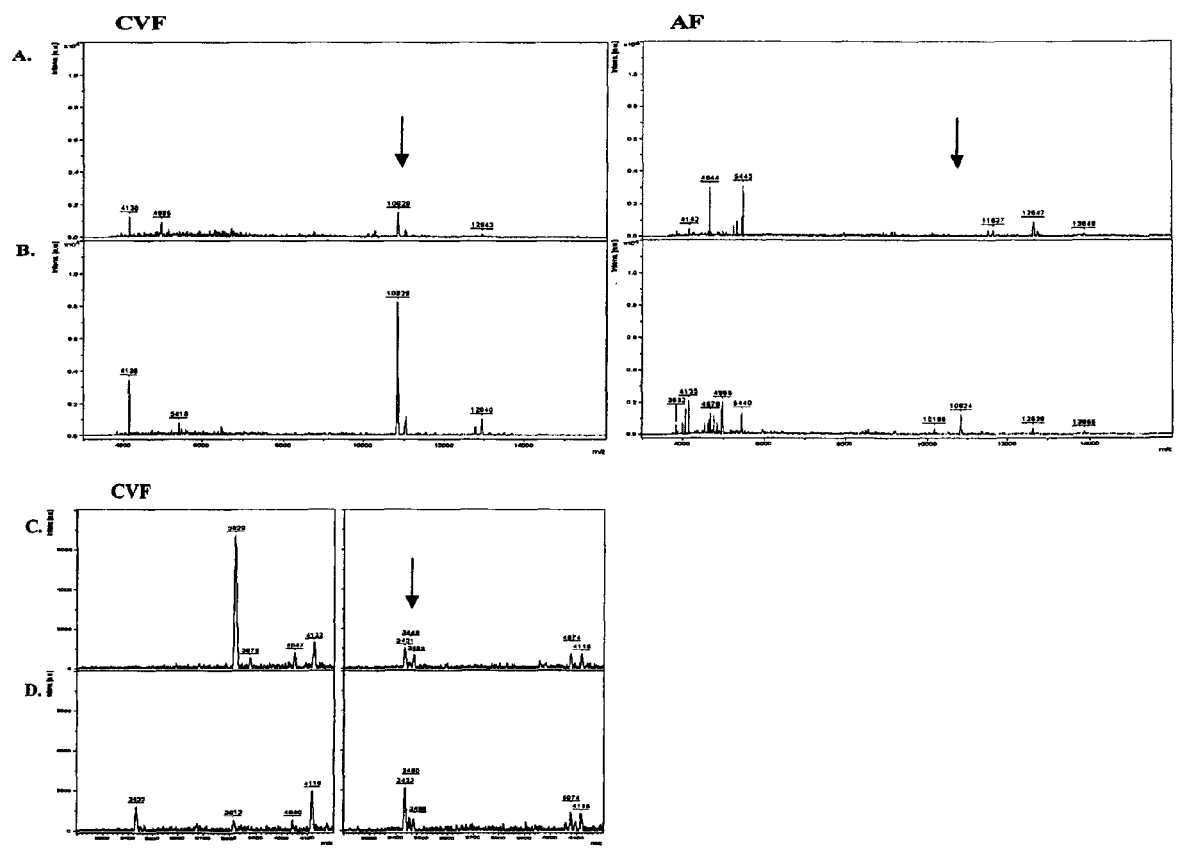
FIGS. 24 A-D. Matrix-assisted laser desorption/ionization time-of-flight (MALDI-TOF-MS) protein profiles of *Ureaplasma parvum*-induced differential protein levels in non-human primate CVF and AF samples. Profiles demonstrating the 10.8-kDa peak are shown in control samples prior to (A) and following (B) experimental IAI. Profiles demonstrating peptides in the 3-5-kDa MW range are shown in C) control samples taken prior to and D) samples taken following experimental IAI. Spectra were processed for baseline subtraction and Savitsky-Golay smoothing, 5 cycles at 10 Da/channel. Spectra representing m/z range from 3000 to 2000 are shown with arrows indicating differentially expressed peaks between control and infection.

The potential biomarkers for detection of IAI in CVF, summarized in Table 7, were predominantly immunoregulatory proteins. Several of these, including calgranulins A and B, azurocidin, and IGFBP-1, which were differentially present in IAI AF, were also found to be up-regulated in IAI CVF. The differential abundance of total IGFBP-1 (Table 7) reflected both the intact 30-kDa protein and a proteolytic fragment, identified by Western blot in FIGS. 24A-D. However, the majority of IGFBP-1 present in the setting of IAI was comprised of the proteolytic fragment (FIG. 24). Defensins, previously identified as markers for intra-amniotic or lower genital tract infection, were also identified in the 3-5-kDa peak. However, their differential presence in control and IAI CVF did not achieve statistical significance by spectral analysis. Of interest, the basal levels of some of the immunoregulatory peptides were higher in CVF compared to AF, consistent with a more chronically inflammatory milieu in the microbial rich lower genital tract than in the normally sterile amniotic cavity.

Identification of IAI Protein Profiles by MALDI-TOF MS

MALDI-TOF MS analyses of CVF and AF protein extracts revealed several peak intensity differences in 3-5-kDa and 11-12-kDa regions between infected and non-infected primate and human CVF and AF (FIGS. 24A-D), similar to the previously reported protein signature profile in AF obtained by SELDI-TOF (Gravett, M. G. et al., *Jama* 2004, 292, (4), 462-9).

A 10.8-kDa cluster was consistently up-regulated in infected CVF and amniotic fluid in all cases. Of interest, the relative intensity of this peak was greater among CVF samples than among AF samples following infection, consistent with the hypothesis that the basal state of the lower genital tract milieu is pro-inflammatory. The increased expression of the 3-5-kDa cluster in response to IAI is more robust in AF compared to CVF. The proteins with masses 3432 and 4128 Da were commonly over-expressed in AF and CVF in the presence of IAI. These masses may represent defensins, as reported earlier (Buhimschi, I. A.; et al., *Bjog* 2005, 112, (2), 173-81). Longitudinal sampling following *Ureaplasma parvum* infection revealed that the 10.8-kDa cluster intensity was increased as early as 24 hours after inoculation, and preceded increases in HCA in infected animals in both CVF and AF samples (data not shown).

Immunodetection of IAI Biomarkers

Figure 25:
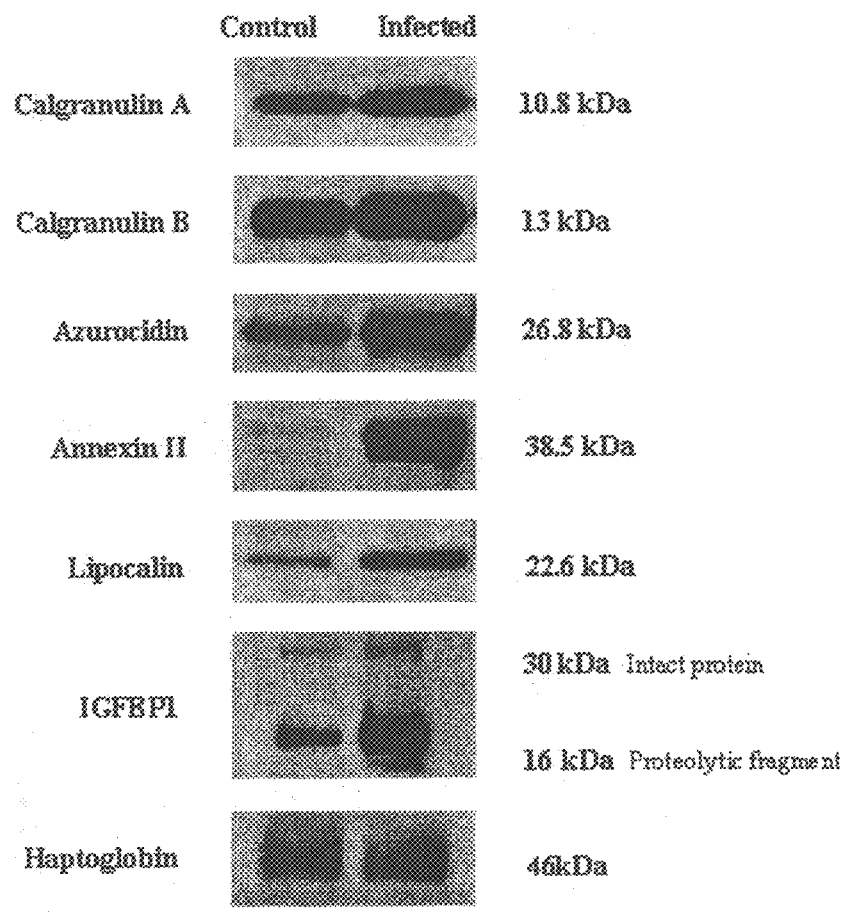
FIG. 25. Immunodetection of CVF biomarkers for IAI. Haptoglobin, unregulated control marker. IGFBP-1 bands represent the intact protein (~30 kDa) and proteolytic fragment (~19 kDa).

To validate the differential expression of proteins identified in IAI, we selected 5 of the markers identified from MudPIT analysis. Antibodies were raised for Calgranulins A and B, IGFBP-1, Azurocidin, Lipocalin, Annexin II, and an unregulated protein (Haptoglobin) to confirm the differential abundance of potential IAI biomarkers. As shown in FIG. 25, western blot analysis confirmed the differential presence of all of these biomarkers, which exhibited differential levels that were consistent with the protein identification experiments performed on IAI CVF.

Discussion

Subclinical IAI is present in at least 50% of extremely premature births, in which neonatal morbidity and mortality are disproportionately high (Goldenberg, R. L. et al., *N Engl J Med* 2000, 342, (20), 1500-7). The early clinical diagnosis of IAI is made difficult by the fact that signs and symptoms of IAI are a late manifestation of the infection. Furthermore, the available non-invasive diagnostic tests (e.g., maternal white blood cell count or C-reactive protein) have limited predictive value. Other tests, including measurement of AF glucose, leukocytes, interleukin-6, or Gram stain require amniocentesis, and additionally, in the case of AF culture, the results are delayed beyond a clinically optimal timeframe.

A causal relationship between IAI and preterm delivery that parallels the course observed in women has been demonstrated in a non-human primate experimental model (Gravett, M. G. et al., *Am J Obstet Gynecol* 1994, 171, (6), 1660-7). In a study described in the previous examples, we utilized SELDI-TOF mass spectrometry to characterize protein profiles in AF from rhesus monkeys with experimental IAI and in women with subclinical IAI and preterm delivery (see also Gravett, M. G. et al., *Jama* 2004, 292, (4), 462-9). We identified a unique SELDI-TOF profile with elevated levels of peptides in the 3-5-kDa and in the 10.8-kDa molecular weight ranges in all AF samples after infection, and in no AF obtained prior to infection. Similarly, this unique protein profile was observed in all women with IAI and preterm delivery, and in no women with preterm labor without infection and subsequent delivery at term. Proteins identified by tandem mass spectrometry within these mass ranges included calgranulins A and B and a unique proteolytic fragment of IGFBP-1. These findings have recently been confirmed, and other protein biomarkers of IAI identified, by Buhimschi, et al. *Bjog* 2005, 112, (2), 173-81.

In the present study, we sought first to characterize the proteome of CVF and to characterize and to compare with AF, the protein profile in CVF from rhesus monkeys with experimental IAI utilizing the same experimental model as previously described (Gravett, M. G. et al., *Am J Obstet Gynecol* 1994, 171, (6), 1660-7; Novy M J, et al.: Experimental primate model for *Ureaplasma* chorioamnionitis and preterm labor. Society for Gynecologic Investigation. 2001, Toronto, Canada, Mar. 14-17, 2001; Gravett, M. G. et al., *Jama* 2004, 292, (4), 462-9). This is the first report utilizing MALDI-TOF mass spectrometry and multidimensional protein identification technology (MudPIT) to characterize the protein profile of CVF and to identify novel biomarkers for IAI in a site that allows for non-invasive collection of serial samples from a more accessible maternal sampling site. This may allow for the risk prediction or diagnosis of ascending intrauterine infection in the etiology of IAI and, by comparison with maternal serum and fetal AF sampling, provide new insights into the pathogenesis of IAI. We utilized a well-established, non-human primate model in which experimental IAI was caused by intra-amniotic inoculation of *Ureaplasma parvum*. We chose this pathogen because the most frequently isolated microorganisms from placentae of women with histologic chorioamnionitis (Hillier, S. L. et al., *N Engl J Med* 1988, 319, (15), 972-8) or from AF of women in preterm labor with intact fetal membranes are *Ureaplasma* species (*U. urealyticum* and *U. parvum*). *Ureaplasma* species have also been implicated in postpartum endomyometritis, neonatal sepsis, meningitis, and neonatal bronchopulmonary dysplasia (Chaim, W. et al., *Eur J Obstet Gynecol Reprod Biol* 2003, 109, (2), 145-8; Viscardi, R. M. et al., *Pediatr Dev Pathol* 2002, 5, (2), 141-50; Yoon, B. H. et al., *Am J Obstet Gynecol* 2000, 183, (5), 1130-7).

We utilized two very distinct proteomic approaches in this study: a rapid protein fingerprinting approach (MALDI-TOF MS) that generates distinct expression profiles and is amenable for developing rapid screening assays, together with a in-depth protein identification and quantification approach (LC-LC-MS/MS, MudPIT) that provides the identity of the biomarkers suitable for identification by conventional immunoassays. MALDI-TOF-MS-based profiling techniques have been targeted for their robustness, ease-of-use, and high-throughput nature. The majority of profiling studies to date have evaluated disease states using MALDI-MS protein profiling methods involving serum fractionation using chromatographic techniques coupled with MALDI-TOF-MS. While the MS protein profiles from these studies may have identified unique masses capable of discriminating between normal and perturbed samples, the methodologies used are unable to identify and validate found protein classifiers based solely upon the MALDI-MS protein m/z value.

Two-dimensional gel electrophoresis (2-DE) commonly used to detect differential protein expression patterns (Tsangaris, G.; et al., *Electrophoresis* 2005, 26, (6), 1168-73; Pieper, R. et al., *Proteomics* 2003, 3, (7), 1345-64) is biased towards detection of high-abundance proteins, with limited capabilities to detect low-abundance proteins (Gorg, A., et al., *Proteomics* 2004, 4, (12), 3665-85). Advances in multidimensional LC approaches coupled to MS/MS (Multi-dimensional Protein Identification Technology, MudPIT) have enabled better sample enrichment, separation, and in-depth peptide coverage to study global protein expression changes from tryptic digests of complex mixtures (Washburn, M. P. et al., *Nat Biotechnol* 2001, 19, (3), 242-7.; Schirmer, E. C. et al., *Science* 2003, 301, (5638), 1380-2.; Le Roch, K. G. et al., *Genome Res* 2004, 14, (11), 2308-18; Peng, J. et al., *Nat Biotechnol* 2003, 21, (8), 921-6; Ideker, T. et al., *Science* 2001, 292, (5518), 929-34). Recently, MS/MS spectral sampling from complex peptide mixtures has been identified as a source of relative quantitative information. Using spectral counting, the total number of peptide identifications in a complex peptide mixture analyzed by MudPIT was found to correlate linearly with protein abundance over a 100-fold concentration range and to be more reproducible with a wider dynamic range over mass spectrometry-derived ion chromatograms (Old, W. M. et al., *Mol Cell Proteomics* 2005, 4, (10), 1487-502; Liu, H. et al., *Anal Chem* 2004, 76, (14), 4193-201; Zybailov, B. et al., *Anal Chem* 2005, 77, (19), 6218-24).

Characterization of proteins expressed in CVF in control and IAI using MudPIT analyses revealed a significant number of immune response/defense-related proteins that were up-regulated in IAI. There is a considerable degree of overlap between the differentially abundant proteins in AF and CVF during IAI. In our study, calgranulins, azurocidin, lipocalin, L-plastin, and others, which were previously identified as potential biomarkers for IAI in amniotic fluid, were also differentially present in CVF. In addition to the above immunomodulators, the detection of the antibacterial protein azurocidin in CVF in response to infection provides new insights into the intrauterine immune response. Azurocidin (CAP37) is a cationic antimicrobial protein isolated from human neutrophils that has potentially important actions in host defense and inflammation (Gabay, J. E. et al., *Proc Natl Acad Sci USA* 1989, 86, (14), 5610-4). Another antimicrobial protein with elevated expression in IAI is cathelin, which has a C-terminal 37-residue alpha-helical peptide active against bacterial infection (Zhao, C. et al., *Antimicrob Agents Chemother* 2001, 45, (10), 2695-702). The increased levels of annexins in infected CVF may relate to CVF-specific IAI responses. Annexins are a group of $Ca^{2+}$-binding proteins that are associated with inflammatory and defense responses. Annexin A2 is up-regulated in viral-transformed cell lines and in human tumors (Filipenko, N. R. et al., *J Biol Chem* 2004, 279, (10), 8723-31). Annexin 1 modulates the anti-inflammatory actions of the steroid hormones (Castro-Caldas, M. et al., *Mediators Inflamm* 2001, 10, (5), 245-51). Matrix metalloproteinases (MMPs) are a family of zinc-dependent endopeptidases that are expressed in many inflammatory conditions and contribute to connective tissue breakdown. It has been proposed that bacterial products and/or the proinflammatory cytokines IL-1beta and TNF-alpha, as paracrine or autocrine signals, may trigger amniochorion cells to induce MMP expression (Vadillo-Ortega, F. et al., *Am J Obstet Gynecol* 2002, 186, (1), 128-38; Vadillo-Ortega, F. et al., *Bjog* 2005, 112 Suppl 1, 19-22.

In the second approach, we utilized MALDI-TOF MS and detected a significantly over-expressed 10.8-kDa cluster in CVF in the setting of experimental primate IAI. This is similar to the AF proteome profile observed in our previous studies (Gravett, M. G. et al., *Jama* 2004, 292, (4), 462-9), and confirms the specificity of this signature profile for the detection of IAI in CVF. This over-expressed cluster could represent the basic intrauterine immune response to infection, as one set of proteins identified in this unique cluster, i.e., the calgranulins, are members of the S-100 calcium binding protein family that is expressed by macrophages and by epithelial cells in acutely inflamed tissues. The second candidate from this cluster, a proteolytic fragment of IGFBP-1, indicates a potential protease-related mechanism in response to infection. Intact IGFBP-1 is the major IGFBP found in AF, and is synthesized by both fetal membranes and maternal decidua. Notably, however, this signature is present, albeit in lower relative concentrations, in CVF samples, but absent in AF samples prior to infection. The higher basal levels of these immunoregulatory peptides may reflect the basal inflammatory characteristics of the vaginal milieu compared to that of amniotic fluid. Amniotic fluid is normally sterile, with minimal concentrations of inflammatory markers. In contrast, the vagina is characterized by a pro-inflammatory, microbe-rich environment. Thus, while CVF samples may have the advantage of ease of non-invasive sampling, the results may be confounded by local inflammatory conditions such as bacterial vaginosis.

Characterization of the CVF proteome and identification of a significant number of proteins differentially expressed in IAI complements the sensitive proteomic approaches used to identify biomarkers and their potential value in development of non-invasive testing for IAI. Much can be learned about the pathogenesis of IAI by analysis of temporal and quantitative samples from CVF, AF, and maternal serum. Analogous issues have been raised by surveys of other cervical-vaginal inflammatory biomarkers such as pro-inflammatory cytokines and fetal fibronectin (Rizzo, G. et al., *Am J Obstet Gynecol* 1996, 175, (4 Pt 1), 812-7; Holst, R. M. et al., *Acta Obstet Gynecol Scand* 2005, 84, (6), 551-7; Di Naro, E. et al., *Acta Obstet Gynecol Scand* 2003, 82, (12), 1072-9; Yoon, B. H. et al., *Am J Obstet Gynecol* 2001, 185, (5), 1137-42). These observations, and ours, are consistent with the hypothesis that, during infection-associated preterm birth, there is a disruption of the extracellular matrix at the choriodecidual interface, and that inflammatory mediators produced at this interface reach the vaginal pool, possibly in association with a breakdown in cervical barriers.

In summary, we utilized two complimentary proteomic approaches to characterize the global expression of cervical-vaginal proteins and to identify potential biomarkers of IAI in cervical vaginal fluid. Distinct immunoregulatory peptides were identified that were differentially expressed in CVF following experimental IAI. The differential expression of these peptides was confirmed with immunoassay, and provides an opportunity for the development of non-invasive reliable tests for the diagnosis of IAI.

Example 18

Global Analysis of the Human CVF Proteome in IAI Using Multidimensional Protein Identification Technology (Mud-PIT)

Using the protocols described in Example 14, the following results were obtained.

Results

From the human study, a subset of patients was retrospectively identified for proteomic analysis as reported here. This subset included 20 patients with evidence of intrauterine infection (as defined by the recovery of a microbial pathogen form amniotic fluid or an amniotic fluid IL-6 concentration of >2,000 pg/ml), and a randomly selected subset of 20 patients without intrauterine infection but with preterm birth and 20 patients without infection and with preterm labor responsive to tocolytic therapy and who had subsequent term birth. These patients constitute the study population for this study.

Human CVF samples were collected by placing 2 sterile 6-inch Dacron-tipped plastic applicators (Solon, Skowhegan, Me.) into the posterior vaginal fornix and rotating them for 15 seconds during a sterile speculum examination. Following collection, protein was extracted into phosphate-buffered saline containing a protease inhibitor cocktail (Roche Diagnostics, Alameda, Calif.). Samples were spun down after extraction to remove any debris and cellular material, and the supernatant was stored at $-70°$ C.

One-Dimensional PAGE Coupled to LC-MS/MS Analysis

One hundred mg of CVF protein pooled from each group of samples was reduced with iodoacetamide and resolved on a Tris-tricine, 10-20% gradient SDS-PAGE gel. The gel was stained with Coomassie blue R-250 and distinct bands from each lane were cut from the gel, destained, and digested in-gel with trypsin for 24 hours at $37°$ C. Peptides were then extracted with 0.1% TFA and purified using Zip-Tip c18 pipette tips from Millipore. After in-gel digestion, samples were analyzed on a Q-Tof-2 mass spectrometer (Micromass UK Ltd, United kingdom) coupled to a CapLC (Waters, Inc., Milford, Mass.). Masses from 400 to 1500 Da were scanned for the MS survey, and masses of 50 to 1900 Da were scanned for MS/MS. Data analysis for protein identification was done as described below in MudPIT analysis.

MudPIT Protein Identification and Spectral Counting

For CVF MudPIT analysis, 50 ul from each sample (n=20 in each group) were pooled to create a 0.6 mg sample from each condition. Protein was dissolved in 100 ml of digestion buffer containing 8 M urea, 1 M Tris base, 80 mM methylamine, and 8 mM CaCl2 (pH 8.5). For reduction and alkylation of cysteine residues, samples were first incubated at $50°$ C. in 12.5 ml of 0.9 M DTT for 15 min. and then in 25 ml of 1.0 M iodoacetamide in the dark at room temperature for another 15 min. Before adding 40 ml of mass spectrometry-grade trypsin (1 mg/ml; Promega, Madison Wis.), an additional 12.5 ml of 0.9 M DTT along with 210 ml of water and 1 N NaOH to adjust the solution to pH 8.5 was added. Samples were then thoroughly mixed and incubated overnight at $37°$ C. Digestion was halted by the addition of 40 ml of formic acid. Digests were desalted prior to MudPIT analysis using C18 Sep-Pak cartridges (Waters, Inc., Milford, Mass.).

Desalted digests (1 ml) were injected onto a polysulfoethyl strong cation exchange column (2.1 mm ID×100 mm, 5 mm particles and 300-m pore size (Nest Group, Southborough, Mass.), and fractionated using an HPLC equipped with a UV detector and a fraction collector. Solvent A was 5.6 mM potassium phosphate (pH 3) with 25% acetonitrile (ACN), and Solvent B was 5.6 mM potassium phosphate (pH 3) and 350 mM KCl with 25% ACN. A 95-min. gradient at a flow rate of 200 ml/min was employed for fractionation of peptides: 100% A for 10 min., ramp to 50% B over 45 min., ramp to 100% B over 15 min., and ramp back to 100% A in 0.1 min., hold at 100% A for 20 min. A total of 80 fractions were collected and stored at −20° C. The fractions were evaporated and resuspended in 100 ml of 0.1% TFA for desalting using a 96-well spin column (Vydac C18 silica: Nest Group, Southborough, Mass.). After elution in 80% ACN/0.1% formic acid (FA), fractions were consolidated into 43 fractions, evaporated, and resuspended in 25 ml of 5% FA.

SCX fractions (5 ul each) were analyzed on a Q-Tof-2 mass spectrometer connected to a CapLC (Waters Inc., Milford, Mass.). The Q-Tof-2 was equipped with a nanospray source. Each SCX fraction was separated using a Nanoease C18 75 mm ID×15 cm fused silica capillary column (Waters Inc., Milford, Mass.) and a 95-min water/ACN gradient. The mass spectrometer was calibrated using Glu1Fibrinopeptide B. An MS/MSMS survey method was used to acquire spectra. Masses from m/z 400 to 1500 were scanned for MS survey and masses from m/z 50 to 1900 for MSMS. MS/MS spectra were processed with ProteinLynx Global Server v.2.1 software (Waters Inc., Milford, Mass.).

An average of 2,800 MS/MS spectra from each group were searched against a combined database containing known contaminants and forward and reverse entries of the Swiss-Prot™ human database (version 46.6) using three independent search engines: OpenSea 14, 15, TurboSequest (ThermoFinnigan, Waltham, Mass.), and X! Tandem 16. PEAKS software (Bioinformatics Solutions, Ontario, Calif.) was used to generate de novo sequences for the OpenSea search engine. Protein identifications from individual search engine results were combined using probabilistic protein identification algorithms implemented in Scaffold software (Proteome Software, Portland, Oreg.). Protein identifications having at least two independent peptide identifications (probability >0.8) were considered likely to be present in the sample.

Results

PTL versus IAI—A comparison of PTL versus IAI showed 33 proteins with statistically significant (p<0.05) differential abundance (Table 10). The differential presence of these proteins ranged from +45-fold to −8.7-fold. Twenty one proteins including Squamous cell carcinoma antigen 1 (SCCA-1), Annexin A2 (Annexin II), S100 calcium-binding protein A7 (Psoriasin), Periplakin, Heat shock cognate 71 kDa protein, Involucrin, Fatty acid-binding protein, epidermal (E-FABP), Thioredoxin (ATL-derived factor) (ADF), Histone H4, Neuroblast differentiation associated protein AHNAK, Annexin A1 (Annexin I) (Lipocortin I), Actin, cytoplasmic 1 (Beta-actin), Heat-shock protein beta-1 (HspB1), Fructose-bisphosphate aldolase A (EC 4.1.2.13), Mucin-5B precursor, Small proline-rich protein 2A (SPR-2A) (2-1), Cystatin A (Stefin A) (Cystatin AS), Myeloperoxidase precursor (EC 1.11.1.7) (MPO), Cornifin A (Small proline-rich protein IA) (SPR-IA), Neutrophil gelatinase-associated lipocalin precursor were more abundant in PTL compared to IAI. Twelve proteins including Hemopexin precursor (Beta-1B-glycoprotein), Serotransferrin precursor (Transferrin) Catalase (EC 1.11.1.6), Lysozyme C precursor (EC 3.2.1.17), Matrix metalloproteinase-9 precursor (MMP-9) kDa matrix metalloproteinase-9], Haptoglobin precursor, Profilin-1 (Profilin I), Serum albumin precursor, Fibronectin precursor (FN) (Cold-insoluble globulin), Brain acid soluble protein 1 (BASP1 protein), Glyceraldehyde-3-phosphate dehydrogenase, Vitamin D-binding protein precursor (DBP) were significantly more abundant in IAI.

Preterm birth without IAI versus Preterm birth with IAI—A comparison of PTB without IAI and with IAI showed 27 proteins with statistically significant (p<0.05) differential abundance (Table 11). Twenty three proteins including, Haptoglobin precursor, Profilin-1 (Profilin I), Brain acid soluble protein 1 (BASP1 protein), Fructose-bisphosphate aldolase A, Glyceraldehyde-3-phosphate dehydrogenase, Catalase (EC 1.11.1.6), Alpha-actinin 4 (Non-muscle alpha-actinin 4), Myosin-9 (Myosin heavy chain, nonmuscle IIa), Serum albumin precursor, Vitamin D-binding protein precursor (DBP), Matrix metalloproteinase-9 precursor (MMP-9) kDa matrix metalloproteinase-9], Calgranulin C (CAGC) (CGRP) (Neutrophil S100 protein), Thymosin beta-4 (T beta 4), Lysozyme C precursor (EC 3.2.1.17), Cystatin B (Liver thiol proteinase inhibitor), Serotransferrin precursor (Transferrin), Alpha-1-acid glycoprotein 1 precursor (AGP 1), Beta-2-glycoprotein I precursor (Apolipoprotein H), Nonsecretory ribonuclease precursor, Alpha-2-HS-glycoprotein precursor (Fetuin-A), Alpha-1B-glycoprotein precursor (Alpha-1-B glycoprotein), Peptidoglycan recognition protein precursor (SBBI68) (PGRP-S), Annexin A3 (Annexin III) (Lipocortin III) were more abundant in PTB with IAI. S100 calcium-binding protein A2. (S-100L protein) (CAN19), Tropomyosin alpha 3 chain (Tropomyosin 3), Lactotransferrin precursor (Lactoferrin), Small proline-rich protein 3 (Cornifin beta), Kallikrein 13 precursor, Fatty acid-binding protein, epidermal (E-FABP), Histone H4, Heat-shock protein beta-1 (HspB1) (Heat shock 27 kDa protein), Annexin A1 (Annexin I) (Lipocortin I), Thioredoxin (ATL-derived factor) (ADF), Periplakin (195 kDa cornified envelope precursor protein), Heat shock cognate 71 kDa protein (Heat shock 70 kDa protein 8), Mucin-5B precursor (Mucin 5 subtype B, tracheobronchial), Involucrin, Neuroblast differentiation associated protein AHNAK, Fibronectin precursor (FN) (Cold-insoluble globulin) (CIG), Annexin A2 (Annexin II) (Lipocortin II), Squamous cell carcinoma antigen 1 (SCCA-1), S100 calcium-binding protein A7 (Psoriasin) were more abundant in PTB without IAI.

Discussion

As discussed above, characterization of the CVF proteome and identification of a significant number of proteins differentially expressed in IAI complements the sensitive proteomic approaches used to identify biomarkers and their potential value in development of non-invasive testing for IAI. Much can be learned about the pathogenesis of IAI by analysis of temporal and quantitative samples from CVF, AF, and maternal serum. Our observations are consistent with the hypothesis that, during infection-associated preterm birth, there is a disruption of the extracellular matrix at the chorio-decidual interface, and that inflammatory mediators produced at this interface reach the vaginal pool, possibly in association with a breakdown in cervical barriers.

In summary, we utilized two complimentary proteomic approaches to characterize the global expression of cervical-vaginal proteins and to identify potential biomarkers of IAI in cervical vaginal fluid. Distinct immunoregulatory peptides were identified that were differentially expressed in CVF following experimental IAI. The differential expression of these peptides was confirmed with immunoassay, and provides an opportunity for the development of non-invasive reliable tests for the diagnosis of IAI.

Example 19

Protocols for Identification of Novel Protein Biomarkers of Preterm Birth in Human Cervical Vaginal Fluid (CVF)

Sample Collection and Processing.

This study was approved by the Oregon Health & Science University Institutional Review Board. All subjects were identified prospectively and gave informed written consent to participate in the study. PTL was defined as the combination of regular uterine activity with cervical dilation prior to 37 weeks gestation, and preterm birth was defined as a spontaneous delivery occurring prior to 37 weeks gestation. No patient had clinical evidence of intra-amniotic infection.

Eighteen subjects (n=6 in each group) were recruited, at a mean GA of 26.9 weeks±7.5 SD (range 15.8-35.9). The mean maternal parity was 0.8, and 20% of subjects had a prior preterm birth. Human CVF samples were collected by placing 2 sterile 6-inch Dacron-tipped plastic applicators (Solon, Skowhegan, Me.) into the posterior vaginal fornix and rotating them for 15 seconds during a sterile speculum examination. Following collection, protein was extracted into phosphate-buffered saline containing a protease inhibitor cocktail (Roche Diagnostics, Alameda, Calif.). Samples were spun down after extraction to remove any debris and cellular material, and the supernatant was stored at −70° C.

For MudPIT analysis, five maternal CVF samples (100 µl×5) each of Control, PTL without preterm delivery, and SPTB without infection were individually pooled and acetone-precipitated. 490 µg of each pooled sample was dissolved in 10 mM Tris, pH 8.5. For 2-D-DIGE experiments, 50 µg each of GA-matched control, PTL, and SPTB (GA 29-34 weeks) samples were used.

Fluorescence Two-Dimensional Differential In-Gel Electrophoresis (2D-DIGE).

GA-matched control/PTL/SPTB (29-34 weeks) sample pairs were chosen. For each sample, 50 mg of CVF protein was labeled with CyDye DIGE Fluor minimal dye (GE Healthcare Biosciences, Piscataway, N.J.) at a concentration of 400 pm of dye/50 mg of protein. Cy2, Cy3, and Cy5 dyes were used to label control, PTL, and SPTB, respectively, and all three labeled samples were multiplexed and resolved in one gel. Labeled proteins were purified by acetone precipitation, dissolved in IEF buffer and rehydrated on to a 24-cm IPG strip (pH 4-7) for 12 hrs at room temperature. The IPG strip was subjected to 1-dimensional electrophoresis at 65-70 kV hrs, and then equilibrated with DTT and IAA equilibration buffers for 15 minutes sequentially. Second-dimension 8-16% SDS-PAGE was conducted at 80-90 V for 18 hrs.

Gels were scanned in a Typhoon 9400 scanner (Amersham Biosciences) using appropriate lasers and filters with PMT voltage set between 550-600. Images in different channels were overlaid using pseudo-colors, and differences were visualized using ImageQuant software (Amersham Biosciences). 2D-gel image analysis to identify differentially abundant protein spots was performed using Phoretix 2D evolution, version 2005 (Non-Linear Dynamics, Ltd.). A fixed area was selected from every gel, and a cross-stain analysis protocol was performed. Background subtraction was done using the 'mode of non spot' method, and images were wrapped to maximize the spot matching. A ratiometric normalization algorithm was applied to account for potential concentration differences in protein labeling. Normalized protein spots in the Cy5 and Cy3 channels were compared to the internal standard (Cy2) to generate a ratio of relative amount. The statistical significance of differences in the intensity of protein spots was determined by t-tests on the averaged gels for each group. Protein spots with a relative ratio >2.0 and a t-test value of <0.05 were considered significant.

For the identification of proteins in spots of interest, preparative 2D electrophoresis (2DE) was performed using 700 µg of CVF protein, and gels were stained with Coomassie Blue R-250 or silver stain. Individual spots were excised from the gel, destained, and subjected to in-gel digestion with trypsin for 16-18 hr at 37° C. Peptides were extracted in ammonium bicarbonate and then filtered with a 0.22-mm MultiScreen filter plate (Millipore, Billerica, Mass.). Filtered solutions were dried down and reconstituted in 5% formic acid for analysis by mass spectrometry.

Polyclonal antibodies and western immunoblotting. Immunogenic peptides and/or recombinant proteins were used to generate rabbit and goat polyclonal antibodies (DSL Laboratories, Webster, Tex.). Affinity-purified antibodies were then used for western blots. Fifty µg of CVF protein was resolved on 4-20% SDS-PAGE and transferred to PVDF membranes. Membranes were blocked in Sea Block (Pierce) and incubated with 1 µg/ml primary antibody (IGFBP-1, calgranulin-A, calgranulin-B, anexin V, or profilin1) overnight at 4° C. After three washes with TBST, the membranes were incubated with appropriate secondary antibodies tagged with Cy dyes for 1 hr in the dark with constant rocking and subsequent washing. Visualization of specific protein bands was done using a Typhoon 9400 variable mode imager (GE Healthcare, Piscataway, N.J.).

Multidimensional Liquid Chromatography Tandem Mass Spectrometry (LC-LC-MS/MS; MudPIT) Analysis.

490 µg each of individually pooled control, PTL, and uninfected SPTB CVF samples were dried and dissolved in 100 µl of digestion buffer containing 8 M urea, 1 M Tris base, 100 mM methylamine, and 10 mM $CaCl_2$ (pH 8.5). Samples were reduced and alkylated by first incubating at 50° C. in 12.5 µl of 0.9 M DTT for 15 min and, then, in 25 µl of 1.0 M iodoacetamide in dark at room temperature for another 15 min. An additional 12.5 µl of 0.9 M DTT along with 210 µl of water and 1N NaOH was added to the solution to adjust its pH to 8.5. Samples were digested with 40 µl of 1 mg/ml trypsin (Promega) stock solution overnight at 37° C. Digestion was stopped with 40 µl of formic acid and desalted using C18 SepPak Plus cartridges. Digests (1 ml) were injected onto a polysulfoethyl strong cation-exchange column (2.1-mm ID×100 mm, 5-µm particle size and 300-Å pore size (The Nest Group, Southborough, Mass.) and fractionated using an HPLC equipped with a UV detector and a fraction collector. Solvent A was 10 mM potassium phosphate (pH 3) with 25% acetonitrile (ACN), and solvent B was 10 mM potassium phosphate (pH 3), 350 mM KCl with 25% ACN. A 95-min. gradient at a flow rate of 200 ml/min was employed for fractionation of peptides. A total of 80 fractions were collected, evaporated and resuspended in 100 ml of 0.1% TFA for desalting using a 96-well Vydac C18 silica spin plate (The Nest Group, Southborough, Mass.). Fractions were eluted in 80% ACN/0.1% formic acid (FA), evaporated, and resuspended in 20 ml of 5% FA and 5 ml of each fraction was analyzed on a Q-Tof-2 mass spectrometer connected to a CapLC (Waters, Inc., Milford, Mass.).

Mass Spectrometry

2D-LC fractions and gel digests were further separated using a Nanoease C18 75-µm ID×15-cm fused silica capillary column (Waters, Inc.) and a 95-min water/ACN gradient. The mass spectrometer was calibrated using Glu1Fibrinopeptide B. An MS/MSMS survey method was used to acquire spectra. Masses from m/z 400 to 1500 were scanned for MS survey and masses from m/z 50 to 1900 for MS/MS. A total of 10,824 MS/MS spectra were acquired from the 2D-LC fractions. Raw MS/MS spectra were pre-processed with ProteinLynx Global Server v.2.1 software (Waters, Inc.).

An average of 3,645 MS/MS spectra from each sample were searched against a combined database containing known contaminants (keratin & albumin), forward and reverse entries of the SwissProt™ human database (version 46.6). The peptide identification searches were performed using three independent search engines: TurboSequest (ThermoFinnigan, Waltham, Mass.), X! Tandem (Craig, R. and Beavis, supra), and OpenSea (Wenstrom, K. D., Am J Obstet.

Gynecol. 175, 830-3 (1996); Ghidini, A. et al., Am J Reprod Immunol 37, 227-31 (1997). Sequest™ and X! Tandem are database search engines that match experimental spectrum to theoretical spectrum generated from a theoretical enzymatic digest of the protein database. OpenSea is a de novo sequence-based search engine that performs an error-tolerant matching between inexact de novo sequences and protein sequences in the database. Peaks software (Bioinformatics Solutions, Ontario, Calif.) was used to provide de novo sequences to the OpenSea search engine. Peptide identifications from individual search engine results were combined into protein identifications using probabilistic protein identification algorithms implemented in Scaffold (Version: 1.3.2, Proteome Software, Portland, Oreg.). Protein identifications that had at least two independent peptide identifications (probability >=0.9) were considered to be present in the sample.

Quantitation Using Spectral Counts and Statistical Analysis.

Spectral counting, the total number of MS/MS spectra matched to a particular protein, has been used to access its relative abundance in a sample Liu, H., et al., *Anal Chem.* 76, 4193-201. (2004); Zybailov, B., et al., *Anal Chem.* 77, 6218-24. (2005); Old, W. M. et al., *Mol Cell Proteomics*. 4, 1487-502. Epub 2005 Jun. 23. (2005)). This method has been used to efficiently detect the abundance differences of proteins between two samples without resorting to isotopic labeling (Julka, S. & Regnier, F. *J Proteome Res* 3, 350-63 (2004)). All proteins in a sample with more than two confident peptide identifications were considered for protein quantitation using spectral counts. The protein lists of the samples were further curated by collapsing the spectral counts of similar proteins (e.g., immunoglobulins, α-1-acid glycoproteins 1 and 2, etc.) into a single entry.

Pair-wise comparison was performed using $\chi^2$ goodness-of-fit tests to assess whether there were significant differences between the groups (control, PTL, or SPTB) in the spectral counts for each protein. Statistical significance for each protein was determined after adjusting for multiple comparisons via the false-discovery rate (FDR) method (Benjamini, Y. & Hochberg, Y., *Journal of the Royal Statistical Society* B, 289-300 (1995)) and the level of significance was set at 0.05 (SAS version 9.1). To reduce the false-positive rate of differentially abundant proteins, only statistically significant proteins that had at least two independent peptides matched to at least four MS/MS spectra (probability $\geq 0.8$) in at least one of the samples were considered as truly differentially abundant. Fold changes of proteins passing the above criteria were determined using a published formula for calculating spectral count ratios (Old, W. M. et al., supra).

Progressive differences in the relative abundance of each protein from the control to PTL to SPTB groups were assessed by fitting generalized linear regression models with a log link function and Poisson distributed errors (i.e., Poisson regression) (Agresti, A. *An Introduction to Categorical Data Analysis*, (John Wiley & Sons, Inc, New York, 1996). Orthogonal polynomial contrasts were used to test whether there was an increasing or decreasing trend across the ordinal subject groups. The level of significance was set at 0.05, and, as above, adjustments for multiple comparisons were made via the FDR method. Significant trends were confirmed by evaluating regression coefficients of PTL versus control and SPTB versus control groups (i.e., model-based fold changes). These analyses were conducted using the GENMOD procedure in SAS version 9.1.

Example 20

Identification of Novel Protein Biomarkers of Preterm Birth in Human Cervical Vaginal Fluid (CVF)

Following the protocols described in Example 19, the following results were obtained.

Results

CVF proteome—Analysis of a total of 10,824 MS/MS spectra using multiple search engines identified 205 unique proteins in CVF listed in the attached Table 6. Functional annotation of these proteins revealed that metabolism (25%), immune response (23%), and transport (18%) were the major categories represented in CVF.

A comparison of control versus PTL showed 21 proteins with statistically significant ($p<0.05$) differential abundance. The differential presence of these proteins ranged from +28-fold to −18-fold. Eight proteins, S100 calcium-binding protein A7, mucin-5B precursor, calgizzarin, histone H2B, histone H1.2 (histone H1d), L-lactate dehydrogenase A chain, rho GDP-dissociation inhibitor 2, and 14-3-3 δ were up-regulated by >3-fold in PTL. S100 calcium-binding protein A7, a development and cell differentiation protein, was the most significantly over-expressed protein (28-fold) in PTL compared to control. Three proteins, desmoplankin (−18-fold), periplakin (−4-fold), and junction plakoglobin (desmoplakin III) (−3-fold) were significantly down-regulated in PTL.

Control versus SPTB—A comparison of control vs SPTB showed 30 proteins with statistically significant ($p<0.05$) differential abundance. Seven proteins, α-1-antitrypsin precursor, calgranulin C, annexin A5 (annexin V), rho GDP-dissociation inhibitor 2, vitamin D-binding protein precursor (DBP), α-1-acid glycoprotein 1 precursor, and L-plastin (lymphocyte cytosolic protein 1) were up-regulated by > 3-fold in SPTB. Alpha-1-antitrypsin, a protease inhibitor, was the most significantly over-expressed protein (16-fold), followed by calgranulin C (~16-fold) and annexin A5 (8.5-fold) in SPTB. Six proteins, desmoplakin (DP), peptidyl-prolyl cis-trans isomerase A, junction plakoglobin (desmoplakin III), heat-shock protein β-1, periplakin, and epidermal fatty acid-binding protein, were down-regulated by >3-fold in SPTB.

PTL without delivery versus SPTB—A comparison of PTL versus PTB showed 25 proteins with statistically significant ($p<0.05$) differential abundance. Four proteins, α-1-antitrypsin precursor (8.5-fold), calgranulin C (6.2-fold), annexin A5 (annexin V) (4.9-fold), and kinninogen (4.5-fold) were-up regulated by >3-fold in PTB CVF. Eight proteins, S100 calcium-binding protein A7 (−13-fold), 14-3-3 σ (−10.1-fold), histone H2B (−9.2-fold), peptidyl-prolyl cis-trans isomerase A (−8.3-fold), L-lactate dehydrogenase A chain (−7.4-fold), histone H1.2 (−4.6-fold), cystatin B (−4.2-fold), and histone H4 (−4.1-fold), were down-regulated by > 3-fold in SPTB compared to PTL.

Trend analysis—In order to estimate the trend and linearity of the relative abundance of common proteins found in control, PTL, and SPTB, a GENMOD linear regression model (SAS version 9.1) was used by fitting generalized linear regression models with a log link function and Poisson distributed errors (i.e., Poisson regression). The level of significance was set at 0.05, and adjustments for multiple comparisons were made via the FDR method. Sixteen proteins were found to be differentially ($p<0.003$) present in all three samples (Table 8). Thirteen proteins consistently showed a statistically significant increase in SPTB>PTL without delivery>control. Only three proteins, epidermal fatty acid-binding protein, heat-shock protein beta-1, and desmoplankin showed a decrease in SPTB<PTL without delivery<control.

2D-DIGE analyses of control, PTL, and SPTB CVF. Two-dimensional gel electrophoresis has been widely used to characterize the serum proteome (Chromy, B. A. et al., *Journal of Proteome Research* 3, 1120-7 (2004)) to identify biomarkers for cancer and other diseases. To enhance sensitivity, reproducibility, and detection over a wide dynamic range, we utilized a multiplex proteomic analysis approach to label proteins with fluorescent cyanine dyes. Three GA-matched controls, PTL, and SPTB CVF (GA 29-34 weeks) were labeled with Cy3, Cy5, and Cy2, respectively. Each labeled GA-matched sample pair was resolved in the same gel. Intensity of the green or red colors indicates the differentially abundant protein levels and yellow represents comparatively similar abundance. Pseudo-color visualization of control/PTL/PTB gel maps (ImageQuant; GE Healthcare), showed a distinct pattern of up-regulation of proteins in PTL/SPTB (FIGS. 26A, 26B, and 26C).

A quantitative analysis of the CVF proteome resolved by 2D-DIGE was done using Phoretix 2D evolution software. The use of an internal standard (Cy2) as the third channel increased the quality of the analysis by providing references for spot normalization and matching. The spot-quantification protocol matched on average 590 spots in pairwise comparisons. Seventeen proteins were differentially present by more than two-fold in PTL without delivery and SPTB CVF samples.

Eleven proteins were up-regulated, and six proteins were down-regulated in SPTB when compared with PTL without delivery. Protein identification from the gel spots revealed that 14-3-3δ, or stratifin, showed the highest over-expression (11-fold), followed by annexin A2 (7.5-fold), cystatin A (5.7-fold), calgranulin B (4-fold), and cellular retinoic acid-binding protein 2 (3.9-fold). Involucrin was highly down-regulated (15-fold), followed by epidermal fatty acid binding protein (6.3-fold) and cytoplasmic actin 2 (2.9-fold) in the SPTB sample.

Figure 27:
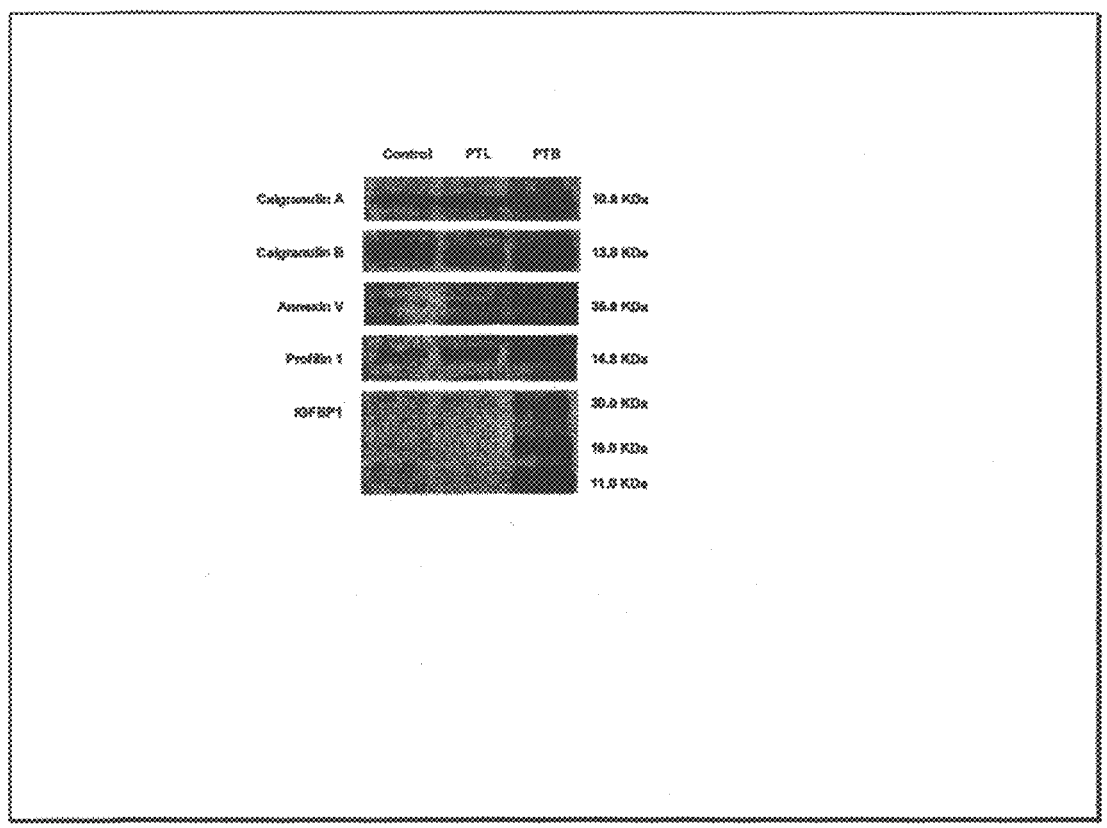
FIG. 27. Immunodetection of biomarkers of spontaneous preterm birth in human CVF. 50 μg of CVF protein representing each sample group was blotted and probed with specific antibodies. IGFBP-1 bands represent intact protein (~30 kDa) and proteolytic fragments (~16 and ~11 kDa).

MudPIT experiments revealed many differentially abundant SPTB biomarkers with high confidence (>90%), some of them complementary to the 2D-DIGE experiments. The differentially abundant proteins common between 2D-DIGE and MudPIT were 14-3-3δ, calgranulin B, S100 calcium binding protein A7, α-1-antitrypsin and cystatin A. MudPIT additionally identified many smaller differentially abundant proteins that were difficult to separate and visualize using 2D gel conditions. Furthermore, as a result of the all-liquid fractionation, better sequence coverage was obtained for many of the identified proteins in MudPIT versus the 2D gel experiments. Immunoblotting with specific antibodies for calgranulins, annexin V, and profilin 1 confirmed the consistent trends (FIG. 27) observed in MudPIT analysis. IGFBP-1 exhibited a distinct proteolytic pattern and higher levels of expression in SPTB. The majority of the IGFBP-1 detected corresponded to a low-molecular-weight, 11-kDa proteolytic fragment previously described as an amniotic fluid biomarker for intra-amniotic infection (Gravett, M. G. et al. *Jama* 292, 462-9 (2004)).

Discussion

Spontaneous preterm birth (SPTB) is a major problem in perinatal medicine worldwide and is the leading cause of perinatal deaths not attributable to congenital malformations. An estimated 8 million perinatal deaths occur annually, primarily due to prematurity and neonatal sepsis (Lawn, J., McCarthy, B. & Ross, s. *The Healthy Newborn: a Reference Manual for Program Managers*. (ed. Centers for Disease Control, C.) (Atlanta, 2001); WHO. 2001 *Estimates in: Saving Newborn Lives. State of the World's Newborns*. 1-49 (World Health Organization/Save the Children Federation-US, Washington, D.C., 2001). The rate of SPTB has not decreased over the last three decades, in spite of improved healthcare (Smith, R., et al., *Regul Pept* 108, 159-64 (2002)), and in the U.S., the rate of SPTB has continuously increased over the past 25 years to a rate of 12.5% in 2004 (National Vital Statistics 2004). Numerous studies have attempted to identify markers of STPB. Associations between epidemiologic risk factors, cervical length, cervical-vaginal fetal fibronectin (fFN) single nucleotide polymorphisms, maternal medical conditions, vaginal infections, and protein biomarkers in amniotic fluid and other biologic fluids have been analyzed in the hope of developing a useful model for the positive prediction of SPTB. To date, however, no robust marker has been validated for general clinical use.

Several biological fluids, including CVF, saliva, and/or plasma have all been used as a source to detect markers for SPTB. However, none of these markers were found to be good predictors of preterm delivery. Various hormones in saliva have been evaluated as potential biomarkers of SPTB. Of these, only salivary estriol has been shown to be a marker for SPTB, usually beyond 32 weeks of gestation (Ramsey, P. S. & Andrews, *Clin Perinatol* 30, 701-33 (2003); McGregor, J. A. et al. *Am J Obstet Gynecol* 173, 1337-42 (1995); Heine, R. P. et al. *Obstet Gynecol* 96, 490-7 (2000)). Since infants delivered beyond 32 weeks of gestation are at low risk for neonatal morbidity and death compared to infants delivered at earlier GAs, the clinical usefulness of this marker is limited. Serum or plasma components have been evaluated extensively for markers of SPTB. Goldenberg et al. (Goldenberg, R. L. et al., *Am J Obstet Gynecol* 185, 643-51 (2001); Goldenberg, R. L. et al., *Am J Obstet Gynecol* 182, 625-30 (2000)) have shown that a serum granulocyte colony-stimulating factor (G-CSF) level above the $75^{th}$ percentile and serum ferritin level above the $90^{th}$ percentile are among the strongest predictors of SPTB. High α-fetoprotein, alkaline phosphatase, and high corticotrophin-releasing hormone levels are also potential serum markers of SPTB (Moawad, A. H. et al., *Am J Obstet Gynecol* 186, 990-6 (2002); McLean, M. et al., *Am J Obstet Gynecol* 181, 207-15 (1999)). Several substances in CVF have been previously evaluated as possible biomarkers for SPTB. Of all the markers to date, only fFN in the cervix or vagina has been shown to be a reliable negative predictor for SPTB at approximately 24 to 26 weeks of gestation (Goldenberg, R. L. et al. *Obstet Gynecol* 87, 643-8 (1996)) in women with symptoms of preterm PTL. However, at other gestational ages, particularly prior to 24 weeks, fFN has a low sensitivity for SPTB (<20%) Honest, H., et al., *Bmj* 325, 301 (2002)).

The multiple proteomic approaches employed in this study identified distinct sets of proteins that were differentially abundant in CVF of women delivering preterm compared to those with SPTL who delivered at term (Table 9 and Table 10). Pair-wise comparisons of asymptomatic controls with PTL and SPTB for the first time revealed the presence of a unique set of markers for PTL that are distinct from SPTB (Table 9). It is likely that further studies of these potential PTL markers will facilitate a better understand the mechanism of PTL and provide new avenues for therapy.

Progressive analysis (trend analysis) revealed a potential list of markers that exhibited a gradual increase from asymptomatic controls to SPTB. These markers could be beneficial to monitor the risk of SPTB through serial measurements. Trend analysis identified the S100 proteins as one group of molecules showing significant statistical differences. The S100 proteins calgranulins A, B, and C have been previously described as differentially present in maternal serum and amniotic fluid of women with SPTB, and are generally up-regulated in the setting of infection and inflammation (Gravett, M. G. et al. *Jama* 292, 462-9 (2004)). S100 proteins are though to modulate biologic activity via calcium binding (Ikura, M., *Trends Biochem Sci* 21, 14-7 (1996)), and increased levels of S100 proteins in neonatal CSF, blood, and urine have been associated with neonatal brain damage (Blennow, M., et al., *Acta Paediatr* 90, 1171-5 (2001); Sellman, M. et al. *Scand J Thorac Cardiovasc Surg* 26, 39-45 (1992)). The differential abundance of S100 proteins in our study may reflect the increased prevalence of sub-clinical intra-amniotic infection and inflammation in women with PTL resulting in SPTB compared to those who go to term. Although none of our patients had clinical evidence of intra-amniotic infection, amniocentesis was not routinely performed to exclude this possibility. Similarly, trend analysis also showed the presence of negative predictors of SPTB, including epidermal fatty acid binding protein, heat shock protein beta-1, and desmoplakin (Table 9). It is possible that immunoassays assessing both up- and down-regulated proteins will convey even greater sensitivity and specificity to the diagnosis of SPTB.

Important acute-phase reactants exhibited increasing abundance in our pair-wise comparisons and trend analysis (Tables 8 and 9). These included-1-acid glycoprotein (A1AG), α-1-antitrypsin precursor, and annexins A3 (annexin III) and A5 (annexin V). Elevated levels of A1AG have been previously reported prior to delivery in rhesus macaques (Golub, M. S. & Kaaekuahiwi, M. A. *Clin Chim Acta* 262, 29-37 (1997)), while α-1-antitrypsin, a glycoprotein protease inhibitor released by leukocytes in response to inflammatory stimuli, appears to play an important role in maintenance of the uterine surface and placental attachment (Geisert, R. D., et al., *Reproduction* 126, 621-7 (2003)). The production of α-1-antitrypsin by human trophoblastic tissue has been demonstrated (Bergman, D. et al. Synthesis of alpha 1-antichymotrypsin and alpha 1-antitrypsin by human trophoblast. *Pediatr Res* 34, 312-7 (1993)). The physiologic role of annexin III has not been fully determined; however, its proposed function as a mediator of intracellular calcium signaling and transmembrane calcium transportation, as well as its presence in the placenta and in neutrophils (Le Cabec, V., et al., *Biochemical and Biophysical Research Communications* 189, 1471-1476 (1992)), support a possible role for this protein in the pathophysiology of SPTB. Annexin V has been implicated in pregnancy loss (Rand, J., Eerden, et al., *Thromb Res* 115 Suppl 1, 77-81 (2005)), preeclampsia, and intra-uterine growth restriction (Bretelle, F. et al. *Thromb Haemost* 89, 486-92 (2003)), suggesting a possible mechanistic role for annexin 5 in decidual infarction/placental-mediated PTL.

Several CVF proteins that were differentially abundant in PTL and SPTB are integral to cytoskeletal structure, arrangement, and motility. Profilin-1, rho GDI 2, and thymosin β-4 are all involved in the organization and biogenesis of the actin cytoskeleton and were up regulated in SPTB. Profilin-1, rho GDI 2, and thymosin have also been implicated in either the inhibition of actin polymerization or disruption of the actin cytoskeleton (Honore, B., *FEBS Lett* 330, 151-5 (1993)). Profilin-1 is also known to bind to poly-L-proline motifs (Witke, W. *Trends Cell Biol* 14, 461-9 (2004)) and has been implicated in host-pathogen interactions. *Listeria* and *Shigella* bacteria produce profilin-1-binding proteins that enable them to use the host-cell cytoskeleton for invasion of neighboring cells (Witke, supra). Involucrin is an epithelial structural protein and is a marker of early differentiation of epidermal cells. It has been used as a biomarker of early differentiation in the cervix in chemoprevention trials (Mitchell, M. F. et al., *J Cell Biochem Suppl* 23, 104-12 (1995)).

This study provides the most comprehensive analysis to date of differential protein profiles in the CVF of asymptomatic control subjects compared to those in PTL who deliver at term and those with SPTB. MudPIT and 2D-DIGE both revealed several proteins that were significantly differentially abundant in PTL and SPTB samples. The findings of this study, however, are based on a limited number of samples and must be validated in a larger cohort. Furthermore, despite the biologic plausibility of several of our observations, the possibility exists that some of our findings are due to random biologic variation. To minimize this possibility, we considered only proteins in which the spectral count and fold change yielded a p value <0.001 and performed pair-wise comparisons amongst control, PTL, and SPTB groups as well as a trend analysis to identify differential expression from control <PTL<SPTB. The findings of this study have potential implications for the clinical practice of obstetrics if one or more of these proteins can be modeled for clinical use. Currently the most widely utilized cervical-vaginal marker for SPTB is fFN, a biomarker with good specificity but poor sensitivity. Compared to fFN, we identified several proteins with greater differential expression than fFN when comparing both the asymptomatic group and PTL group to the SPTB group. Among these are several of the proteins discussed above, including calgranulin C, α-1-acid glycoprotein, α-1-antitrypsin precursor, and annexin V.

The identification of novel protein biomarkers of SPTB represents an important step forward in advancing our understanding of the physiologic perturbations that lead to preterm birth. We acknowledge that our findings should be considered preliminary until validated in a larger cohort and that to be clinically significant, the utility of these markers in practice must be better than currently available tests. However, in order to reverse the trend of the last 25 years, which has seen the rate of SPTB steadily rise in the U.S., innovative treatment strategies based upon the reliable identification of women at high-risk for preterm birth must be developed.

Throughout the foregoing description the invention has been discussed with reference to certain embodiments, but it is not so limited. Indeed, various modifications of the invention in addition to those shown and described herein will become apparent to those skilled in the art from the foregoing description and fall within the scope of the appended claims.

All references cited throughout the description, and the references cited therein, are hereby expressly incorporated by reference in their entirety.

TABLE 1A

Characteristics of the Study Population

| Characteristic | GROUP 1 PMD with IUI (n = 11) | GROUP 2 PMD without IUI (n = 11) | GROUP 3 PML with subsequent term delivery (n = 11) | GROUP 3 vs 1 p value |
|---|---|---|---|---|
| Maternal Age | 24.5 ± 5.4 | 26.6 ± 9.0 | 25.6 ± 6.0 | NS |
| White Race | 6(55%) | 4(36%) | 6(55%) | NS |
| Parity | 1.9 ± 1.6 | 1.9 ± 1.5 | 3.0 ± 2.5 | NS |
| Nulliparity | 3(27%) | 1(9%) | 1(9%) | NS |
| Gestational Age at Enrollment (wks) | 26.9 ± 1.1 | 28.6 ± 1.1 | 30.3 ± 1.1 | 0.10 |
| Gestational Age at Delivery (wks) | 27.3 ± 0.9 | 29.8 ± 1.0 | 37.0 ± 0.9 | <0.0001 |
| Enrollment to Delivery Interval (days) | 2.1 ± 5.6 | 8.4 ± 6.3 | 46.9 ± 5.6 | <0.0001 |
| Delivery. 7 days | 10(91%) | 6(55%) | 0 | <0.001 |

TABLE 1B

Screening Results.

| Characteristic | GROUP 1 PMD with IUI (n = 11) | GROUP 2 PMD without IUI (n = 11) | GROUP 3 PML with subsequent term delivery (n = 11) p valueL GROUPS 3 VS 1 |
|---|---|---|---|
| Bacterial culture positive | 4/11 | 0/11 | 0/11 $p < 0.01$ |
| IL-6 positive | 7/11 | 0/11 | 0/11 $p < 0.01$ |
| Diagnostic protein profiles | 11/11 | 2/11* | 0/11 $p < 0.01$ |

TABLE 1C

Fisher's test significance values for screening test results.

Fisher's Exact: PMD with IUI vs PML $p < 0.05$ (one-sided)

| Class | Bacterial Culture | | |
|---|---|---|---|
| | Positive | Negative | Total |
| PMD with IUI | 4 | 7 | 11 |
| PML, term delivery | 0 | 11 | 11 |
| Total | 4 | 18 | 22 |

Fisher's Exact: PMD with IUI vs PML $p < 0.01$ (one-sided)

| Class | IL-6 Status | | |
|---|---|---|---|
| | Positive | Negative | Total |
| PMD with IUI | 7 | 4 | 11 |
| PML, term delivery | 0 | 11 | 11 |
| Total | 7 | 15 | 22 |

TABLE 1C-continued

Fisher's test significance values for screening test results.

Fisher's Exact: PMD with IUI vs PML $p < 0.005$ (one-sided)

| Class | Diagnostic Protein Profile | | |
|---|---|---|---|
| | Positive | Negative | Total |
| PMD with IUI | 11 | 0 | 11 |
| PML, term delivery | 0 | 11 | 11 |
| Total | 11 | 11 | 22 |

Fisher's Exact: PMD with IUI vs PMD without IUI $p < 0.005$ (one-sided)

| Class | Diagnostic Protein Profile | | |
|---|---|---|---|
| | Positive | Negative | Total |
| PMD with IUI | 11 | 0 | 11 |
| PMD without IUI | 2 | 9 | 11 |
| Total | 13 | 9 | 22 |

Fisher's Exact: PMD without IUI vs PML p n.s.

| Class | Diagnostic Protein Profile | | |
|---|---|---|---|
| | Positive | Negative | Total |
| PMD without IUI | 2 | 9 | 11 |
| PML, term delivery | 0 | 11 | 11 |
| Total | 2 | 20 | 22 |

TABLE 2

Proteins and polypeptides discovered for the first time in the human amniotic fluid

| GenBank™ Acc. No | Protein ID | Protein Name |
|---|---|---|
| | | Immune response related genes |
| U12026 | CAPG_HUMAN | Macrophage capping protein # |
| X83006 | NGAL_HUMAN | Neutrophil gelatinase-associated lipocalin # |
| M19507 | PERM_HUMAN | Myeloperoxidase precursor # |
| M22300 | PLSL_HUMAN | L-plastin (Lymphocyte cytosolic protein 1)* |
| NM001700 | AZU1_HUMAN | Azurocidin # |
| Z38026 | FA39_HUMAN | Antibacterial protein FALL-39 precursor # |
| AF159456 | Q9UKJ4 | Gp-340 variant protein |
| AL355392 | Q9H4V6 | Novel protein similar to mouse von Ebner salivary gland protein, isoform 2 |
| M93056 | ILEU_HUMAN | Leukocyte elastase inhibitor # |
| Y00278 | S108_HUMAN | Calgranulin A* # |
| X06233 | S109_HUMAN | Calgranulin B |
| | | Structural proteins |
| D00682 | COF1_HUMAN | Cofilin, non-muscle isoform |
| M69066 | MOES_HUMAN | Moesin (Membrane-organizing extension spike protein) |
| J03191 | PRO1_HUMAN | Profilin I* # |
| D44497 | CO1A_HUMAN | Coronin-like protein p57 (Coronin 1A) |
| D00017 | ANX2_HUMAN | Annexin II (Lipocortin II) |
| M15801 | FINC_HUMAN | Fibronectin precursor |
| M17783 | GDN_HUMAN | Glia derived nexin precursor # |
| | | Proteases and protease inhibitors |
| M21642 | ANT3_HUMAN | Antithrombin-III precursor |
| S66896 | SCC1_HUMAN | Squamous cell carcinoma antigen 1 |

TABLE 2-continued

Proteins and polypeptides discovered for the first time in the human amniotic fluid

| GenBank™ Acc. No | Protein ID | Protein Name |
|---|---|---|
| U19576 | SCC2_HUMAN | Squamous cell carcinoma antigen 2 |
| AB006423 | SPI2_HUMAN | Serpin I2 precursor # |
| X05978 | CYTA_HUMAN | Cystatin A (Stefin A) (Cystatin AS) # |
| U46692 | CYTB_HUMAN | Cystatin B (Liver thiol proteinase inhibitor) |
| X05607 | CYTC_HUMAN | Cystatin C precursor |
| | Transporters and binding proteins | |
| Y00856 | IBP1_HUMAN | Insulin-like growth factor binding protein 1-Proteolytic fragment (only)* |
| L10641 | VTDB_HUMAN | Vitamin D-binding protein precursor |
| J00098 | APA1_HUMAN | Apolipoprotein A-I precursor (Apo-AI) |
| X57348 | 143S_HUMAN | 14-3-3 protein sigma (Stratifin) |
| M86400 | 143Z_HUMAN | 14-3-3 protein zeta/delta |
| X04412 | GELS_HUMAN | Gelsolin precursor, plasma |
| X53961 | TRFL_HUMAN | Lactotransferrin precursor (Lactoferrin) |
| | Enzymes and other molecules | |
| V00572 | PGK1_HUMAN | Phosphoglycerate kinase 1 |
| J04173 | PMG1_HUMAN | Phosphoglycerate mutase 1 |
| X67688 | TKT_HUMAN | Transketolase |

*Proteins shown to be differentially expressed by immunoassays also.
Peptides representing these proteins are more abundantly or uniquely detected in the infected amniotic fluid.

TABLE 3

Proteins and polypeptides, previously known to be present in the amniotic fluid, identified using de novo sequencing.

| GenBank™ Acc. No. | Protein ID | Protein Name |
|---|---|---|
| KO2765 | CO3_HUMAN | Complement C3 precursor* |
| J00241 | KAC_HUMAN | Ig kappa chain C region |
| J00253 | LAC_HUMAN | Ig lambda chain C regions |
| J00228 | GC1_HUMAN | Ig gamma-1 chain C region |
| X57127 | H2BF_HUMAN | Histone H2B.f* |
| X00038 | H4_HUMAN | Histone H4* |
| J00153 | HBA_HUMAN | Hemoglobin alpha chain |
| U01317 | HBB_HUMAN | Hemoglobin beta chain |
| U01317 | HBD_HUMAN | Hemoglobin delta chain |
| M91036 | HBG_HUMAN | Hemoglobin gamma-A and gamma-G chains |
| Z83742 | H2AC_HUMAN | Histone H2A |
| M22919 | MLEN_HUMAN | Myosin light chain alkali, non-muscle isoform |
| J05070 | MM09_HUMAN | type IV collagenase precursor* |
| V00496 | A1AT_HUMAN | Alpha-1-antitrypsin precursor* |
| K01500 | AACT_HUMAN | Alpha-1-antichymotrypsin precursor* |
| M12530 | TRFE_HUMAN | Serotransferrin precursor |
| M11714 | TTHY_HUMAN | Transthyretin precursor (Prealbumin) |
| M13699 | CERU_HUMAN | Ceruloplasmin precursor* |
| X02544 | A1AH_HUMAN | Alpha-1-acid glycoprotein 2 precursor* |
| X06675 | A1AG_HUMAN | Alpha-1-acid glycoprotein 1 precursor* |
| M12523 | ALBU_HUMAN | Serum albumin precursor |
| J00098 | APA1_HUMAN | Apolipoprotein A-I precursor (Apo-AI) |

*Known markers for infection related events.

TABLE 4

| Swissprot™ Acc. No.[a] | Protein Description | PI[b] | MW[c] | Function[d] | Normalized Spectral Count[e] | AF/Serum[f] |
|---|---|---|---|---|---|---|
| P02768 | Serum albumin precursor | 5.43 | 39.30 | Transport | 18.84 | A, S |
| P01857, P01859, P01861 | Ig gamma-1 chain C region, Ig gamma-2 chain C region, Ig gamma-4 chain C region | 8.46, 7.66, 7.18 | 36.08, 35.9, 35.9 | Immune Response | 10.35 | A, S |
| Q9UBC9 | Small proline-rich protein 3 | 8.86 | 18.10 | Cell Differentiation | 8.6 | A |
| P29508, P48594 | Squamous cell carcinoma antigen 1, Squamous cell carcinoma antigen 2 | 6.35, 5.86 | 44.5, 44.8 | Metabolism | 6.3 | |
| P06702 | Calgranulin B | 5.90 | 85.60 | Immune Response | 5.82 | A, S |
| P07355 | Annexin A2 | 4.69 | 55.30 | Cell Differentiation | 5.33 | A, S |
| P04083 | Annexin A1 | 6.96 | 11.10 | Immune Response | 4.28 | A |
| Q01469 | Fatty acid-binding protein, epidermal | 6.82 | 15.00 | Metabolism | 3.97 | |
| P01834 | Ig kappa chain C region | 5.58 | 11.60 | Immune Response | 3.79 | A, S |
| P02787 | Serotransferrin precursor | 5.22 | 51.20 | Transport | 2.82 | A, S |
| P05109 | Calgranulin A | 5.98 | 22.80 | Immune Response | 1.78 | A, S |
| Q9HC84 | Mucin-5B precursor | 6.24 | 587.60 | Transport | 1.4 | A |
| P04080 | Cystatin B | 8.39 | 39.30 | Enzyme Regulator | 1.09 | A |
| P07476 | Involucrin | 7.56 | 38.40 | Cell Differentiation | 1.08 | A |
| P01040 | Cystatin A | 5.38 | 11.00 | Enzyme Regulator | 1.04 | A, S |
| P35321 | Cornifin A | 8.85 | 9.90 | Cell Differentiation | 1.03 | A |
| Q09666 | Neuroblast differentiation associated protein AHNAK | 6.29 | 312.30 | Cell Differentiation | 1 | |

TABLE 4-continued

| Swissprot™ Acc. No.[a] | Protein Description | PI[b] | MW[c] | Function[d] | Normalized Spectral Count[e] | AF/ Serum[f] |
|---|---|---|---|---|---|---|
| P01842 | Ig lambda chain C regions | 6.91 | 11.20 | Immune Response | 0.97 | A, S |
| P30740 | Leukocyte elastase inhibitor | 5.90 | 42.70 | Enzyme Regulator | 0.94 | |
| P05164 | Myeloperoxidase precursor | 6.51 | 10.80 | Immune Response | 0.84 | |
| P02788 | Lactotransferrin precursor | 6.70 | 75.10 | Immune Response | 0.82 | A, S |
| P80188 | Neutrophil gelatinase-associated lipocalin precursor | 9.02 | 20.50 | Transport | 0.81 | A, S |
| P01009 | Alpha-1-antitrypsin precursor | 5.37 | 44.30 | Immune Response | 0.76 | A, S |
| P61626 | Lysozyme C precursor | 9.28 | 14.70 | Metabolism | 0.76 | A |
| P01876, P01877 | Ig alpha-1 chain C region, Ig alpha-2 chain C region | 6.08, 5.71 | 37.6, 36.5 | Immune Response | 0.73 | A, S |
| P04792 | Heat-shock protein beta-1 | 8.58 | 35.90 | Metabolism | 0.73 | |
| P10599 | Thioredoxin | 5.44 | 23.20 | Metabolism | 0.72 | A |
| P62988 | Ubiquitin | 6.56 | 8.60 | Metabolism | 0.65 | |
| P01833 | Polymeric-immunoglobulin receptor precursor | 5.59 | 83.30 | Signal Transduction | 0.47 | A |
| P12429 | Annexin A3 | 5.37 | 70.90 | Enzyme Regulator | 0.44 | |
| Q8TDL5 | Long palate, lung and nasal epithelium protein 1 | 6.69 | 50.20 | Function Not Assigned | 0.44 | |
| P00450 | Ceruloplasmin precursor | 5.41 | 120.00 | Transport | 0.43 | A, S |
| P35326, P35325, P22532 | Small proline-rich protein 2A, Small praline-rich protein 2B, Small proline-rich protein 2D | 8.81, 8.81, 8.77 | 8, 7.97, 7.9 | Cell Differentiation | 0.41 | |
| P60709 | Actin, cytoplasmic 1 | 5.29 | 41.60 | Cell Organization | 0.38 | A, S |
| P01011 | Alpha-1-antichymotrypsin precursor | 5.33 | 47.60 | Immune Response | 0.36 | A, S |
| P22528 | Cornifin B | 8.85 | 9.90 | Cell Differentiation | 0.34 | |
| P00738 | Haptoglobin precursor | 6.13 | 45.20 | Metabolism | 0.3 | A, S |
| P62328 | Thymosin beta-4 | 5.02 | 4.90 | Cell Organization | 0.3 | A |
| P18510 | Interleukin-1 receptor antagonist protein precursor | 5.51 | 123.60 | Immune Response | 0.27 | |
| P01024 | Complement C3 precursor | 6.02 | 187.00 | Immune Response | 0.24 | A, S |
| P07737 | Profilin-1 | 4.62 | 68.40 | Cell Organization | 0.22 | A |
| P02790 | Hemopexin precursor | 8.50 | 78.10 | Transport | 0.21 | A, S |
| P14780 | Matrix metalloproteinase-9 precursor | 5.18 | 9.00 | Metabolism | 0.21 | |
| P04406 | Glyceraldehyde-3-phosphate dehydrogenase, liver | 9.30 | 52.10 | Metabolism | 0.2 | S |
| P15924 | Desmoplakin | 5.95 | 69.20 | Cell Differentiation | 0.2 | S |
| P08107 | Heat shock 70 kDa protein 1 | 4.94 | 84.50 | Metabolism | 0.19 | |
| Q9NQ38 | Serine protease inhibitor Kazal-type 5 precursor | 8.50 | 120.70 | Immune Response | 0.19 | |
| P12724 | Eosinophil cationic protein precursor | 5.63 | 36.20 | Metabolism | 0.18 | |
| P04279 | Semenogelin-1 precursor | 6.64 | 38.60 | Cell Differentiation | 0.17 | S |
| O60437 | Periplakin | 5.44 | 204.50 | Function Not Assigned | 0.16 | |
| P09211 | Glutathione S-transferase P | 5.06 | 53.50 | Metabolism | 0.16 | |
| P02749 | Beta-2-glycoprotein I precursor | 8.37 | 36.20 | Immune Response | 0.15 | A, S |
| P07108 | Acyl-CoA-binding protein | 6.99 | 47.00 | Transport | 0.15 | |
| P59665 | Neutrophil defensin 1 precursor | 6.54 | 10.20 | Immune Response | 0.15 | S |
| O60235 | Transmembrane protease, serine 11D precursor | 8.69 | 46.20 | Metabolism | 0.13 | |
| P03973 | Antileukoproteinase 1 precursor | 6.43 | 49.30 | Enzyme Regulator | 0.13 | A |
| P04075 | Fructose-bisphosphate aldolase A | 6.95 | 59.60 | Enzyme Regulator | 0.13 | |
| P14923 | Junction plakoglobin | 5.69 | 78.40 | Transport | 0.13 | S |
| P62805 | Histone H4 | 11.36 | 11.20 | Cell Organization | 0.12 | |
| P62937 | Peptidyl-prolyl cis-trans isomerase A | 7.82 | 17.90 | Metabolism | 0.12 | A |
| Q02383 | Semenogelin-2 precursor | 9.04 | 62.90 | Cell Differentiation | 0.12 | 5 |
| P02774 | Vitamin D-binding protein precursor | 5.67 | 66.40 | Transport | 0.11 | A, S |
| P07858 | Cathepsin B precursor | 8.47 | 14.90 | Metabolism | 0.11 | |
| P24158 | Myeloblastin precursor | 7.79 | 24.20 | Metabolism | 0.11 | |
| P00441 | Superoxide dismutase | 5.70 | 15.80 | Cell Differentiation | 0.1 | |
| P02763 | Alpha-1-acid glycoprotein 1 precursor | 5.00 | 21.50 | Immune Response | 0.1 | A, S |
| P02765 | Alpha-2-HS-glycoprotein precursor | 5.00 | 21.50 | Signal Transduction | 0.1 | A, S |
| P04040 | Catalase | 5.55 | 54.30 | Metabolism | 0.1 | S |
| P13796 | L-plastin | 6.42 | 95.10 | Function Not Assigned | 0.1 | A, S |
| P54108 | Cysteine-rich secretory protein-3 precursor | 8.11 | 25.50 | Immune Response | 0.1 | |
| O43707 | Alpha-actinin 4 | 5.27 | 104.80 | Cell Organization | 0.09 | |
| P06733 | Alpha enolase | 5.71 | 13.20 | Metabolism | 0.09 | |
| P11142 | Heat shock cognate 71 kDa protein | 5.01 | 70.40 | Metabolism | 0.09 | S |
| P18206 | Vinculin | 6.44 | 331.60 | Transport | 0.09 | S |
| P26038 | Moesin | 6.09 | 67.60 | Cell Organization | 0.09 | |
| P27482 | Calmodulin-related protein NB-1 | 4.30 | 16.70 | Immune Response | 0.09 | |
| P32926 | Desmoglein-3 precursor | 4.76 | 101.70 | Transport | 0.09 | |
| P67936 | Tropomyosin alpha 4 chain | 4.67 | 28.40 | Function Not Assigned | 0.09 | S |
| Q02487 | Desmocollin-2 precursor | 4.80 | 84.70 | Transport | 0.09 | |
| Q9UGL9 | NICE-1 protein | 9.13 | 9.70 | Function Not Assigned | 0.09 | |
| P00558 | Phosphoglycerate kinase 1 | 8.30 | 44.50 | Metabolism | 0.08 | |
| P01625 | Ig kappa chain V-IV region Len | 7.92 | 12.63 | Immune Response | 0.08 | A, S |
| P01871 | Ig mu chain C region | 6.35 | 49.50 | Immune Response | 0.08 | A |
| P16402 | Histone H1.3 | 11.02 | 22.20 | Cell Organization | 0.08 | |
| P63104 | 14-3-3 protein zeta/delta | 4.73 | 27.70 | Metabolism | 0.08 | A |
| P02679 | Fibrinogen gamma chain precursor | 5.24 | 48.50 | Cell Proliferation | 0.07 | A, S |
| P08311 | Cathepsin G precursor | 9.89 | 25.50 | Metabolism | 0.07 | |
| P60174 | Triosephosphate isomerase | 6.51 | 26.50 | Metabolism | 0.07 | |
| P80723 | Brain acid soluble protein 1 | 4.64 | 22.50 | Function Not Assigned | 0.07 | |
| P01617 | Ig kappa chain V-II region TEW | 5.69 | 12.30 | Immune Response | 0.06 | S |

TABLE 4-continued

| Swissprot ™ Acc. No.[a] | Protein Description | PI[b] | MW[c] | Function[d] | Normalized Spectral Count[e] | AF/ Serum[f] |
|---|---|---|---|---|---|---|
| P01620 | Ig kappa chain V-III region SIE | 8.70 | 11.80 | Immune Response | 0.06 | A, S |
| P05387 | 60S acidic ribosomal protein P2 | 4.26 | 11.50 | Metabolism | 0.06 | |
| P11021 | 78 kDa glucose-regulated protein precursor | 4.82 | 11.60 | Metabolism | 0.06 | S |
| P29373 | Retinoic acid-binding protein II, cellular | 5.43 | 15.60 | Metabolism | 0.06 | |
| O75223 | Protein C7orf24 | 5.07 | 21.00 | Function Not Assigned | 0.05 | |
| P07900 | Heat shock protein HSP 90-alpha | 5.88 | 37.80 | Transport | 0.05 | |
| P13987 | CD59 glycoprotein precursor | 5.20 | 70.20 | Signal Transduction | 0.05 | A |
| P31151 | S100 calcium-binding protein A7 | 6.26 | 11.31 | Cell Differentiation | 0.05 | |
| P31947 | 14-3-3 protein sigma | 4.68 | 27.80 | Cell Proliferation | 0.05 | S |
| P37837 | Transaldolase | 6.36 | 37.50 | Metabolism | 0.05 | |
| P47929 | Galectin-7 | 7.00 | 14.90 | Transport | 0.05 | S |
| Q16610 | Extracellular matrix protein 1 precursor | 6.19 | 58.80 | Signal Transduction | 0.05 | A, S |
| Q99880 | Histone H2B.c | 10.32 | 13.81 | Cell Organization | 0.05 | S |
| O95171 | Sciellin | 9.38 | 75.30 | Cell Differentiation | 0.04 | |
| P01028 | Complement C4 precursor | 6.66 | 192.70 | Immune Response | 0.04 | A, S |
| P01042 | Kininogen precursor | 6.34 | 71.90 | Immune Response | 0.04 | A, S |
| P04004 | Vitronectin precursor | 9.11 | 11.70 | Immune Response | 0.04 | A, S |
| P07237 | Protein disulfide-isomerase precursor | 6.11 | 9.90 | Metabolism | 0.04 | S |
| P08603 | Complement factor H precursor | 11.37 | 26.70 | Immune Response | 0.04 | A, S |
| P14618 | Pyruvate kinase, isozymes M1/M2 | 7.95 | 57.70 | Metabolism | 0.04 | |
| P20670 | Histone H2A.o | 10.90 | 13.95 | Cell Organization | 0.04 | S |
| P20810 | Calpastatin | 4.99 | 76.50 | Enzyme Regulator | 0.04 | |
| P22735 | Protein-glutamine gamma-glutamyltransferase K | 5.68 | 89.70 | Metabolism | 0.04 | |
| Q06830 | Peroxiredoxin 1 | 8.27 | 22.10 | Cell Differentiation | 0.04 | |
| Q13835 | Plakophilin 1 | 9.29 | 82.80 | Signal Transduction | 0.04 | |
| P00747 | Plasminogen precursor | 7.04 | 90.50 | Metabolism | 0.03 | A, S |
| P05386 | 60S acidic ribosomal protein P1 | 9.19 | 83.80 | Metabolism | 0.03 | |
| P08670 | Vimentin | 6.14 | 136.90 | Function Not Assigned | 0.03 | |
| P28799 | Granulins precursor | 6.43 | 63.50 | Cell Proliferation | 0.03 | |
| P30086 | Phosphatidylethanolamine-binding protein | 7.43 | 20.90 | Enzyme Regulator | 0.03 | |
| P35237 | Placental thrombin inhibitor | 5.18 | 42.60 | Enzyme Regulator | 0.03 | |
| P01591 | Immunoglobulin J chain | 4.62 | 15.60 | Immune Response | 0.02 | S |
| P02647 | Apolipoprotein A-I precursor | 5.56 | 30.80 | Metabolism | 0.02 | A, S |
| P02675 | Fibrinogen beta chain precursor | 8.54 | 55.90 | Cell Proliferation | 0.02 | A, S |
| P13639 | Elongation factor 2 | 10.72 | 15.60 | Metabolism | 0.02 | |
| P18669 | Phosphoglycerate mutase 1 | 5.46 | 17.10 | Metabolism | 0.02 | A |
| Q9UBX7 | Kallikrein 11 precursor | 9.23 | 31.03 | Metabolism | 0.02 | |
| Q9UKR3 | Kallikrein 13 precursor | 8.79 | 28.90 | Metabolism | 0.02 | |

TABLE 5

| Swissprot ™ Acc. No.[a] | Protein Description | PI[b] | MW[c] | Function[d] | Combined Spectral Count[e] | AF/ Serum[f] |
|---|---|---|---|---|---|---|
| P68104 | Elongation factor 1-alpha 1 | 9.1 | 50.11 | Metabolism | 8 | |
| P02671 | Fibrinogen alpha/alpha-E chain precursor | 5.7 | 94.91 | Cell Proliferation | 4 | A, S |
| P01597 | Ig kappa chain V-I region DEE | 9.43 | 11.65 | Immune Response | 4 | S |
| P01703 | Ig lambda chain V-I region NEWM | 9.39 | 10.9 | Immune Response | 3 | |
| P01008 | Antithrombin-III precursor | 6.32 | 52.57 | Metabolism | 2 | A, S |
| P06731 | Carcinoembryonic antigen-related cell adhesion molecule 5 precursor | 5.43 | 76.75 | Function Not Assigned | 2 | |
| Q92817 | Envoplakin | 6.56 | 231.48 | Cell Development | 2 | |
| P16401 | Histone H1.5 | 10.91 | 22.44 | Cell Organization | 2 | |
| P05204 | Nonhistone chromosomal protein HMG-17 | 10 | 9.26 | Cell Organization | 2 | |
| P30101 | Protein disulfide-isomerase A3 precursor | 5.98 | 56.75 | Metabolism | 2 | |
| Q9UL52 | Transmembrane protease, serine 11E precursor | 8.85 | 47.67 | Metabolism | 2 | |
| P05388 | 60S acidic ribosomal protein P0 | 5.72 | 34.25 | Metabolism | 1 | |
| Q05524 | Alpha enolase, lung specific | 5.78 | 49.45 | Metabolism | 1 | |
| P23528 | Cofilin-1 | 8.26 | 18.36 | Cell Organization | 1 | |
| P27816 | Microtubule-associated protein 4 | 5.32 | 120.94 | Metabolism | 1 | |
| O60504 | Vinexin | 9.48 | 75.28 | Metabolism | 1 | |

TABLE 6

Global analysis of the cervical-vaginal proteome in pregnant rhesus monkeys using multidimensional protein identification technology (MudPIT) and gel-based fractionation (1D PAGE LC-MS/MS)

| Swiss-Prot™ ID | Protein Name |
| --- | --- |
| O60218 | Aldo-keto reductase family 1, member B10 (aldose reductase) |
| O00394 | Alpha-1-antitrypsin |
| P01023 | Alpha-2-macroglobulin |
| P12429 | Annexin A3 |
| P31941 | Apolipoprotein B mRNA editing enzyme, catalytic polypeptide-like 3A |
| Q8N4F0 | Bactericidal/permeability-increasing protein-like 1 |
| P30043 | Biliverdin-reductase B (flavin reductase (NADPH)) |
| P08758 | Calphobindin I |
| P01040 | Cystatin A (stefin A) |
| O19092 | Cystatin C precursor |
| Q28514 | GST class-pi |
| P04196 | Histidine-rich glycoprotein |
| Q9BE24 | LDH muscle subunit |
| P48737 | Phosphatidylethanolamine-binding protein |
| P30086 | Prostatic binding protein |
| P03973 | Secretory leukocyte protease inhibitor (antileukoproteinase) |
| P30740 | Serine (or cysteine) proteinase inhibitor, clade B (ovalbumin), member 1 |
| Q862Z5 | Stefin B |
| Q8HXQ1 | Superoxide dismutase [Cu—Zn] |
| O15143 | Actin related protein 2/3 complex, subunit 1B, 41 kDa |
| O15511 | Actin related protein 2/3 complex, subunit 5, 16 kDa |
| P60709 | Actin, beta |
| P12814 | Actinin, alpha 1 |
| O43707 | Actinin, alpha 4 |
| P61160 | ARP2 actin-related protein 2 homolog (yeast) |
| P61158 | ARP3 actin-related protein 3 homolog (yeast) |
| P47756 | Capping protein (actin filament) muscle Z-line, beta |
| P60981 | Destrin |
| P28676 | Grancalcin, EF-hand calcium binding protein |
| P26038 | Moesin |
| P07737 | Profilin 1 |
| Q9Y6U3 | Scinderin |
| P62328 | Thymosin beta-4 |
| Q5ISQ2 | Clusterin (Fragment). |
| P31146 | Coronin, actin binding protein, 1A |
| P01033 | Erythroid potentiating activity |
| P02679 | Fibrinogen, gamma polypeptide |
| P15170 | G1 to S phase transition 1 |
| P26583 | High-mobility group box 2 |
| Q06830 | Peroxiredoxin 1 |
| P24158 | Proteinase 3 (serine proteinase, neutrophil, Wegener granulomatosis autoantigen) |
| P26447 | S100 calcium binding protein A4 (calcium protein, calvasculin, metastasin, murine placental homolog) |
| P06703 | S100 calcium binding protein A6 (calcyclin) |
| P36955 | Pigment epithelium-derived factor Precursor |
| P68293 | Apolipoprotein A-I precursor |
| P21766 | Hemoglobin alpha-1, alpha-2, and alpha-3 chains |
| Q3I1S1 | Vesicle amine transport protein 1 (Fragment). |
| P02768 | Albumin |
| P09525 | Annexin A4 |
| P80723 | Brain abundant, membrane attached signal protein 1 |
| P00450 | Ceruloplasmin (ferroxidase) |
| O00299 | Chloride intracellular channel 1 |
| P02774 | Group-specific component (vitamin D binding protein) |
| P47929 | Lectin, galactoside-binding, soluble, 7 (galectin 7) |
| P80188 | Lipocalin 2 (oncogene 24p3) |
| Q13421 | Mesothelin |
| Q9HC84 | Mucin 5, subtype B, tracheobronchial |
| P02787 | Transferrin |
| Q8HXW1 | Transthyretin |
| P18206 | Vinculin |
| O15335 | Chondroadherin |
| P60660 | LC17 |
| Q9UN36 | NDRG family member 2 |
| P37802 | Transgelin 2 |
| P15311 | Villin 2 (ezrin) |
| Q2PFY3 | Hypothetical protein (Fragment). |
| Q4R4H7 | Brain cDNA, clone: QnpA-14191, similar to human annexin A5 (ANXA5),. |
| Q4R4P0 | Brain cDNA, clone: QccE-11243, similar to human cathepsin D (lysosomal|aspartyl protease) (CTSD) |
| Q4R4U0 | Brain cDNA, clone: QccE-18356, similar to human transketolase|(Wernicke-Korsakoff syndrome) (TKT) |
| Q4R4X4 | Brain cDNA, clone: QtrA-12155, similar to human vimentin (VIM),. |
| Q4R5M1 | Brain cDNA, clone: QccE-13766, similar to human transferrin (TF),. |
| Q4R955 | Testis cDNA clone: QtsA-10685, similar to human I factor (complement)|(IF),. |
| O15144 | Actin related protein 2/3 complex, subunit 2, 34 kDa |
| O95994 | Anterior gradient 2 homolog (Xenopus laevis) |
| P00747 | Plasminogen |
| P60988 | Prolactin-inducible protein homolog precursor |
| Q7Z5L0 | Secretory protein LOC284013 |
| Q13228 | Selenium binding protein 1 |
| Q9UBC9 | Small proline-rich protein 3 |
| P35322 | Small proline-rich squamous cell marker |
| Q5VAN1 | Haptoglobin |
| P04217 | Alpha-1-B glycoprotein |
| P25311 | Alpha-2-glycoprotein 1, zinc |
| P02765 | Alpha-2-HS-glycoprotein |
| P04083 | Annexin A1 |
| P07355 | Annexin A2 |
| P08133 | Annexin A6 |
| P13928 | Annexin A8 |
| P02749 | Apolipoprotein H (beta-2-glycoprotein I) |
| P20160 | Azurocidin 1 (cationic antimicrobial protein 37) |
| P17213 | Bactericidal/permeability-increasing protein |
| P27482 | Calmodulin-like 3 |
| Q9GLV5 | Cathelin |
| Q9TS45 | Clara cells 10 kDa secretory protein |
| P10909 | Clusterin(apolipoprotein J) |
| P01024 | Complement component 3 |
| P01028 | Complement component 4B |
| P54108 | Cysteine-rich secretory protein 3 |
| P00746 | D component of complement (adipsin) |
| Q9MYJ3 | Decay-accelerating factor |
| P59665 | Defensin, alpha 3, neutrophil-specific |
| P06744 | Glucose phosphate isomerase |
| P02790 | Hemopexin |
| P01834 | Immunoglobulins |
| P02788 | Lactotransferrin |
| P17931 | Lectin, galactoside-binding, soluble, 3 (galectin 3) |
| P09960 | Leukotriene A4 hydrolase |
| P13796 | Lymphocyte cytosolic protein 1 (L-plastin) |
| P14780 | Matrix metalloproteinase 9 (gelatinase B, 92 kDa gelatinase, 92 kDa type IV collagenase) |
| P05164 | Myeloperoxidase |
| P60030 | Neutrophil defensin 1 precursor |
| P82317 | Neutrophil defensin 2 |
| P30044 | Peroxiredoxin 5 |
| Q06323 | Proteasome (prosome, macropain) activator subunit 1 (PA28 alpha) |
| P52566 | Rho GDP dissociation inhibitor (GDI) beta |
| P60031 | RMAD-3 |
| P60032 | RMAD-8 |
| P05109 | S100 calcium binding protein A8 (calgranulin A) |
| P06702 | S100 calcium binding protein A9 (calgranulin B) |
| P01009 | Serine (or cysteine) proteinase inhibitor, clade A (alpha-1 antiproteinase, antitrypsin), member 1 |
| P01008 | Serine (or cysteine) proteinase inhibitor, clade C (antithrombin), member 1 |
| P05155 | Serine (or cysteine) proteinase inhibitor, clade G (C1 inhibitor), member 1, (angioedema, hereditary) |
| Q9Y275 | Tumor necrosis factor (ligand) superfamily, member 13b |
| O75083 | WD repeat domain 1 |
| P59998 | Actin related protein 2/3 complex, subunit 4 |

TABLE 6-continued

Global analysis of the cervical-vaginal proteome in pregnant rhesus monkeys using multidimensional protein identification technology (MudPIT) and gel-based fractionation (1D PAGE LC-MS/MS)

| Swiss-Prot™ ID | Protein Name |
|---|---|
| P14550 | Aldo-keto reductase family 1, member A1 (aldehyde reductase) |
| P04075 | Aldolase A, fructose-bisphosphate |
| P52907 | Capping protein (actin filament) muscle Z-line, alpha 1 |
| P40121 | Capping protein (actin filament), gelsolin-like |
| P04040 | Catalase |
| P07858 | Cathepsin B |
| Q13231 | Chitinase 1 (chitotriosidase) |
| P62937 | Cyclophilin A |
| P06733 | Enolase 1, (alpha) |
| Q14508 | Epididymal secretory protein E4 |
| P13639 | Eukaryotic translation elongation factor 2 |
| Q01469 | Fatty acid binding protein 5 (psoriasis-associated) |
| P00354 | GAPDH |
| P06396 | Gelsolin (amyloidosis, Finnish type) |
| Q7RTV2 | Glutathione S-transferase A5 |
| P04406 | Glyceraldehyde-3-phosphate dehydrogenase |
| P04792 | Heat shock 27 kDa protein 1 |
| P11142 | Heat shock 70 kDa protein 8 |
| P07900 | Heat shock 90 kDa protein 1, alpha |
| P22626 | Heterogeneous nuclear ribonucleoprotein A2/B1 |
| P16403 | Histone 1, H1c |
| P28001 | Histone 1, H2ab |
| P62807 | Histone 1, H2bo |
| P68431 | Histone 1, H3a |
| P62805 | Histone H4 |
| P08107 | HSP70-1/HSP70-2 |
| Q14914 | Leukotriene B4 12-hydroxydehydrogenase |
| P14174 | Macrophage migration inhibitory factor (MIF) (Phenylpyruvate tautomerase) |
| P40925 | Malate dehydrogenase 1, NAD (soluble) |
| Q8IW41 | Mitogen-activated protein kinase-activated protein kinase 5 |
| P30041 | Peroxiredoxin 6 |
| P52209 | Phosphogluconate dehydrogenase |
| P00558 | Phosphoglycerate kinase 1 |
| P18669 | Phosphoglycerate mutase 1 (brain) |
| P06737 | Phosphorylase, glycogen; liver (Hers disease, glycogen storage disease type VI) |
| P07237 | Procollagen-proline, 2-oxoglutarate 4-dioxygenase (proline 4-hydroxylase), beta polypeptide |
| Q9GLW7 | Prx-V |
| P14618 | Pyruvate kinase, muscle |
| P31949 | S100 calcium binding protein A11 (calgizzarin) |
| P15426 | TIM |
| Q12931 | TNF receptor-associated protein 1 |
| P37837 | Transaldolase 1 |
| P60174 | Triosephosphate isomerase 1 |
| P31946 | Tyrosine 3-monooxygenase/tryptophan 5-monooxygenase activation protein, beta polypeptide |
| P63104 | Tyrosine 3-monooxygenase/tryptophan 5-monooxygenase activation protein, zeta polypeptide |
| P61088 | Ubiquitin-conjugating enzyme E2N |
| P30085 | UMP-CMP kinase |
| P51451 | B lymphoid tyrosine kinase |
| Q01518 | CAP, adenylate cyclase-associated protein 1 (yeast) |
| P23528 | Cofilin 1 (non-muscle) |
| P16562 | Cysteine-rich secretory protein 2 |
| P19971 | Endothelial cell growth factor 1 (platelet-derived) |
| P21333 | Filamin A, alpha (actin binding protein 280) |
| P30101 | Glucose regulated protein, 58 kDa |
| P01833 | Polymeric immunoglobulin receptor |
| P15153 | ras-related C3 botulinum toxin substrate 2 (rho family, small GTP binding protein Rac2) |
| P52565 | Rho GDP dissociation inhibitor (GDI) alpha |
| P25815 | S100 calcium binding protein P |
| P31947 | Stratifin |
| P06753 | TRK-fused gene |
| P55072 | Valosin-containing protein |

TABLE 7

Differentially expressed proteins/peptides detected using MudPIT and de novo sequencing analysis of infected non-human primate CVF

| Protein ID | Description | Control Spectral Count | Infected Spectral Count | $\chi^2$ | Fold Change |
|---|---|---|---|---|---|
| (P04083) | Annexin A1 | 22 | 53 | 23.54 | 3.1 |
| (P05109) | Calgranulin A (Migration inhibitory factor-related protein 8) | 83 | 115 | 18.73 | 1.9 |
| (P08833) | Insulin-like growth factor binding protein 1 | 0 | 14 | 17.56 | 16.2 |
| (P31949) | Calgizzarin (S100 calcium-binding protein A11) | 1 | 16 | 17.23 | 10.2 |
| (Q9UBC9) | Small proline-rich protein 3 (Cornifin beta) | 1 | 16 | 17.23 | 10.2 |
| (P60709) | Actin, cytoplasmic 1 | 23 | 47 | 16.7 | 2.7 |
| (P07355) | Annexin A2 | 14 | 35 | 16.17 | 3.2 |
| (Q01469) | Fatty acid-binding protein, epidermal (E-FABP) | 12 | 30 | 13.85 | 3.1 |
| (P06702) | Calgranulin B (Migration inhibitory factor-related protein 14) | 170 | 187 | 13.32 | 1.5 |
| (P35322) | Cornifin (Small proline-rich protein I) (SPR-I) | 4 | 18 | 12.84 | 4.9 |
| (Q862Z5) | Cystatin B | 10 | 24 | 10.54 | 3 |
| (P14780) | Matrix metalloproteinase-9 precursor (MMP-9) | 25 | 40 | 9.12 | 2.1 |
| (P04217) | Alpha-1B-glycoprotein precursor | 13 | 0 | 8.91 | −8.7 |
| (P04196) | Histidine-rich glycoprotein precursor | 13 | 0 | 8.91 | −8.7 |
| (Q4R5C0) | Cofilin-1 (Cofilin, non-muscle isoform) | 0 | 6 | 7.01 | 7.7 |
| (P13796) | L-plastin (Lymphocyte cytosolic protein 1) | 26 | 36 | 5.73 | 1.8 |
| (P08133) | Annexin A6 | 8 | 16 | 5.46 | 2.5 |
| (P03973) | Antileukoproteinase 1 precursor | 26 | 8 | 5.33 | −2.2 |
| (Q28514) | Glutathione S-transferase P | 9 | 17 | 5.29 | 2.4 |
| (Q9GLV5) | Cathelin. | 24 | 32 | 4.55 | 1.7 |
| (P29034) | S100 calcium-binding protein A2 | 0 | 5 | 4.49 | 6.6 |
| (Q09666) | Neuroblast differentiation associated protein AHNAK | 0 | 4 | 3.22 | 5.6 |
| (P08246) | Leukocyte elastase precursor | 0 | 4 | 3.22 | 5.6 |
| (P16401) | Histone H1.5 (Histone H1a) | 0 | 4 | 3.22 | 5.6 |
| (P02545) | Lamin A/C (70 kDaa lamin) | 0 | 4 | 3.22 | 5.6 |
| (P25815) | S-100P protein | 0 | 4 | 3.22 | 5.6 |

TABLE 8

CVF proteins sharing significant changes between pair-wise comparisons of control, PTL, and PTB samples

| SwissProt™ accession number | Protein name | Spectral count | | | Fold change | | | p value | | |
|---|---|---|---|---|---|---|---|---|---|---|
| | | Control | PTL | PTB | PTL vs Control | PTB vs Control | PTB vs PTL | PTL vs Control | PTB vs Control | PTB vs PTL |
| P31151 | S100 calcium-binding protein A7* | 1 | 62 | 4 | 28.3 | 2.1 | −13.7 | 0.000 | 0.165 | 0.000 |
| Q9HC84 | Mucin-5B precursor | 21 | 85 | 39 | 3.9 | 1.6 | −2.4 | 0.000 | 0.019 | 0.000 |
| Q01469 | Fatty acid-binding protein, epidermal* | 209 | 116 | 58 | −1.9 | −4.3 | −2.3 | 0.000 | 0.000 | 0.000 |
| P15924 | Desmoplakin (DP) | 21 | 0 | 0 | −18.2 | −20.3 | | 0.000 | 0.000 | |
| Q9UBC9 | Small proline-rich protein 3 | 222 | 146 | 209 | −1.6 | −1.2 | 1.3 | 0.000 | 0.531 | 0.001 |
| P80188 | Neutrophil gelatinase-associated lipocalin | 17 | 43 | 35 | 2.4 | 1.8 | −1.4 | 0.001 | 0.012 | 0.365 |
| P62328 | Thymosin beta-4 (T beta 4) | 10 | 31 | 35 | 2.8 | 2.9 | 1 | 0.001 | 0.000 | 0.622 |
| P31949 | Calgizzarin* | 5 | 21 | 14 | 3.5 | 2.2 | −1.6 | 0.001 | 0.035 | 0.235 |
| P04792 | Heat-shock protein beta-1* | 30 | 11 | 4 | −2.6 | −6.8 | −2.6 | 0.002 | 0.000 | 0.065 |
| P62807 | Histone H2B | 0 | 9 | 0 | 8.1 | | −9.2 | 0.003 | | 0.003 |
| O60437 | Periplakin | 12 | 2 | 2 | −4.2 | −4.6 | −1.1 | 0.005 | 0.005 | 1.000 |
| P01040 | Cystatin A (Stefin A)* | 34 | 15 | 18 | −2.2 | −2.1 | 1.1 | 0.006 | 0.025 | 0.601 |
| P16403 | Histone H1.2 (Histone H1d) | 0 | 8 | 1 | 7.3 | 1.6 | −4.6 | 0.007 | 0.560 | 0.028 |
| P04406 | Glyceraldehyde-3-phosphate dehydrogenase | 16 | 35 | 39 | 2.1 | 2.1 | −1 | 0.007 | 0.002 | 0.642 |
| P13796 | L-plastin (Lymphocyte cytosolic protein 1) | 8 | 22 | 30 | 2.5 | 3 | 1.2 | 0.009 | 0.000 | 0.266 |
| P05109 | Calgranulin A* | 96 | 134 | 172 | 1.4 | 1.6 | 1.2 | 0.012 | 0.000 | 0.030 |
| P00338 | L-lactate dehydrogenase A chain | 0 | 7 | 0 | 6.5 | | −7.4 | 0.013 | | 0.013 |
| P14923 | Junction plakoglobin (Desmoplakin III) | 13 | 3 | 0 | −3.4 | −13 | −3.8 | 0.015 | 0.000 | 0.165 |
| P52566 | Rho GDP-dissociation inhibitor 2 | 1 | 7 | 12 | 3.6 | 5.2 | 1.4 | 0.024 | 0.001 | 0.249 |
| P31947 | 14-3-3 protein sigma* | 2 | 10 | 0 | 3.4 | −2.9 | −10.1 | 0.027 | 0.306 | 0.002 |
| P04080 | Cystatin B (Liver thiol proteinase inhibitor) | 50 | 73 | 19 | 1.4 | −2.9 | −4.2 | 0.038 | 0.000 | 0.000 |
| P12429 | Annexin A3 (Annexin III)* | 14 | 25 | 48 | 1.7 | 2.9 | 1.7 | 0.076 | 0.000 | 0.007 |
| P07737 | Profilin-1 (Profilin I) | 22 | 34 | 49 | 1.5 | 1.9 | 1.3 | 0.107 | 0.001 | 0.099 |
| P62805 | Histone H4 | 10 | 18 | 4 | 1.7 | −2.4 | −4.1 | 0.128 | 0.103 | 0.002 |
| P06702 | Calgranulin B* | 240 | 272 | 426 | 1.1 | 1.7 | 1.5 | 0.157 | 0.000 | 0.000 |
| P62937 | Peptidyl-prolyl cis-trans isomerase A | 14 | 8 | 0 | −1.7 | −13.9 | −8.3 | 0.218 | 0.000 | 0.007 |
| P02763 | Alpha-1-acid glycoprotein 1 precursor | 7 | 12 | 38 | 1.6 | 4.2 | 2.7 | 0.249 | 0.000 | 0.000 |
| P01009 | Alpha-1-antitrypsin precursor | 2 | 5 | 57 | 1.9 | 16.1 | 8.5 | 0.249 | 0.000 | 0.000 |
| P80511 | Calgranulin C | 0 | 2 | 21 | 2.6 | 15.8 | 6.2 | 0.306 | 0.000 | 0.000 |
| P01042 | Kininogen precursor | 3 | 1 | 10 | −1.9 | 2.3 | 4.5 | 0.306 | 0.046 | 0.003 |
| P02774 | Vitamin D-binding protein precursor (DBP) | 3 | 6 | 22 | 1.7 | 4.9 | 2.9 | 0.313 | 0.000 | 0.002 |
| P61626 | Lysozyme C precursor | 36 | 30 | 57 | −1.2 | 1.4 | 1.7 | 0.460 | 0.029 | 0.004 |
| P08758 | Annexin A5 (Annexin V) | 0 | 1 | 11 | 1.8 | 8.7 | 4.9 | 0.560 | 0.001 | 0.005 |
| P0883* | Insulin-like growth factor binding protein 1 | 0 | 1 | 4 | 1.8 | 3.7 | 2.1 | 0.560 | 0.080 | 0.250 |
| O43707 | Alpha-actinin 4 | 9 | 11 | 24 | 1.2 | 2.2 | 1.9 | 0.654 | 0.008 | 0.026 |
| P29508 | Squamous cell carcinoma antigen 1 | 80 | 83 | 35 | 1 | −2.6 | −2.6 | 0.814 | 0.000 | 0.000 |
| P02787 | Serotransferrin precursor (Transferrin) | 89 | 89 | 194 | −1 | 2 | 2 | 0.970 | 0.000 | 0.000 |
| P00738 | Haptoglobin precursor | 16 | 16 | 40 | −1 | 2.1 | 2.2 | 1.000 | 0.001 | 0.001 |
| P02751# | Fibronectin precursor (FN) | 0 | 0 | 4 | | 3.7 | 3.7 | | 0.080 | 0.080 |

Proteins that showed significant fold change but did not reach statistical significance due to small number of spectral counts.
*Proteins that also showed differential expression from 2D-DIGE analysis.

TABLE 9

CVF proteins showing progressive differences in relative abundance contol <PTLTB

| SwissProt™ accession number | Protein name | Spectral count | | | p value* |
|---|---|---|---|---|---|
| | | Control | PTL | PTB | |
| P06702 | Calgranulin B | 240 | 272 | 426 | 0.000 |
| P02787 | Serotransferrin precursor | 88.5 | 89 | 194 | 0.000 |
| P05109 | Calgranulin A | 96 | 134 | 172 | 0.000 |
| Q01469 | Fatty acid-binding protein, epidermal | 209 | 116 | 58 | 0.000 |
| P01009 | Alpha-1-antitrypsin precursor | 2 | 5 | 57 | 0.000 |
| P07737 | Profilin-1 (Profilin I) | 22 | 34 | 49 | 0.002 |
| P12429 | Annexin A3 (Annexin III) | 14 | 25 | 48 | 0.000 |
| P00738 | Haptoglobin precursor | 16 | 16 | 40 | 0.002 |
| P04406 | Glyceraldehyde-3-phosphate dehydrogenase, liver | 16 | 35 | 39 | 0.003 |
| P02763 | Alpha-1-acid glycoprotein 1 precursor (AGP 1) | 7 | 12 | 38 | 0.000 |
| P62328 | Thymosin beta-4 (T beta 4) | 10 | 31 | 35 | 0.000 |

TABLE 9-continued

CVF proteins showing progressive differences in relative abundance contol <PTLTB

| SwissProt™ accession number | Protein name | Spectral count Control | PTL | PTB | p value* |
|---|---|---|---|---|---|
| P13796 | L-plastin (Lymphocyte cytosolic protein 1) | 8 | 22 | 30 | 0.001 |
| P80511 | Calgranulin C | 1 | 3 | 22 | 0.003 |
| P02774 | Vitamin D-binding protein precursor | 3 | 6 | 22 | 0.001 |
| P04792 | Heat-shock protein beta-1 (HspB1) | 30 | 11 | 4 | 0.000 |
| P15924 | Desmoplakin (DP) | 22 | 1 | 1 | 0.003 |

*Statistical significance was defined at FDR of 0.05 after adjustment for multiple comparisons

TABLE 10

2D-LC-MS/MS analysis: Cervical-vaginal fluid biomarkers to detect Intra-amniotic infection in preterm labor cases

| Swissprot™ ID | Protein_name | Swissprot™ symbol | Preterm labor | Preterm labor +IAI | Fold change | p_value |
|---|---|---|---|---|---|---|
| P29508 | Squamous cell carcinoma antigen 1 (SCCA-1) | SCCA1_HUMAN | 101 | 1 | 45.31 | 0.000 |
| P07355 | Annexin-A2 (Annexin II) (Lipocortin II) | ANXA2_HUMAN | 43 | 1 | 19.25 | 0.000 |
| P31151 | S100 calcium-binding protein A7 (Psoriansin) | S10A7_HUMAN | 17 | 1 | 7.87 | 0.000 |
| O60437 | Periplakin | PEPL_HUMAN | 17 | 1 | 7.87 | 0.026 |
| P11142 | Heat shock cognate 71 kDa protein | HSP7C_HUMAN | 14 | 1 | 6.57 | 0.006 |
| P07476 | Involucrin | INVO_HUMAN | 11 | 1 | 5.27 | 0.001 |
| Q01469 | Fatty acid-binding protein, eipidermal (E-FABP) | FABPE_HUMAN | 302 | 62 | 5.23 | 0.000 |
| P10599 | Thioredoxin (ATL-derived factor) (ADF) | THIO_HUMAN | 32 | 9 | 3.39 | 0.001 |
| P62805 | Histone H4 | H4_HUMAN | 54 | 16 | 3.21 | 0.003 |
| Q09666 | Neuroblast differentiation associated protein AHNAK | AHNK_HUMAN | 16 | 5 | 2.60 | 0.000 |
|  | Annexin A1 (Annexin I) (Lipocortin I) | ANXA1_HUMAN | 44 | 18 | 2.33 | 0.000 |
| P60709 | Actin, cytoplasmic 1 (Beta-actin) | ACTG_HUMAN | 9 | 3 | 2.29 | 0.006 |
| P04792 | Heat-shock protein beta-1 (HspB1) | HSPB1_HUMAN | 31 | 15 | 1.98 | 0.004 |
| P04075 | Fructose-bisphosphate aldolase A (EC 4.1.2.13) | ALDOA_HUMAN | 25 | 13 | 1.86 | 0.005 |
| Q9HC84 | Mucin-5B precursor | MUC5B_HUMAN | 37 | 22 | 1.68 | 0.000 |
| P35326 | Small praline-rich protein 2A (SPR-2A)(2-1) | SPR2A_HUMAN | 41 | 27 | 1.50 | 0.000 |
| P01040 | Cystatin A (Stefin A) (Cystatin AS) | CYTA_HUMAN | 15 | 10 | 1.48 | 0.000 |
| P05164 | Myeloperoxidase precursor | PERM_HUMAN | 52 | 36 | 1.45 | 0.046 |
| P35321 | Cronifin A (Small praline-rich protein IA) (SPR-IA) | SPR1A_HUMAN | 45 | 32 | 1.38 | 0.000 |
| P80188 | Neutrophil gelatinase-associatede lipocalin precursor | NGAL_HUMAN | 48 | 36 | 1.34 | 0.000 |
| Q9UBC9 | Small praline-rich protein 3 (Cornifin beta) | SPRR3_HUMAN | 162 | 123 | 1.33 | 0.000 |
| P02790 | Hemopexin precursor (Beta-1B-glycoprotein) | HEMO_HUMAN | 9 | 13 | −1.39 | 0.047 |
| P02787 | Serotransferrin precursor (Transferrin) | TRFE_HUMAN | 98 | 177 | −1.84 | 0.001 |
| P04040 | Catalase (EC 1.11.1.6) | CATA_HUMAN | 6 | 19 | −2.86 | 0.002 |
| P61626 | Lysozyme C precursor (EC 3.2.1.17) | LYSC_HUMAN | 19 | 57 | −2.92 | 0.005 |
| P14780 | Matrix metallogproteinase-9 precursor (MMP-9) kDa n | MMP9_HUMAN | 8 | 26 | −2.95 | 0.021 |
| P00738 | Haptoglobin precursor | HPT_HUMAN | 21 | 66 | −3.06 | 0.000 |
| P07737 | Profilin-1 (Profilin I) | PROF1_HUMAN | 6 | 22 | −3.17 | 0.000 |
| P02768 | Serum albumin precursor | ALBU_HUMAN | 492 | 1249 | −3.53 | 0.000 |
| P02751 | Fibronectin precursor (FN) (Cold-insoluble globulin) | FINC_HUMAN | 1 | 8 | −3.92 | 0.000 |
| P80723 | Brain acid soluble protein 1 (BASP1 protein) | BASP_HUMAN | 2 | 15 | −5.06 | 0.001 |
| P04406 | Glyceraldehyde-3-phosphate dehydrogenase | G3P2_HUMAN | 3 | 28 | −6.95 | 0.000 |
| P02774 | Vitamin D-binding protein precursor (DBP) | VTDB_HUMAN | 1 | 18 | −8.76 | 0.023 |

TABLE 11

2D-LC-MS/MS analysis: Cervical-vaginal fluid biomarkers to detect Intra-amniotic infection in preterm birth cases

| Swissprot™ ID | Protein_name | Swissprot™ symbol | Preterm birth | Preterm birth +IAI | Fold change | p_value |
|---|---|---|---|---|---|---|
| P00738 | Haptoglobin precursor | HPT_HUMAN | 7.11 | 65.853 | 8.17 | 0.000 |
| P07737 | Profilin-1 (Profilin 1) | PROF1_HUMAN | 2.37 | 21.591 | 6.35 | 0.002 |
| P80723 | Brain acid soluble protein I (BASP1 protein) | BASP_HUMAN | 2.37 | 15.114 | 4.54 | 0.001 |
| P04075 | Fructose-bisphosphate aldolase A | ALDOA_HUMAN | 2.37 | 12.955 | 3.94 | 0.049 |
| P04406 | Glyceraldehyde-3-phosphate dehydrogenase | G3P2_146MAN | 7.11 | 28.069 | 3.53 | 0.000 |
| P04040 | Catalase (EC 1.11.1.6) | CATA_HUMAN | 4.74 | 19.432 | 3.47 | 0.006 |
| O43707 | Alpha-actinin 4 (Non-muscle alpha-actinin 4) | ACTN4_HUMAN | 2.37 | 8.637 | 2.74 | 0.000 |
| P35579 | Myosin-9 (Myosin heavy chain, nonmuscie ha) | MYH9_HUMAN | 2.37 | 8.637 | 2.74 | 0.035 |
| P02768 | Serum albumin precursor | ALBU_HUMAN | 628.36 | 1249.056 | 2.63 | 0.000 |
| P02774 | Vitamin D-binding protein precursor (DBP) | VTDB_HUMAN | 7.11 | 18.353 | 2.35 | 0.000 |
| P14780 | Matrix metalloproteinase-9 precursor (MMP-9) kDa matrix metalloproteinase | MMP9_HUMAN | 11.86 | 25.91 | 2.08 | 0.002 |

TABLE 11-continued

2D-LC-MS/MS analysis: Cervical-vaginal fluid biomarkers to detect Intra-amniotic infection in preterm birth cases

| Swissprot™ ID | Protein_name | Swissprot™ symbol | Preterm birth | Preterm birth +IAI | Fold change | p_value |
|---|---|---|---|---|---|---|
| P80511 | Calgranulin C (CAGO) (CGRP (Neutrophil S100 protein) | S10AC_HUMAN | 4.74 | 10.796 | 2.01 | 0.002 |
| P62328 | Thymosin beta-4 (T beta 4) | TYB4_HUMAN | 7.11 | 15.114 | 1.96 | 0.000 |
| P61626 | Lysozyme C precursor (EC 3.2.1.17) | LYSC_HUMAN | 30.83 | 57.217 | 1.84 | 0.000 |
| P04080 | Cystatin B (Liver thiol proteinase inhibitor) | CYTB_HUMAN | 11.86 | 19.432 | 1.58 | 0.000 |
| P02787 | Serotransferrin precursor (Transferrin) | TRFE_HUMAN | 118.56 | 177.049 | 1.52 | 0.000 |
| P02763 | Alpha-1-acid glycoprotein 1 precursor (AGP 1) | A1AG1_HUMAN | 4.74 | 7.557 | 1.47 | 0.017 |
| P02749 | Beta-2-glycoprotein I precursor (Apolipoprotein H) | APOH_HUMAN | 4.74 | 7.557 | 1.47 | 0.017 |
| P10153 | Nonsecretory ribonuclease precursor | RNAS2_HUMAN | 4.74 | 7.557 | 1.47 | 0.017 |
| P02765 | Alpha-2-HS-glycoprotein precursor (Fetuin-A) | FETUA_HUMAN | 7.11 | 10.796 | 1.44 | 0.002 |
| P04217 | Alpha-1 B-glycoprotein precursor (Alpha-1-B glycoprotein) | A1BG_HUMAN | 4.74 | 6.477 | 1.29 | 0.034 |
| O75594 | Peptidoglycan recognition protein precursor (SBB1 68) (PGRP-S) | PGRP_HUMAN | 4.74 | 6.477 | 1.29 | 0.034 |
| P12429 | Annexin A3 (Anne)dn III) (Lipocortin III) | ANXA3_HUMAN | 16.60 | 20.512 | 1.22 | 0.001 |
| P29034 | S100 calcium-binding protein A2 (S-100L protein) (CAN 19) | S1OA2_HUMAN | 2.37 | 2.159 | −1.06 | 0.019 |
| P06753 | Tropomyosin alpha 3 chain (Tropomyosin 3) | TPM3_HUMAN | 2.37 | 2.159 | −1.06 | 0.000 |
| P02788 | Lactotransferrin precursor (Lactofernn) | TRFL_HUMAN | 75.88 | 59.376 | −1.28 | 0.000 |
| Q9UBC9 | Small proline-rich protein 3 (Cornifin beta) | SPRR3_HUMAN | 208.66 | 123.07 | −1.74 | 0.021 |
| Q9UKR3 | Kallikrein 13 precursor | KLK13_HUMAN | 4.74 | 2.159 | −1.76 | 0.002 |
| O01469 | Fatty acid-binding protein, epidermal (E-FABP) | FABPE_HUMAN | 128.04 | 61.535 | −2.10 | 0.000 |
| P62805 | Histone H4 | H4_HUMAN | 37.94 | 16.193 | −2.26 | 0.000 |
| P04792 | Heat-shock protein beta-1 (HspB1)(Heat shock 27 kDa protein) | HSPB1_HUMAN | 35.57 | 15.114 | −2.26 | 0.018 |
| P04083 | Annexin Al (Annexin I) (Lipocortin I) | ANXA1_HUMAN | 54.54 | 18.353 | −2.88 | 0.001 |
| P10599 | Thioredoxin (ATL-derived factor) (ADF) | THIO_HUMAN | 28.45 | 8.637 | −3.02 | 0.000 |
| Q60437 | Periplakin (195 kDa cornified envelope precursor protein) | PEPL_HUMAN | 7.11 | 1.08 | −3.60 | 0.000 |
| P11142 | Heat shock cognate 71 kDa protein (Heat shock 70 kDa protein 8) | HSP7C_HUMAN | 9.49 | 1.08 | −4.62 | 0.000 |
| Q9HC84 | Mucin-5B precursor (Mucin 5 subtype B, tracheobronchial) | MUC5B_HUMAN | 116.19 | 21.591 | −5.30 | 0.043 |
| P07476 | Involucrin | INVO_HUMAN | 11.86 | 1.08 | −5.64 | 0.002 |
| O09666 | Neuroblast differentiation associated protein AHNAK | AHNK_HUMAN | 45.05 | 5.398 | −7.05 | 0.019 |
| P02751 | Fibronectin precursor (FN) (Cold-insoluble globulin) (CIG) | FINC_HUMAN | 61.65 | 7.557 | −7.27 | 0.017 |
| P07355 | Annexin A2 (Annexin II) (Lipocortin II) | ANXA2_HUMAN | 16.60 | 1.08 | −7.70 | 0.000 |
| P29508 | Squamous cell carcinoma antigen 1 (SCCA-1) | SCCA1_HUMAN | 18.97 | 1.08 | −8.73 | 0.000 |
| P31151 | S100 calcium-binding protein A7 (Psoriasin) | S10A7_HUMAN | 33.20 | 1.08 | −14.93 | 0.000 |

What is claimed:

1. A method for determining the presence of intra-uterine infection in a pregnant female mammalian subject comprising: (a) testing in a sample of cervical-vaginal fluid obtained from said subject the abundance of fatty acid-binding protein, epidermal, and one or more proteins selected from the group consisting of haptoglobin precursor; alpha-1-acid glycoprotein, and insulin-like growth factor binding protein relative to the abundance in normal cervical fluid or cervical fluid known to be indicative of intra-uterine infection; and (b) concluding that intra-uterine infection is present if said abundance shows a statistically significant difference relative to abundance in said normal cervical fluid, or does not show a statistically significant difference relative to abundance in said cervical fluid known to be indicative of intra-uterine infection.

2. The method of claim 1 wherein said mammalian subject is human.

3. The method of claim 2 comprising testing the abundance of fatty acid-binding protein, epidermal, and at least two of said proteins.

4. The method of claim 2 comprising testing the abundance of fatty acid-binding protein, epidermal, and at least three of said proteins.

5. The method of claim 2 further comprising testing the abundance of one or more additional proteins selected from the group consisting of profilin-1; serum albumin precursor; calgranulin B; and squamous cell carcinoma antigen 1.

6. The method of claim 2 or claim 5 further comprising testing the abundance of one or more additional proteins selected from the group consisting of alpha-1-antitrypsin precursor; fibronectin precursor; Annexin A2; Vitamin-D binding protein precursor.

7. The method of claim 6 further comprising testing the abundance of one or more additional proteins selected from the group consisting of cystatin A; mucin-5B precursor; small proline-rich protein 3; lysozyme C precursor; and serotransferrin precursor (P02787).

8. The method of claim 1 or claim 5 further comprising testing the abundance of one or more additional proteins selected from the group consisting of cystatin; mucin-5B precursor; small proline-rich protein 3; lysozyme C precursor; and serotransferrin precursor (P02787).

9. The method of claim 2 wherein said abundance is determined by an immunoassay.

* * * * *

SEQUENCE LISTING

<160> NUMBER OF SEQ ID NOS: 11

<210> SEQ ID NO 1
<211> LENGTH: 259
<212> TYPE: PRT
<213> ORGANISM: Homo Sapiens

<400> SEQUENCE: 1

Met Ser Glu Val Pro Val Ala Arg Val Trp Leu Val Leu Leu Leu Leu
 1               5                  10                  15

Thr Val Gln Val Gly Val Thr Ala Gly Ala Pro Trp Gln Cys Ala Pro
                20                  25                  30

Cys Ser Ala Glu Lys Leu Ala Leu Cys Pro Pro Val Ser Ala Ser Cys
            35                  40                  45

Ser Glu Val Thr Arg Ser Ala Gly Cys Gly Cys Cys Pro Met Cys Ala
        50                  55                  60

Leu Pro Leu Gly Ala Ala Cys Gly Val Ala Thr Ala Arg Cys Ala Arg
65                  70                  75                  80

Gly Leu Ser Cys Arg Ala Leu Pro Gly Glu Gln Gln Pro Leu His Ala
                85                  90                  95

```
Leu Thr Arg Gly Gln Gly Ala Cys Val Gln Glu Ser Asp Ala Ser Ala
            100                 105                 110
Pro His Ala Ala Glu Ala Gly Ser Pro Glu Ser Pro Glu Ser Thr Glu
            115                 120                 125
Ile Thr Glu Glu Glu Leu Leu Asp Asn Phe His Leu Met Ala Pro Ser
130                 135                 140
Glu Glu Asp His Ser Ile Leu Trp Asp Ala Ile Ser Thr Tyr Asp Gly
145                 150                 155                 160
Ser Lys Ala Leu His Val Thr Asn Ile Lys Lys Trp Lys Glu Pro Cys
                165                 170                 175
Arg Ile Glu Leu Tyr Arg Val Val Glu Ser Leu Ala Lys Ala Gln Glu
            180                 185                 190
Thr Ser Gly Glu Glu Ile Ser Lys Phe Tyr Leu Pro Asn Cys Asn Lys
            195                 200                 205
Asn Gly Phe Tyr His Ser Arg Gln Cys Glu Thr Ser Met Asp Gly Glu
        210                 215                 220
Ala Gly Leu Cys Trp Cys Val Tyr Pro Trp Asn Gly Lys Arg Ile Pro
225                 230                 235                 240
Gly Ser Pro Glu Ile Arg Gly Asp Pro Asn Cys Gln Ile Tyr Phe Asn
                245                 250                 255
Val Gln Asn

<210> SEQ ID NO 2
<211> LENGTH: 14
<212> TYPE: PRT
<213> ORGANISM: Homo Sapien

<400> SEQUENCE: 2

Ala Leu Pro Gly Glu Gln Gln Pro Leu His Ala Leu Thr Arg
1               5                   10

<210> SEQ ID NO 3
<211> LENGTH: 9
<212> TYPE: PRT
<213> ORGANISM: Homo sapien

<400> SEQUENCE: 3

Arg Ile Pro Gly Ser Pro Glu Ile Arg
1               5

<210> SEQ ID NO 4
<211> LENGTH: 94
<212> TYPE: PRT
<213> ORGANISM: Homo sapiens

<400> SEQUENCE: 4

Ala Leu His Val Thr Asn Ile Lys Lys Trp Lys Glu Pro Cys Arg Ile
1               5                   10                  15
Glu Leu Tyr Arg Val Val Glu Ser Leu Ala Lys Ala Gln Glu Thr Ser
            20                  25                  30
Gly Glu Glu Ile Ser Lys Phe Tyr Leu Pro Asn Cys Asn Lys Asn Gly
        35                  40                  45
Phe Tyr His Ser Arg Gln Cys Glu Thr Ser Met Asp Gly Glu Ala Gly
50                  55                  60
Leu Cys Trp Cys Val Tyr Pro Trp Asn Gly Lys Arg Ile Pro Gly Ser
65                  70                  75                  80
Pro Glu Ile Arg Gly Asp Pro Asn Cys Gln Ile Tyr Phe Asn
                85                  90
```

```
<210> SEQ ID NO 5
<211> LENGTH: 139
<212> TYPE: PRT
<213> ORGANISM: Homo sapiens

<400> SEQUENCE: 5

Ala Gly Trp Asn Ala Tyr Ile Asp Asn Leu Met Ala Asp Gly Thr Cys
 1               5                  10                  15

Gln Asp Ala Ala Ile Val Gly Tyr Lys Asp Ser Pro Ser Val Trp Ala
             20                  25                  30

Ala Val Pro Gly Lys Thr Phe Val Asn Ile Thr Pro Ala Glu Val Gly
         35                  40                  45

Val Leu Val Gly Lys Asp Arg Ser Ser Phe Tyr Val Asn Gly Leu Thr
 50                  55                  60

Leu Gly Gly Gln Lys Cys Ser Val Ile Arg Asp Ser Leu Leu Gln Asp
 65                  70                  75                  80

Gly Glu Phe Ser Met Asp Leu Arg Thr Lys Ser Thr Gly Gly Ala Pro
                 85                  90                  95

Thr Phe Asn Val Thr Val Thr Lys Thr Asp Lys Thr Leu Val Leu Leu
            100                 105                 110

Met Gly Lys Glu Gly Val His Gly Gly Leu Ile Asn Lys Lys Cys Tyr
        115                 120                 125

Glu Met Ala Ser His Leu Arg Arg Ser Gln Tyr
        130                 135

<210> SEQ ID NO 6
<211> LENGTH: 10
<212> TYPE: PRT
<213> ORGANISM: Home sapiens

<400> SEQUENCE: 6

Pro Ser Val Trp Ala Ala Gly Pro Arg
 1               5                  10

<210> SEQ ID NO 7
<211> LENGTH: 14
<212> TYPE: PRT
<213> ORGANISM: Homo sapiens

<400> SEQUENCE: 7

Ser Thr Gly Gly Ala Pro Thr Phe Asn Val Thr Val Thr Lys
 1               5                  10

<210> SEQ ID NO 8
<211> LENGTH: 16
<212> TYPE: PRT
<213> ORGANISM: Homo sapiens

<400> SEQUENCE: 8

Thr Phe Val Asn Ile Thr Pro Ala Glu Val Gly Val Leu Val Gly Lys
 1               5                  10                  15

<210> SEQ ID NO 9
<211> LENGTH: 12
<212> TYPE: PRT
<213> ORGANISM: Homo sapiens

<400> SEQUENCE: 9

Asp Ser Pro Ser Val Trp Ala Val Pro Gly Lys
 1               5                  10
```

```
<210> SEQ ID NO 10
<211> LENGTH: 12
<212> TYPE: PRT
<213> ORGANISM: Homo sapiens

<400> SEQUENCE: 10

Asp Ser Pro Ser Val Trp Ala Ala Val Pro Gly Lys
 1               5                  10

<210> SEQ ID NO 11
<211> LENGTH: 16
<212> TYPE: PRT
<213> ORGANISM: Homo sapiens

<400> SEQUENCE: 11

Thr Phe Val Asn Ile Thr Pro Ala Glu Val Gly Val Leu Val Gly Lys
 1               5                  10                  15
```